(12) United States Patent
Vazquez-Martinez et al.

(10) Patent No.: US 7,923,015 B2
(45) Date of Patent: Apr. 12, 2011

(54) METHODS FOR DIRECT VISUALIZATION OF ACTIVE SYNAPSES

(75) Inventors: Rafael Vazquez-Martinez, Cordova (ES); Philippe Brulet, Paris (FR)

(73) Assignees: Institut Pasteur, Paris (FR); Centre Nationale de la Recherche Scientifique, Paris (FR)

( * ) Notice: Subject to any disclaimer, the term of this patent is extended or adjusted under 35 U.S.C. 154(b) by 0 days.

(21) Appl. No.: 10/817,961

(22) Filed: Apr. 6, 2004

(65) Prior Publication Data

US 2005/0060761 A1  Mar. 17, 2005

Related U.S. Application Data

(63) Continuation-in-part of application No. 10/662,808, filed on Sep. 16, 2003, which is a continuation-in-part of application No. 09/816,467, filed on Mar. 26, 2001, now Pat. No. 7,435,792, which is a continuation of application No. 09/129,368, filed on Aug. 5, 1998, now abandoned.

(60) Provisional application No. 60/055,615, filed on Aug. 14, 1997, provisional application No. 60/065,236, filed on Nov. 13, 1997.

(51) Int. Cl.
*G01N 33/53* (2006.01)
*C07K 1/00* (2006.01)
*A61K 39/00* (2006.01)
*C12N 15/63* (2006.01)
*C07H 21/04* (2006.01)

(52) U.S. Cl. .......... 424/192.1; 435/7.72; 435/320.1; 435/455; 530/350; 536/23.4

(58) Field of Classification Search .......... 530/350; 424/192.1; 536/23.1, 23.4; 514/44; 435/7.72, 435/320.1, 455
See application file for complete search history.

(56) References Cited

U.S. PATENT DOCUMENTS

| 4,479,940 | A |   | 10/1984 | Bizzini |  |
|---|---|---|---|---|---|
| 4,594,336 | A |   | 6/1986 | Bizzini |  |
| 5,004,683 | A | * | 4/1991 | Erichsen et al. | 435/7.21 |
| 5,082,670 | A |   | 1/1992 | Gage et al. |  |
| 5,580,859 | A |   | 12/1996 | Felgner et al. |  |
| 5,589,466 | A |   | 12/1996 | Felgner et al. |  |
| 5,643,578 | A |   | 7/1997 | Robinson et al. |  |
| 5,728,383 | A |   | 3/1998 | Johnson et al. |  |
| 5,728,399 | A |   | 3/1998 | Wu et al. |  |
| 5,762,926 | A |   | 6/1998 | Gage et al. |  |
| 5,766,948 | A | * | 6/1998 | Gage et al. | 435/368 |
| 5,780,024 | A |   | 7/1998 | Brown et al. |  |
| 5,840,540 | A |   | 11/1998 | George-Hyslop et al. |  |
| 6,005,004 | A |   | 12/1999 | Katz et al. |  |
| 6,159,948 | A |   | 12/2000 | Robertson et al. |  |

FOREIGN PATENT DOCUMENTS

| CA | 1152493 | 8/1983 |
|---|---|---|
| CA | 1178949 | 12/1984 |
| EP | 0 030 496 | 6/1981 |
| WO | WO 95/04151 | 2/1995 |
| WO | WO 97/07668 | 3/1997 |
| WO | WO 99/09057 | 2/1999 |
| WO | WO 01/52843 A | 7/2001 |
| WO | WO 01/58936 | 8/2001 |
| WO | WO/2005/025592 | 3/2005 |
| WO | WO/2005/097200 | 10/2005 |

OTHER PUBLICATIONS

Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Figueiredo et al., Jun. 1997, Experimental Neurology, vol. 145, p. 546-554.*
Kissa et al., 2002, Molecular and Cellular Neuroscience, vol. 20, p. 627-637.*
Coen et al., 1997, PNAS, vol. 94, pp. 9400-9405.*
Coen et al., 1999, Int. J. Dev. Biol., vol. 43, p. 823-830.*
Erdmann et al., "Intraaxonal and Extraaxonal Transport of $^{125}$I-Tetanus Toxin in Early Local Tetanus," *Naunyn-Schmiedeberg's Arch. Pharmacol*, 290, pp. 357-373 (1975).
Price et al., "Tetanus Toxin: Direct Evidence for Retrograde Intraaxonal Transport," *Science*, vol. 188, pp. 945-947 (1975).
Stockel et al., "Comparison Between the Retrograde Axonal Transport of Nerve Growth Factor and Tetanus Toxin in Motor, Sensory and Adrenergic Neurons," *Brain Research*, 99, pp. 1-16 (1975).
Rudinger, "Peptide Hormones", edited by Parsons, J., University Park Press, Baltimore, p. 1-7 (1976).
Schwab et al., "Electron Microscopic Evidence for a Transsynaptic Migration of Tetanus Toxin in Spinal Cord Motoneurons: An Autoradiographic and Morphometric Study," *Brain Research*, 105, pp. 213-227 (1976).
Helting et al., "Structure of Tetanus Toxin," *The Journal of Biological Chemistry*, 252, (1), pp. 187-193 (1977).
Eisel et al., "Tetanus Toxin: Primary Structure, Expression in *E. coli*, and Homology with Botulinum Toxins," *The EMBO Journal*, 5, (10), pp. 2495-2502 (1986).
Fairweather et al., "Immunization of Mice Against Tetanus With Fragments of Tetanus Toxin Synthesized in *Escherichia coli*," *Infection and Immunity*, vol. 55, No. 11, pp. 2541-2545 (Nov. 1987).
Beaude et al., "Retrograde Axonal Transport of an Exogenous Enzyme Covalently Linked to B-II$_b$ Fragment of Tetanus Toxin," *Biochem. J.*, 271, pp. 87-91 (1990).

(Continued)

*Primary Examiner* — Shin-Lin Chen
(74) *Attorney, Agent, or Firm* — Finnegan, Henderson, Farabow, Garrett & Dunner LLP

(57) ABSTRACT

A method for visualizing an active synapse wherein said method comprises: (a) exposing cells forming the active synapse to a biomarker comprising at least fragment C of tetanus toxin and a reporter protein; and (b) visualizing the biomarker; wherein the accumulation of the biomarker into dendritic spines of the cells allows visualization of an active synapse. Also, a method for screening molecules capable of modulating synapse activity is provided. A kit useful for the early diagnosis of neurodegenerative disease comprises a biomarker comprising at least fragment C of tetanus toxin and a reporter protein.

23 Claims, 22 Drawing Sheets
(4 of 22 Drawing Sheet(s) Filed in Color)

OTHER PUBLICATIONS

Fishman et al., "Enhanced CNS Uptake of Systemically Administered Proteins Through Conjunction with Tetanus C-fragment," *Journal of the Neurological Sciences*, 98, pp. 311-325 (1990).

Kaye et al. *PNAS*, USA, vol. 87, pp. 6922-6926 (1990).

Kuypers et al., "Viruses as Transneuronal Tracers," *TINS*, 13, (2), pp. 71-75 (1990).

Hazinski et al., *Am. J. Respir. Cell Mol. Biol.*, vol. 4(3), pp. 206-209 (1991).

Hohne-Zell et al., *FEBS Letters*, vol. 336, No. 1, p. 175-180 (1993).

Boucher et al., "Neutralizing Antibodies and Immunoprotection Against Pertussis and Tetanus Obtained by Use of a Recombinant Pertussis Toxin-Tetanus Toxin Fusion Protein," *Infection and Immunity*, vol. 62, No. 2, pp. 449-456 (1994).

Mueller, ARO-27890.1-LS, Order No. AD-A290 501, NTIS, p. 1-15 (1994).

Francis et al., "CuZn Superoxide Dismutase (SOD-1): Tetanus Toxin Fragment C Hybrid Protein for Targeted Delivery of SOD-1 to Neuronal Cells," *The Journal of Biological Chemistry*, 270, (25), pp. 15434-15442 (1995).

Montecucco et al., "Structure and Function of Tetanus and Botulinum Neurotoxins,"*Quarterly Reviews of Biophysics*, 28, pp. 423-472 (1995).

Orkin et al., *Recommendations of the Panel to Assess the NIH Investment in Research on Gene Therapy* (Dec. 1995).

Liston et al., "Suppression of Apoptosis in Mammalian Cells by NAIP and a Related Family of IAP Genes," *Nature*, vol. 379, pp. 349-353 (Jan. 25, 1996).

Figueiredo et al., "Delivery of Recombinant Tetanus-Superoxide Dismutase Proteins to Central Nervous System Neurons by Retrograde Axonal Transport," *Experimental Neurology*, 145, pp. 546-554 (1997).

Coen et al., "Construction of Hybrid Proteins that Migrate Retrogradely and Transynaptically Into the Central Nervous System", PNAS USA, vol. 94, pp. 9400-9405 (1997).

Maskos et al., "Retrograde trans-synaptic transfer of green fluorescent protein allows the genetic mapping of neuronal circuits in transgenic mice", PNAS USA, vol. 99, pp. 10120-10125 (2002).

Database EMBL [Online], EBI; Dec. 8, 2004, Database Accession No. EM_PRO:AE005174.

St. Pierre and Linn, "A refined vector system for the In vitro construction of single-copy transcriptional or translational fusions to lacZ" Gene, vol. 169, pp. 65-68 (996).

Eisel et al., "Tetanus toxin: primary structure, expression in *E. coli*, and homology with botulinum toxins", Embo J., vol. 5, pp. 2495-2502 (1986).

Database EMBL [Online], EBI; Feb. 5, 2003, Database Accession No. EM_PRO:AF528097.

Roux et al., "Utilisation du fragment C-terminal de la neurotoxine tétanique pour visualiser et analyser des connexions neuronales et pour le transfert d'une activité biologique associée", Journal De La Société de Biologie, vol. 199, pp. 35-44 (2005).

International Search Report for PCT/EP2005/004314.

Bendig et al., "Differential Expression of the *Xenopus laevis* Tadpole and Adult β-Globin When Injected into Fertilized *Xenopus laevis* Eggs", MCB 4:567-570 (1984).

Bendig et al., "Replication and expression of *Xenopus laevis* globin into fertilized *Xenopus* eggs", PNAS 80:6197-6201 (1983).

Bürki et al., "Transplantation of the human insulin gene into fertilized mouse eggs", EMBO 1:127-131 (1982).

Chanock et al., "Immunization by Selective Infection With Type 4 Adenovirus Grown in Human Diploid Tissue Culture", JAMA, 195:151-158 (1966).

Cohen et al., Inducible transcription and puffing in *Drosophila melanogaster* transformed with *hsp70*-phage λ hybrid heat shock genes, PNAS 81:5509-13 (1984).

Fox et al., "DNA-Induced Transformation in *Drosophila*: Genetic Analysis of Transformed Stocks", PNAS 68:342-346 (1971).

Gehring et al., "Functional analysis of the *white+* gene of *Drosophila* by P-factor-mediated transformation", EMBO 3:2077-85 (1984).

Gordon et al., "Gene Transfer into Mouse Embroys : Production of Transgenic Mice by Pronuclear Injection", Methods in Enzymology 101:411-433 (1983).

Gordon et al., Genetic transformation of mouse embroys by microinjection of purified DNA , PNAS 77 :7380-84 (1980).

Levrero et al., "Defective and nondefective adenovirus vectors for expressing foreign genes in vitro and in vivo", Gene 101:195-202 (1991).

Miller et al., A transmissible retrovirus expressing human hypoxanthine phosphoribosyltransferase (HPRT): Gene transfer into cells obtained from humans deficient in HPTR, PNAS 80:4709-13 (1983).

Richards et al., "The normal developmental regulation of a cloned *sgs*3 'glue' gene chromosomally integrated in *Drosophila melanogaster* by P element transformation", EMBO 2:2137-2142 (1983).

Rubin et al., "Vectors for P element-mediated gene transfer in *Drosophila*", NAR 11:6341-6351 (1983).

Rusconi et al., "Transformation of frog embryos with a rabbit β-globin gene", PNAS 78:5051-5055 (1981).

Steller et al., "Regulated expression of genes injected into early *Drosophila* embroys", EMBO 3:165-173 (1984).

Stuhlmann et al., "Introduction of a selectable gene into different animal tissue by retrovirus recombinant vector", PNAS 7151-7155 (1984).

Top et al., "Immunization with Live Types 7 and 4 Adenovirus Vaccines", Journal of Infectious Diseases, 124:148-154 (1971).

Wagner et al., Microinjection of a rabbit β-globin gene into zygotes and its subsequent expression in adult mice and their offspring , PNAS 78:6376-80 (1981).

Wagner et al., "The human β-globin gene and a functional viral thymidine kinase gene in developing mice", PNAS 78:5016-5020 (1981).

Hoffman, R.M. Visualization of GFP-expressing Tumors and Metastasis in vivo, *Biotechniques*, May 2001, Abstract.

Chudakov et al., Use of Green Fluorescent Protein (GFP) and its Homologs for in vivo Protein Motility Studies, *Biochemistry* Sep. 2003, Abstract.

Chen et al., Molecular Brightness Characterization of EGFP in vivo by Fluorescence Fluctuation Spectroscopy, *Biophysical Journal*, Jan. 2002, vol. 82, pp. 133-144.

U.S. Appl. No. 10/188,184, filed May 1, 2003, Ferguson.

U.S. Appl. No. 11/543,164, filed Oct. 5, 2006, Vazquez-Martinez et al.

U.S. Appl. No. 11/812,812, filed May 21, 2007, Coen et al.

U.S. Appl. No. 11/898,789, filed Sep. 14, 2007, Roux et al.

U.S. Appl. No. 09/915,467, filed Jan. 2, 2003, Coen et al.

U.S. Appl. No. 12/623,776, filed Nov. 23, 2009, Roux et al.

Bartheld, C. S. von, et al., "Anterograde Axonal Transport, Transcytosis, and Recycling of Neurotrophic Factors", Mol. Neruobiol. 24:1-28 (2001).

Bordet, et al., Mol. Cell. Neurosci., vol. 17, pp. 842-854 (2001).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J of Cell Bio. 111:2129-2138, (1990).

Fishman et al., "Protein Delivery to Neurons Tetanus Toxin Compared to its Ganglioside Binding Fragment (Fragment C)", Society for Neuroscience Abstracts, vol. 22, pp. 1705 (1996).

Halpern and Loftus, "Characterization of the Receptor-binding Domain of Tetanus Toxin", J. Biol. Chem., vol. 268, pp. 11188-11192 (1993).

Halpern, et al., "Cloning and expression of functional fragment C of tetanus toxin," J. Infect. Immun.., vol. 58, pp. 1004-1009 (1990).

International Search Report for PCT/EP2004/010991, dated Aug. 23, 2005.

International Search Report for PCT/EP98/05113, dated May 26, 1999.

Lalli, et al. J. Cell Biol. vol. 156, pp. 233-239 (2002).

Mainen et al., "Two-photon Imaging in living brain slices," Methods, 18: 231-39 (1999).

Miana-Mena et al., "Neuronal activity-dependent membrane traffic at the neuromuscular junction," Proc. Natl. Acad. Sci. 99: 3234-39 (2002).

Pawson et al., "Assembly of Cell Regulatory Systems Through Protein Interaction Domains",, Science 300:445-452. (2003).

Poo, M. "Neurotrophins as synaptic modulators," Nature Reviews 2: 24-32 (2001).

Shimamura et al. BBRC 300: 464-71 (2003).

Stoop et al., "Synaptic modulation by neurotrophic factors: differential and synergistic effects of brain-derived neurotrophic factor and ciliary neurotrophic factor," Journal of Neuroscience 16: 3256-64 (1996).

Copending U.S. Appl. No. 11/898,789, filed Sep. 14, 2007.

Copending U.S. Appl. No. 11/543,164, filed Oct. 5, 2006.

Copending U.S. Appl. No. 11/375,093, filed Dec. 7, 2006.

Advisory Action mailed in U.S. Appl. No. 09/501,787 by M. T. Brannock on Aug. 16, 2006.

Advisory Action mailed in U.S. Appl. No. 09/501,787 by M. T. Brannock on Feb. 7, 2003.

Office Action mailed in U.S. Appl. No. 09/501,787 by M. T. Brannock on Dec. 22, 2006.

Office Action mailed in U.S. Appl. No. 09/501,787 by M. T. Brannock on Jan. 12, 2006.

Office Action mailed in U.S. Appl. No. 09/501,787 by M. T. Brannock on Apr. 14, 2004.

Office Action mailed in U.S. Appl. No. 09/501,787 by M. T. Brannock on Jun. 18, 2002.

Office Action mailed in U.S. Appl. No. 09/501,787 by M. T. Brannock on Oct. 5, 2001.

Office Action mailed in U.S. Appl. No. 11/812,812 by S. Gucker on Jan. 8, 2010.

Advisory Action mailed in U.S. Appl. No. 09/816,467 on Jan. 8, 2007.

Advisory Action mailed in U.S. Appl. No. 09/816,467 on Feb. 27, 2004.

Advisory Action mailed in U.S. Appl. No. 09/816,467 on Oct. 20, 2003.

Office Action mailed in U.S. Appl. No. 09/816,467 on Aug. 28, 2006.

Office Action mailed in U.S. Appl. No. 09/816,467 on Jun. 4, 2003.

Office Action mailed in U.S. Appl. No. 09/816,467 on Mar. 21, 2007.

Office Action mailed in U.S. Appl. No. 09/816,467 on Dec. 29, 2005.

Office Action mailed in U.S. Appl. No. 09/816,467 on Dec. 18, 2002.

Advisory Action mailed in U.S. Appl. No. 10/662,808 on May 15, 2009.

Advisory Action mailed in U.S. Appl. No. 10/662,808 on Jun. 25, 2007.

Office Action mailed in U.S. Appl. No. 10/662,808 on Aug. 17, 2009.

Office Action mailed in U.S. Appl. No. 10/662,808 on Jan. 29, 2009.

Office Action mailed in U.S. Appl. No. 10/662,808 on Apr. 29, 2008.

Office Action mailed in U.S. Appl. No. 10/662,808 on Dec. 21, 2006.

Office Action mailed in U.S. Appl. No. 10/662,808 on Jun. 1, 2006.

Advisory Action mailed in U.S. Appl. No. 11/543,164 on Jan. 27, 2010.

Advisory Action mailed in U.S. Appl. No. 11/543,164 on Nov. 19, 2008.

Office Action mailed in U.S. Appl. No. 11/543,164 on Sep. 16, 2009.

Office Action mailed in U.S. Appl. No. 11/543,164 on Feb. 2, 2009.

Office Action mailed in U.S. Appl. No. 11/543,164 on May 6, 2008.

Advisory Action mailed in U.S. Appl. No. 11/375,093 on Jul. 21, 2008.

Office Action mailed in U.S. Appl. No. 11/375,093 on May 27, 2009.

Office Action mailed in U.S. Appl. No. 11/375,093 on Feb. 20, 2008.

Office Action mailed in U.S. Appl. No. 11/375,093 on May 29, 2007.

* cited by examiner

SK-TTC -> Genes

DNA sequence    1600 b.p.    ggaaacagctat ... gtcgttttacaa   linear

```
    1 ggaaacagctatgaccatgattacgccaagctcgaaattaaccctcactaaagggaacaaaagctggagctcggtacccg                          80
   81 ggccacc ATG GTT GAT AAT AAT GAA GAT ATT CCA TTT TCA TAT TCT AAA AAT CTG GAT TGT TGG        141
    1         M   V   D   N   N   E   D   I   P   F   S   Y   S   K   N   L   D   C   W         18
  142 GTT GAT AAT AAT GAT ATT ATA GAT GTT ATA TTA AAA AAG AGT ACA ATT TTA AAT TTA GAT                 201
   19  V   D   N   N   D   I   I   D   V   I   L   K   K   S   T   I   L   N   L   D             38
  202 ATT AAT AAT AAT GCT CAA TCA GAT ATA ATA AAT GGC AAA GCA ATA CAT TTA GTA AAC TAT GAA TCT CCA    261
   39  I   N   N   N   A   Q   S   D   I   I   N   G   K   A   I   H   L   V   N   Y   E   S   P   58
  262 GAT GCT CAA TTG GTG CCC GGA ATA AAT GCT ATG GAT ATT GAA TAT AAT GAT ATG TTT AAT TTT         321
   59  D   A   Q   L   V   P   G   I   N   A   M   D   I   E   Y   N   D   M   F   N   F         78
  322 TCT GAA GTT CAT GTG AAA GTA CCT AAA GTA TCT AGT CAT AGT CTA TCA GAT TCC GCG GGA GAA TCT     381
   79  S   E   V   H   V   K   V   P   K   V   S   S   H   S   L   S   D   S   A   G   E   S     98
  382 ACC GTT AGC TTT TGG TTG AGG GTT ATT ATA ATG AAA AAA CAT AAA TGG ACT TTA AAA TTT GGC         441
   99  T   V   S   F   W   L   R   V   I   I   M   K   K   H   K   W   T   L   K   F   G         118
  442 ACA AAT GAG TAT TCA CTT ATA ACT TTT AGG AAT AAC TTA CCT GAT AGA TTA TCT GCT AAT ATA         501
  119  T   N   E   Y   S   L   I   T   F   R   N   N   L   P   D   R   L   S   A   N   I         138
  502 TGG AGT GTA CAA ATA ACT ATT AAA GGT TTT AGG ACT ATT ACT AAT GAT TTA TAT TTG TAT GGA GAA     561
  139  W   S   V   Q   I   T   I   K   G   F   R   T   I   T   N   D   L   Y   L   Y   G   E     158
  562 GTT AGA CAA ATA ACT TTT ATT ACT AAT GAT TTA TAT TCT GCT ATT AGA GAG GAT AAT AAA             621
  159  V   R   Q   I   T   F   I   T   N   D   L   Y   S   A   I   R   E   D   N   K             178
  622 TGG GTT TTT ATA GGA GTA GCA GAA ATT ACT GGT TTA GGA GCT ATT AGA GAG GAT AAT AAT GGA        681
  179  W   V   F   I   G   V   A   E   I   T   G   L   G   A   I   L   Y   I   N   G             198
  682 GTA CTT ATG GGA AGT GCA GAA ATT ACT GGT TTA GGA GCT ATT AGA GAG GAT AAT AAT ATA            741
  199  V   L   M   G   S   A   E   I   T   G   L   G   A   I   R   E   D   N   N   I            218
```

FIG. 1A

| | | | | | | | | | | | | | | | | | | | | |
|---|---|---|---|---|---|---|---|---|---|---|---|---|---|---|---|---|---|---|---|---|
| 742 | ACA | TTA | AAA | CTA | GAT | AGA | TGT | AAT | AAT | CAA | TAC | GTT | TCT | ATT | GAT | AAA | TTT | AGG | | 801 |
| 219 | T | L | K | L | D | R | C | N | N | Q | Y | V | S | I | D | K | F | R | | 238 |
| 802 | ATA | TTT | TGC | AAA | GCA | TTA | AAT | CCA | AAA | ATT | GAG | AAC | TTA | TAC | ACA | AGT | TAT | TCT | | 861 |
| 239 | I | F | C | K | A | L | N | P | K | I | E | N | L | Y | T | S | Y | S | | 258 |
| 862 | ATA | ACC | TTT | TTA | AGA | GAC | TTC | TGG | GGA | AAC | CCT | TTA | CGA | TAT | GAT | ACA | GAA | TAT | | 921 |
| 259 | I | T | F | L | R | D | F | W | G | N | P | L | R | Y | D | T | E | Y | | 278 |
| 922 | ATA | CCA | GTA | GCT | TCT | AGT | TCT | AAA | GAT | GTT | CAA | TTG | AAA | AAT | ATA | ACA | GAT | TAT | | 981 |
| 279 | I | P | V | A | S | S | S | K | D | V | Q | L | K | N | I | T | D | Y | | 298 |
| 982 | TTG | ACA | AAT | GCG | CCA | TCG | TAT | ACT | AAC | GGA | AAA | TTG | TTA | CCT | AAT | ATA | TAT | AGA | | 1041 |
| 299 | L | T | N | A | P | S | Y | T | N | G | K | L | L | P | N | I | Y | R | | 318 |
| 1042 | AAT | GGA | CTA | AAA | TTT | GAT | GGA | AAT | GCC | TAT | ATA | AAA | TTA | TAT | GAA | ATA | TCT | GTT | | 1101 |
| 319 | N | G | L | K | F | D | G | N | A | Y | I | K | L | Y | E | I | S | V | | 338 |
| 1102 | AAA | TCA | GGT | GAT | TTT | ATT | CCT | ATA | AAA | TTA | TAT | GTA | TCA | CTT | GAT | AGA | ATT | CTA | | 1161 |
| 339 | K | S | G | D | F | I | P | I | K | L | Y | V | S | L | D | R | I | L | | 358 |
| 1162 | TAT | CCG | AAA | GAT | GGA | AAT | GCC | TTT | AAT | AAA | ATG | GAA | GCA | GTA | AAT | ATT | CTA | AAA | | 1221 |
| 359 | Y | P | K | D | G | N | A | F | N | K | M | E | A | V | N | I | L | K | | 378 |
| 1222 | GCC | CCA | GGT | ATC | CCT | CTT | TAT | AAA | TTA | TAT | GAT | GAT | CCA | AAT | AGG | GAT | ATT | TTA | | 1281 |
| 379 | A | P | G | I | P | L | Y | K | L | Y | D | D | P | N | R | D | I | L | | 398 |
| 1282 | TAT | TCT | GTA | CAA | CTT | AAA | TTA | AAA | TTA | TAT | GAT | CCA | AAT | GAT | ATT | TTA | ATT | GCA | | 1341 |
| 399 | Y | S | V | Q | L | K | L | K | L | Y | D | P | N | D | I | L | I | A | | 418 |
| 1342 | CAT | AAT | GGT | CAA | ATA | GGC | AAT | GAT | AAT | ATT | AAA | GAT | ATT | TTA | TGT | GAT | TGG | TAC | | 1401 |
| 419 | H | N | G | Q | I | G | N | D | N | I | K | D | I | L | C | D | W | Y | | 438 |
| 1402 | TTT | AAT | CAT | TTA | AAA | GAT | AAA | ATT | TTA | GGA | TGT | GAT | TGG | TAC | TTT | GTA | CCT | ACA | GAT | GAG | 1461 |
| 439 | F | N | H | L | K | D | K | I | L | G | C | D | W | Y | F | V | P | T | D | E | 458 |
| 1462 | GGA | TGG | ACA | AAT | GAT | TAA | acagattgatatgttcatgacatatgcccgggatcctctagagtcgacctcgaggg | | | | | | | | | | | | | | 1535 |
| 459 | G | W | T | N | D | * | (SEQ ID NO:2) | | | | | | | | | | | | | 464 |
| 1536 | gggccccggtacccaattcgccctatagtgagtcgtattacaattcactggccgtcgttttacaa | | | | | | | | | | | | | | | | | (SEQ ID NO:1) | | 1600 |

FIG. 1B

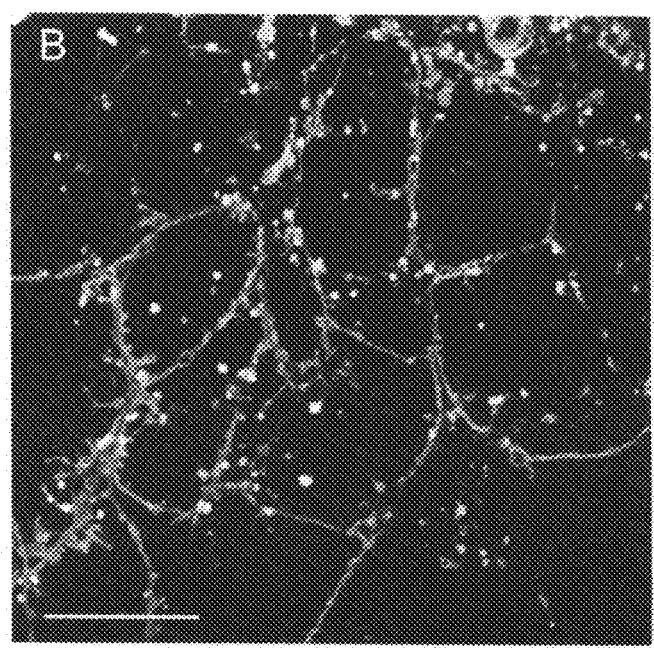
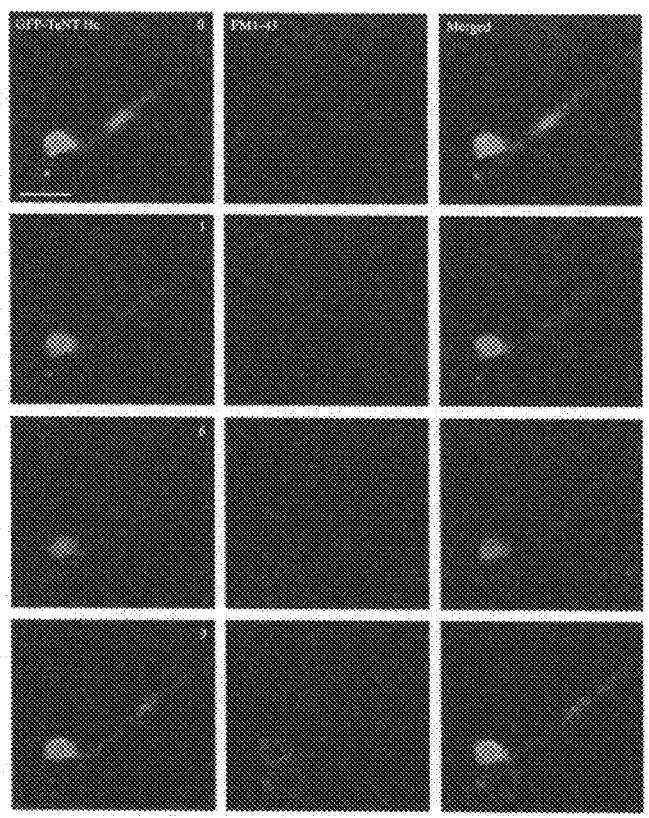
Figure 15 B-C

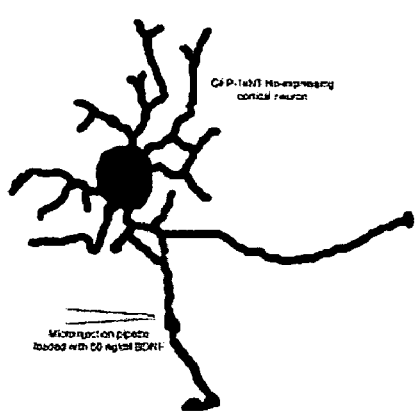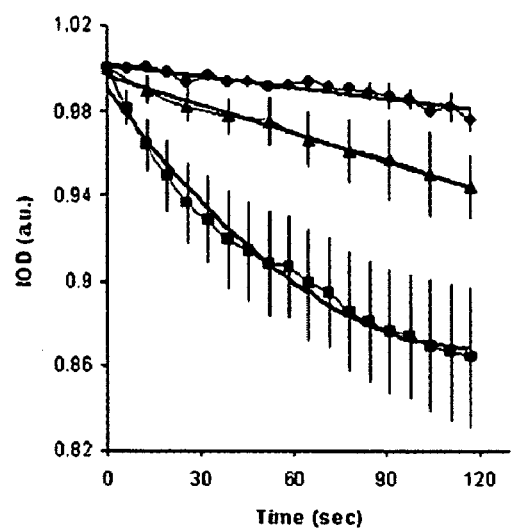
Figure 17

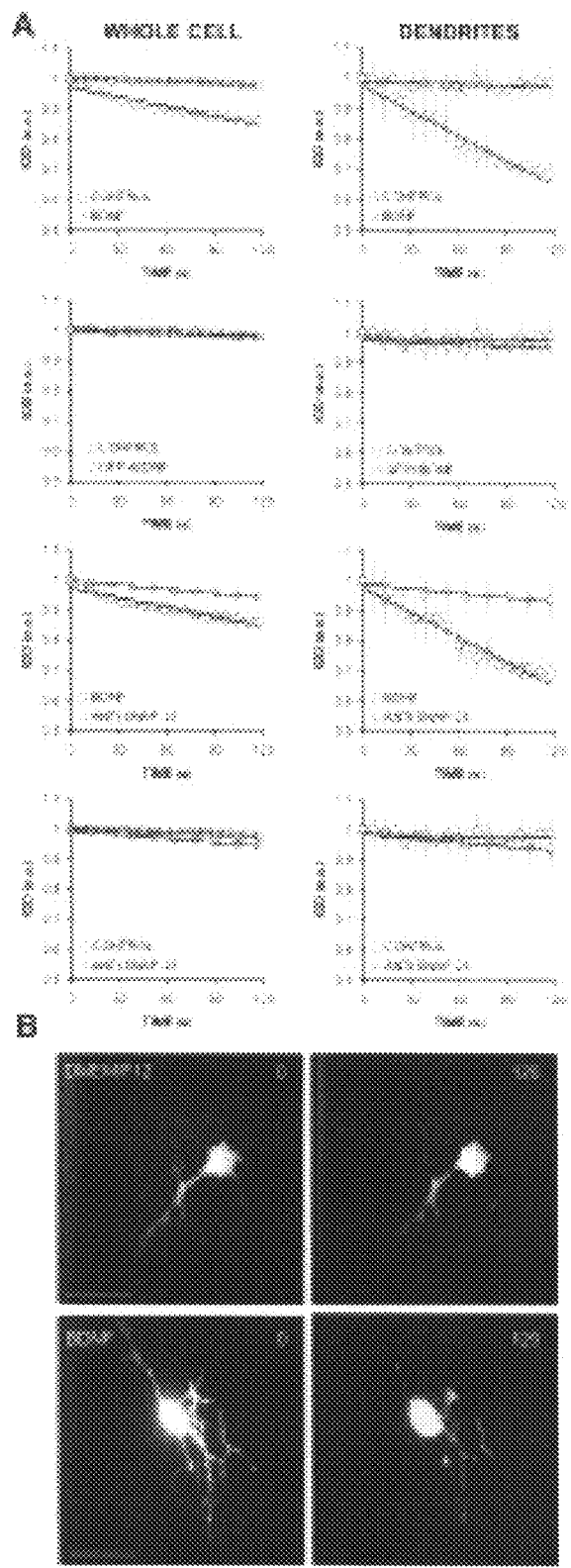
Figure 19 A-B

METHODS FOR DIRECT VISUALIZATION OF ACTIVE SYNAPSES

CROSS REFERENCE TO RELATED APPLICATIONS

The present application is a continuation-in-part of copending U.S. application Ser. No. 10/662,808 filed Sep. 16, 2003, which is a continuation-in-part of U.S. application Ser. No. 09/816,467, filed Mar. 26, 2001 now U.S. Pat. No. 7,435,792, which is a continuation of U.S. application Ser. No. 09/129,368, filed Aug. 5, 1998, now abandoned, which claims the benefit of Provisional Application No. 60/055,615, filed Aug. 14, 1997 and Provisional Application No. 60/065,236, filed Nov. 13, 1997. The entire disclosure of each of these applications is relied upon and incorporated by reference herein.

BACKGROUND OF THE INVENTION

This invention relates to the use of part of tetanus toxin for delivering a composition to the central nervous system of a human or animal. This invention also relates to a hybrid fragment of tetanus toxin, a polynucleotide that hybridizes with natural tetanus toxin, and a composition containing the tetanus toxin fragment as an active molecule. Further, this invention relates to a vector comprising a promoter and a nucleic acid sequence encoding the tetanus toxin fragment. In addition, this invention relates to methods of using the tetanus toxin fragment.

Tetanus toxin is produced by *Clostridium tetani* as an inactive, single, polypeptide chain of 150 kD composed of three 50 kD domains connected by protease-sensitive loops. The toxin is activated upon selective proteolytic cleavage, which generates two disulfide-linked chains: L (light, 50 kD) and H (heavy, 100 kD) [Montecucco C. and Schiavo G. Q. Rev. Biophys., (1995), 28: 423-472].

Evidence for the retrograde axonal transport of tetanus toxin to central nervous system (CNS) has been described by Erdmann et al. [Naunyn Schmiedebergs Arch Phamacol., (1975), 290:357-373], Price et al. [Science, (1975), 188:945-94], and Stoeckel et al. [Brain Res., (1975), 99:1-16]. In each of these studies, radiolabeled toxin was found inside membrane bound vesicles. Another property was the transynaptic movement of tetanus toxin that was demonstrated first by autoradiographic localization of $^{125}$I-labeled tetanus toxin in spinal cord interneurons after injection into a muscle [Schwab and Thoenen, Brain Res., (1976), 105:218-227].

The structure of this tetanus toxin has been elucidated by Helting et al. [J. Biol. Chem., (1977), 252:187-193]. Papain cleaves the tetanus toxin in two fragments:

the C terminal part of the heavy chain, 451 amino acids, also called fragment C; and the other part contained the complementary portion called fragment B linked to the light chain (fragment A) via a disulfide bond.

European Patent No. EP 0 030 496 B1 showed the retrograde transport of a fragment B-II$_b$ to the CNS and was detected after injection in the median muscle of the eye in primary and second order neurons. This fragment may consist of "isofragments" obtained by clostridial proteolysis. Later, this fragment B-II$_b$ was demonstrated to be identical to fragment C obtained by papain digestion by Eisel et al. [EMBO J., 1986, 5:2495-2502].

This EP patent also demonstrated the retrograde transport of a conjugate consisting of a I$_{bc}$ tetanus toxin fragment coupled by a disulfide bond to B-II$_b$ from axonal endings within the muscle to the motoneuronal perikarya and pericellular spaces. (The I$_{bc}$ fragment corresponds to the other part obtained by papain digestion as described above by Helting et al.). There is no evidence that this conjugate was found in second order neurons. The authors indicated that a conjugate consisting of the fragment B-II$_b$ coupled by a disulfide bond to a therapeutic agent was capable of specific fixation to gangliosides and synaptic membranes. No result showed any retrograde axonal transport or a transynaptic transport for such conjugate.

Another European Patent, No. EP 0 057 140 B1, showed equally the retrograde transport of a fragment II$_c$ to the CNS. As in the European Patent No. EP 0 030 496 B1, the authors indicated that a conjugate consisting of the fragment II$_c$ and a therapeutic agent was capable of specific fixation, but no result illustrated such allegation. This fragment II$_c$ corresponds to the now called fragment C obtained by papain digestion.

Francis et al. [J. Biol. Chem., (1995), 270(25):15434-15442] led an in vitro study showing the internalization by neurons of hybrid between SOD-1 (Cu Zn superoxide dismutase) and a recombinant C tetanus toxin fragment by genetic recombination. This recombinant C tetanus toxin fragment was obtained from Halpern group. (See ref. 11).

Moreover, Kuypers H. G. J. M and Ugolini G. [TINS, (1990), 13(2):71-75] indicated in their publication concerning viruses as transneuronal tracers that, despite the fact that tetanus toxin fragment binds to specific receptors on neuronal membranes, transneuronal labeling is relatively weak and can be detected only in some of the synaptically connected neurons.

Notwithstanding these advances in the art, there still exists a need for methods for delivering compositions into the human or animal central nervous system. There also exists a need in the art for biological agents that can achieve this result.

Additionally, activity-dependent modification of neuronal connectivity and synaptic plasticity play an important role in the development and function of the nervous system. Recently, much effort has been dedicated to following such modifications by the engineering of new optically detectable genetic tools. For example, fused to a reporter gene such as LacZ or GFP (Green Fluorescent Protein), the atoxic C-terminal fragment of tetanus toxin (or TTC fragment) can traffic retrogradely and transsynaptically inside a restricted neural network either after direct injection of the hybrid protein (Coen et al., 1997), or when expressed as a transgene in mice (Maskos et al., 2002). The dynamics of βgal-TTC clustering at the neuromuscular junction (NMJ) is strongly dependent on a presynaptic neuronal activity and probably involves fast endocytic pathways (Miana-Mena et al., 2002). Neuronal activity may induce this clustering and internalization at the NMJ by enhancing the secretion and/or action of various molecules at the synapse.

Over the past decade, various data indicate that neurotrophins, a family of structurally and functionally related proteins, including NGF (Nerve Growth Factor); BDNF (Brain Derived Neurotrophic Factor); Neurotrophin 3 (NT-3) and Neurotrophin 4 (NT-4), not only promote neuronal survival and morphological differentiation, but also can acutely modify synaptic transmission and connectivity in central synapses, thus providing a connection between neuronal activity and synaptic plasticity (McAllister et al., 1999; Poo, 2001; Tao and Poo, 2001). The role of these factors in neurotransmission between motoneurons and skeletal muscle cells has been studied using *Xenopus* nerve-muscle co-culture studies, whereby the treatment of these cultures with exogenous BDNF, NT-3 or NT4 leads to an increase of synaptic transmission by enhancing neurotransmitter secretion (Lohof et al., 1993; Stoop and Poo, 1996; Wang and Poo, 1997). Moreover, the muscular expression of NT-3 and NT-4 (Funakoshi et al., 1995; Xie et al., 1997), as well as NT-4 secretion (Wang and Poo, 1997) are regulated by electrical activity. This family of proteins thus provides a molecular link between electrical neuronal activity and synaptic changes.

The cellular actions of neurotrophins are mediated by two types of receptors: the $p75^{NTR}$ receptor, mainly expressed during early neuronal development, and a Trk tyrosine kinase receptor (Bothwell, 1995). The interaction of neurotrophins with Trk receptors is specific. TrkB and TrkC, are activated by BDNF/NT-4 and NT-3, respectively, and are expressed by motor neurons. TrkA, which is expressed by sensory neurons, is activated by NGF. Recently, evidence for a co-trafficking between TTC and the neurotrophin receptor $p75^{NTR}$ has been reported in cultured motoneurons (Lalli and Schiavo, 2002), as well as the activation by tetanus toxin and the TTC fragment of intracellular pathways involving Trk receptors in cultured cortical neurons (Gil et al., 2003).

Notwithstanding the knowledge in the art, there still exists a need for understanding the influences of neurotrophins and other neurotrophic factors on TTC traffic at the NMJ in vivo and for developing methods of using these neurotrophins and neurotrophic factors, and agonists or antagonists thereof, to modulate the neuronal transport of a tetanus toxin or a fusion protein comprising a fragment C of the tetanus toxin.

To date, active synapses have often been characterized by their electrical properties using electrophysiological recordings of patched neurons. Thus, depending on the electrical response of cells to different solutions, it has been possible to study indirectly active synapses and the activity of membrane receptors specific of presynaptic or postsynaptic endings. However, direct visualization of active synapses in complex neuronal networks has been elusive to date because of the lack of biological markers being specifically addressed and/or accumulated in these neuronal structures.

The recent development of styryl dyes has revolutionized the way in which functional synapses can be studied, inasmuch as they are excellent reagents both for identifying actively firing neurons and for investigating the mechanisms of activity-dependent vesicle cycling in a broad list of species. Thus, in a neuron that is actively releasing neurotransmitters, these dyes become internalized within the recycled synaptic vesicles and the nerve terminals become brightly stained (Cochilla, 1999). Nevertheless, the non-proteic nature of these molecules and the transient labeling that they provide represent difficult caveats when trying to study long-term synaptic activity and remodeling. Moreover, staining of more physiological relevant networks such as those presented in brain slices or intact animals with styryl dyes has been proven to be arduous, requiring the reduction of nonspecific background fluorescence while preserving the specific fluorescent signal by adding sulforhodamine or other fluorescent quenching reagents (Pyle, 1999).

SUMMARY OF THE INVENTION

This invention aids in fulfilling these needs in the art. More particularly, this invention provides a method for visualizing an active synapse wherein said method comprises: (a) exposing cells forming said active synapse to a biomarker comprising at least fragment C of tetanus toxin and a reporter protein; and (b) visualizing the biomarker; wherein the accumulation of the biomarker into dendritic spines of the cells allows visualization of an active synapse. Preferably, the cells are capable of expressing the biomarker to which they are exposed.

One embodiment of the invention comprises a preliminary step of transfecting the cell with a nucleic acid sequence capable of expressing in the cells the biomarker to which the cells are exposed in step (a).

In one embodiment, the biomarker is the fusion protein GFP-TTC.

The method of the invention can be an in vivo method. In the in vivo method, the cells can be cells of a non-human transgenic animal.

The method of the invention is especially suitable for visualizing neuronal networks.

This invention also provides a method for screening molecules capable of modulating synapse activity. The method comprises (a) exposing cells forming an active synapse to a biomarker comprising at least fragment C of tetanus toxin and a reporter protein; and (b) visualizing the biomarker; wherein the accumulation of the biomarker into dendritic spines of the cells allows visualization of an active synapse; wherein the cells are further exposed to the molecules to be screened in step (a), and wherein a modulation of the content of the biomarker into dendritic spines of the cells is indicative of a molecule capable of modulating synapse activity.

The terms "modulate" or "modulating" refer to the capability of a compound acting as either an agonist or an antagonist of certain reaction or activity. These terms, therefore, encompass the term "increase" and "decrease". The term "increase", for example, refers to an increase in the synapse activity as visualized by the method of the invention, for instance. Analogously, the term "decrease", for example, refers to a decrease in the synapse activity as visualized by the method of the invention, for instance.

Further, this invention provides a method for the early diagnosis of neurodegenerative diseases, wherein the method comprises: (a) exposing cells forming the active synapse to a biomarker comprising at least fragment C of tetanus toxin and a reporter protein; and (b) visualizing the biomarker; and wherein the accumulation of the biomarker into dendritic spines of the cells allows visualization of an active synapse; and wherein the cells are of a patient suspected of neurodegenerative disease.

In this method, an altered accumulation of the biomarker into dendritic spines compared with an accumulation of the biomarker into dendritic spines of a healthy patient allows early diagnosis of a neurodegenerative disease.

This invention provides a kit for the early diagnosis of neurodegenerative disease, wherein the kit comprises a biomarker comprising at least fragment C of tetanus toxin and a report protein.

Further, this invention provides a method for detecting anterograde transport of a biomarker. The method comprises providing dissociated cortical cells comprising cortical neurons containing a biomarker, and detecting anterograde transport of the biomarker by loss of the biomarker from the cortical neurons. It is possible to detect transport of the biomarker from post-synaptic to pre-synaptic neurons using this method.

This invention utilizes a method for in vivo delivery of desired composition into the central nervous system (CNS) of the mammal, wherein the composition comprises a non-toxic proteolytic fragment of tetanus toxin (TT) in association with at least a molecule having a biological function. The composition is capable of in vivo retrograde transport and transynaptic transport into the CNS and of being delivered to different areas of the CNS.

This invention provides a hybrid fragment of tetanus toxin comprising fragment C and fragment B or a fraction thereof of at least 11 amino acid residues or a hybrid fragment of tetanus toxin comprising fragment C and fragment B or a fraction thereof of at least 11 amino acid residues and a fraction of fragment A devoid of its toxic activity corresponding to the proteolytic domain having a Zinc-binding motif located in the central part of the chain between the amino acids 225 and 245, capable of transferring in vivo a protein, a peptide, or a polynucleotide through a neuromuscular junction and at least one synapse.

The protein having biological function can be a reporter protein. Additionally, the reporter protein linked to TTC can be any bioluminescent protein, such as GFP, RFP (Red Fluorescent Protein), DsRed (and variants), HcRed, CFP (and variants), YFP (and variants), the fusion protein Aequorin-GFP (with or without a linker), etc.

In addition, this invention provides a method of modulating the transport in a neuron of a tetanus toxin or a fusion protein comprising a fragment C of the tetanus toxin, wherein the method comprises administering to the neuron a neurotrophic factor in an amount sufficient to modulate the neuronal transport of the tetanus toxin or the fusion protein. In one embodiment, this method is carried-out in vitro, and in another embodiment in vivo.

Further, this invention provides a composition comprising an active molecule in association with the hybrid fragment of tetanus toxin (TT) or a variant thereof. The composition is useful for the treatment of a patient or an animal affected with CNS disease, which comprises delivering a composition of the invention to the patient or animal. In addition, the composition of this invention may be useful to elicit a immune response in the patient or animal affected with CNS, which comprises delivering a composition of the invention to the patient or animal.

Moreover, this invention provides polynucleotide variant fragments capable of hybridizing under stringent conditions with the natural tetanus toxin sequence. The stringent conditions are for example as follows: at 42° C. for 4 to 6 hours in the presence of 6×SSC buffer, 1×Denhardt's Solution, 1% SDS, and 250 µg/ml of tRNA. (1×SSC corresponds to 0.15 M NaCl and 0.05 M sodium citrate; 1×Denhardt's solution corresponds to 0.02% Ficoll, 0.02% polyvinyl pyrrolidone and 0.02% bovine serum albumin). The two wash steps are performed at room temperature in the presence of 0.1×SCC and 0.1% SDS.

A polynucleotide variant fragment means a polynucleotide encoding for a tetanus toxin sequence derived from the native tetanus toxin sequence and having the same properties of transport.

In addition, the invention provides a vector comprising a promoter capable of expression in muscle cells and optionally an enhancer, a nucleic acid sequence coding for the fragment of tetanus toxin of the invention or an amino acid variant fragment of the invention associated with a polynucleotide coding for a protein or a polypeptide of interest. In a preferred embodiment of the invention the promoter can be the CMV promoter and preferably the CMV promoter contained in pcDNA 3.1 (In Vitrogen, ref. V790-20), or the promoters actin as described in Bronson S. V. et al. (PNAS, 1996, 93:9067-9072).

In addition, the invention provides a vector comprising a promoter capable of expression in neuronal cells or in precursors (such NT2(hNT) precursor cells from Stratagene reference # 204101) and optionally an enhancer, a nucleic acid sequence coding for the fragment of tetanus toxin of the invention or an amino acid variant fragment of the invention associated with a polynucleotide coding for a protein or a polypeptide of interest. In a preferred embodiment of the invention the promoter can be β actin (see the above reference). These vectors are useful for the treatment of a patient or an animal infected with CNS disease comprising delivering the vector of the invention to the patient or animal. In addition, these vectors are useful for eliciting immune responses in the patient or animal.

One advantage of the present invention comprising the fragment of tetanus toxin (fragment A, B, and C) is to obtain a better transport of the fragment inside the organism compared with fragment C. Another advantage of the composition of the invention is to obtain a well defined amino acid sequence and not a multimeric composition. Thus, one can easily manipulate this composition in gene therapy.

In another embodiment, this invention provides a method of modulating the transport in a neuron of a neurotoxin, such as the tetanus toxin, or a fusion protein comprising a fragment C of the tetanus toxin. These methods comprise administering neurotrophic factors such as BDNF, NT-4, and GDNF, and agonists and antagonists thereof, to modulate internalization at a neuromuscular junction of a neurotoxin or a fusion protein comprising the TTC fragment according to the invention.

In one embodiment, these methods further comprise administering to the neuron a TrkB receptor agonist or a TrkB receptor antagonist in an amount sufficient to modulate the neuronal transport of the tetanus toxin or the fusion protein. The term "modulate" and its cognates refer to the capability of a compound acting as either an agonist or an antagonist of a certain reaction or activity. The term modulate, therefore, encompasses the terms "increase" and "decrease." The term "increase," for example, refers to an increase in the neuronal transport of a polypeptide in the presence of a modulatory compound, relative to the transport of the polypeptide in the absence of the same compound. Analogously, the term "decrease" refers to a decrease in the the neuronal transport of a polypeptide in the presence of a modulatory compound, relative to the transport of the polypeptide in the absence of the same compound. The neuronal transport of polypeptides can be measured as described herein or by techniques generally known in the art.

The TrkB receptor agonists include neurotrophic factors that activate a TrkB receptor, such as a Brain Derived Neurotrophic Factor or a Neurotrophin 4. The TrkB receptor agonists can also include antibodies that bind to TrkB receptors and activate them. These methods of using TrkB receptor agonists provide useful methods for enhancing the neuronal transport of a tetanus toxin or a tetanus toxin fusion protein.

The TrkB receptor antagonists include antibodies that bind to a TrkB receptor agonist, such as those described above, and thereby decrease the activation of a TrkB receptor. For example, these antibodies can be directed to neurotrophic factors that activate a TrkB receptor, such as a Brain Derived Neurotrophic Factor or a Neurotrophin 4. In addition, TrkB receptor antagonists include antibodies that bind to TrkB receptors and inactivate them. These methods of using TrkB receptor agonists provide useful methods for decreasing or preventing the neuronal transport of a tetanus toxin or a tetanus toxin fusion protein.

In another embodiment, these methods further comprise administering to the neuron a GFRa/cRET receptor agonist or a GFRa/cRET receptor antagonist in an amount sufficient to modulate the neuronal transport of the tetanus toxin or the fusion protein.

The GFRa/cRET receptor agonists include neurotrophic factors that activate a GFRa/cRET receptor, such as a Glial-Derived Neurotrophic Factor. The GFRa/cRET receptor agonists can also include antibodies that bind to GFRa/cRET receptors and activate them. These methods of using GFRa/cRET receptor agonists provide useful methods for enhancing the neuronal transport of a tetanus toxin or a tetanus toxin fusion protein.

The GFRa/cRET receptor antagonists include antibodies that bind to a GFRa/cRET receptor agonist, such as those described above, and thereby decrease the activation of a GFRa/cRET receptor. For example, these antibodies can be directed to neurotrophic factors that activate a GFRa/cRET receptor, such as a Glial-Derived Neurotrophic Factor. In addition, GFRa/cRET receptor antagonists include antibodies that bind to GFRa/cRET receptors and inactivate them. These methods of using GFRa/cRET receptor agonists provide useful methods for decreasing or preventing the neuronal transport of a tetanus toxin or a tetanus toxin fusion protein. In these methods, the agonist or antagonist can be administered to neuronal cells that already contain a tetanus toxin or a fusion protein. Alternatively, the tetanus toxin or fusion protein can be administered concurrently with or after the administration of the agonist or antagonist.

In one embodiment, the TTC-containing fusion proteins of the present invention comprise a second protein that is encoded by a reporter gene, such as the lac Z gene or the Green Fluorescent Protein gene. Such fusion proteins are useful for visualizing modulation of the synaptic plasticity in vivo, including in a human, for example by magnetic resonance imaging. For example, the fusion proteins can be used to monitor and detect the effects of a compound, such as a neurotrophic factor, on neuronal transport. In these methods, the compound and the fusion protein are administered to a neuron, and the fusion protein is detected to determine the effect of the compound on the neuronal transport. In addition, the fusion proteins can be used to detect modifications in trafficking patterns and/or synapse activity within a restricted neural network, such as those used in known animal models for neurodegenerative diseases. The fusion proteins can also be used in screening methods to detect compounds that reduce or prevent neuronal transport of a tetanus toxin. Compounds so identified can be used to prevent or treat tetanus infections.

The TTC fragment can also be coupled to a neurotrophic factor and administered to a patient to treat CNS pathologies associated with production defects of different factors. The TTC fragment could also be used as a vector for modulating interactions with proteins involved in neurodegenerative diseases.

The present invention also provides compositions comprising a TrkB receptor agonist or a GFRa/cRET receptor agonist and a fusion protein comprising a fragment C of the tetanus toxin fused to a second protein. In one embodiment, the TrkB agonist is a neurotrophic factor such as a Brain Derivated Neurotrophic Factor or a Neurotrophin 4. In another embodiment, the GFRa/cRET receptor agonist is a neurotrophic factor, such as Glial-Derived Neurotrophic Factor

BRIEF DESCRIPTION OF THE DRAWINGS

The patent or application file contains at least one drawing executed in color. Copies of this patent or patent application publication with color drawings will be provided by the Office upon request and payment of the necessary fee.

This invention will be more fully described with reference to the drawings in which:

FIGS. 1A-1B shows the DNA sequence and amino acid sequence of the TTC fragment cloned in PBS:TTC.

(A) Two hours after the subcutanous injection of GFP-TTC in the vicinity of the LAL muscle, the probe (green) was concentrated at motor nerve endings of NMJ. Associated intramuscular motor axons were immunostained (red) with an antibody against NF200. GFP-TTC labeling was also detected in sensory nerve fibers (arrows) and at the nodes of Ranvier of myelinated axons (arrowheads). (B) Strong nodal labeling with GFP-TTC (green) (arrow) in a single living myelinated axon. Myelin was passively stained with RH414 dye (red). (C) Two hours after injection as in A, LAL muscle fibers were fixed and labeled for troponin T by indirect immunofluorescence. (C' and C") Inset is a side view image of a NMJ showing that GFP-TTC staining (green) is located presynaptically. (D-G) LAL was harvested at various times after GFP-TTC injection and NMJ identified in red by labeling with TRITC-a-BTX (D'-G'). D-D': 5 min; E-E' 30 min; F-F': 2 h and G-G': 24 h.

Scalebars: A, 20 µm; B, 8 µm; C: 20 µm; D, 2 µm; E-G, 5 µm.

Figure 7:
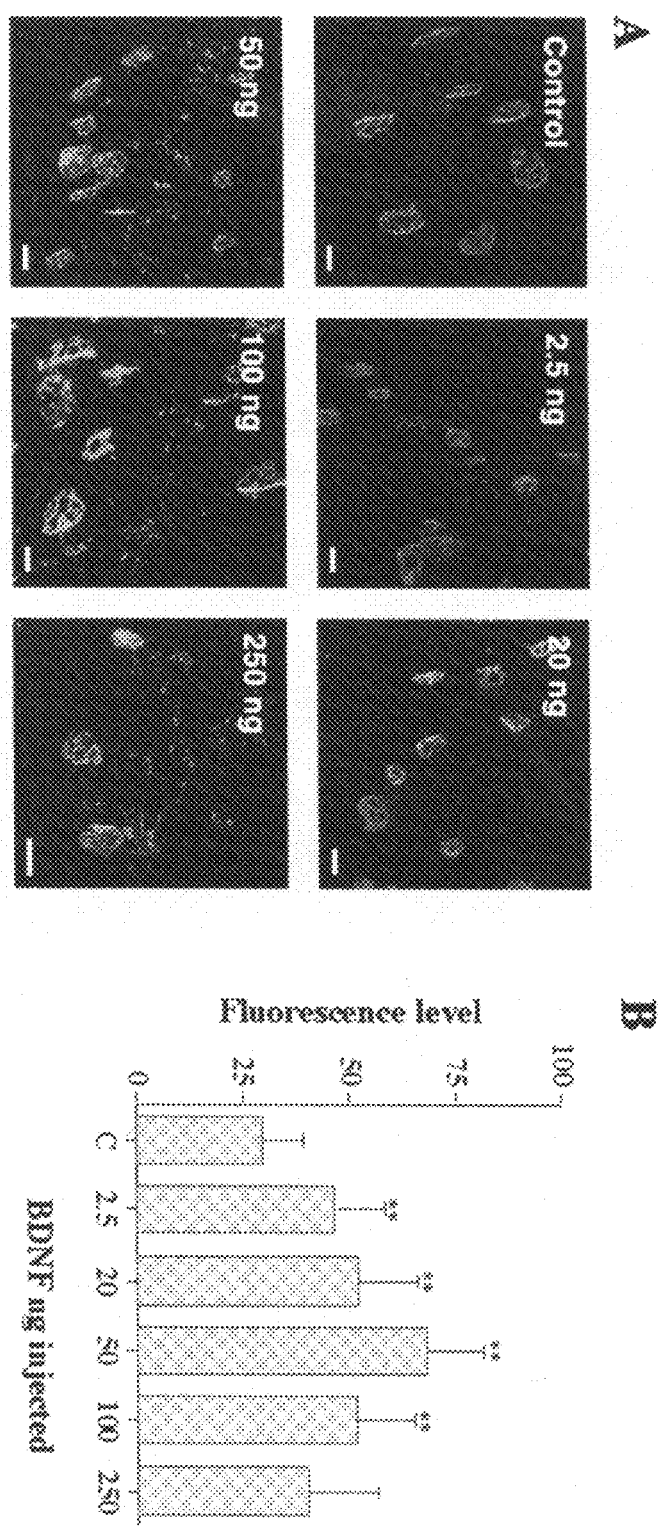

FIG. 7 shows that BDNF increases GFP-TTC recruitment at the NMJ in a dose-dependent manner.

(A) The NMJ on LAL muscles was identified by TRITC-a-BTX labeling 30 min after in vivo co-injection of GFP-TTC with various amounts of BDNF. The level of GFP fluorescence was quantified over these areas (see B). An enhancement of axonal labeling (arrows), more prononced with higher BDNF concentration, was also detected. Scale bars: 20 µm (B) Confocal sections of the NMJ were collected for analysis and projections generated. TRIT-a-BTX labeling determines the area of the NMJ over which the global GFP fluorescent signal was measured. For each, (n 15-20), the GFP fluorescence was divided by NMJ area (in µm$^2$) to obtain the fluorescence level. Error bars indicate S.D. ** $P<0.005$; t-test, vs control.

Figure 8:
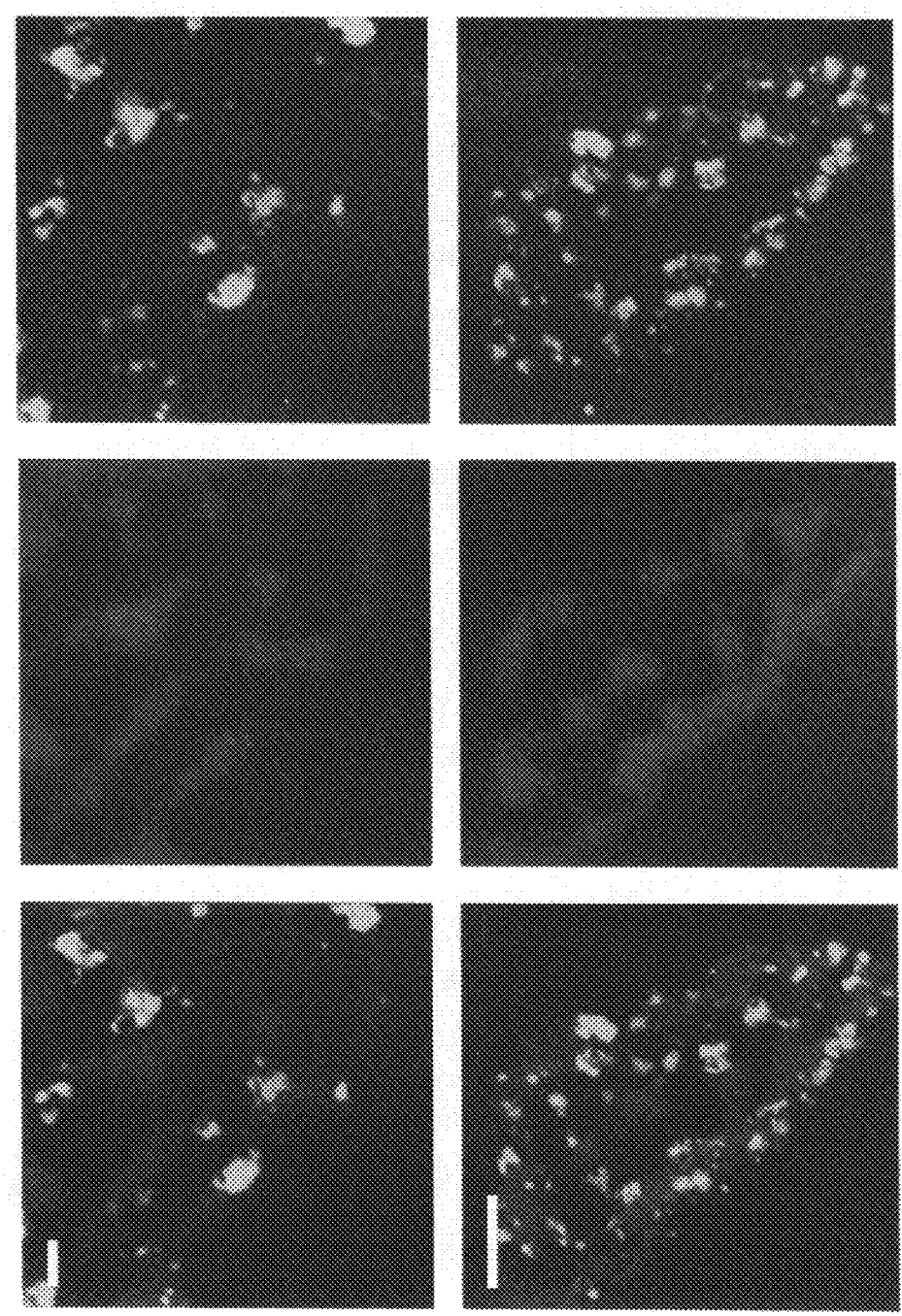

FIG. 8 depicts the immunofluorescence visualization of TrkB at the LAL NMJ. Two hours after GFP-TTC injection in LAL, confocal analysis was performed. The fusion protein was identified in green directly by GFP fluorescence. TrkB, identified (in red) by indirect immunofluorescence (see material and methods), was located at the NMJ. However, when the two projections were overlaid, no overlap was found between the TrkB and the GFP-TTC signals.

Scale bar: Top: 5 µm; Bottom: 2 µm

Figure 9:
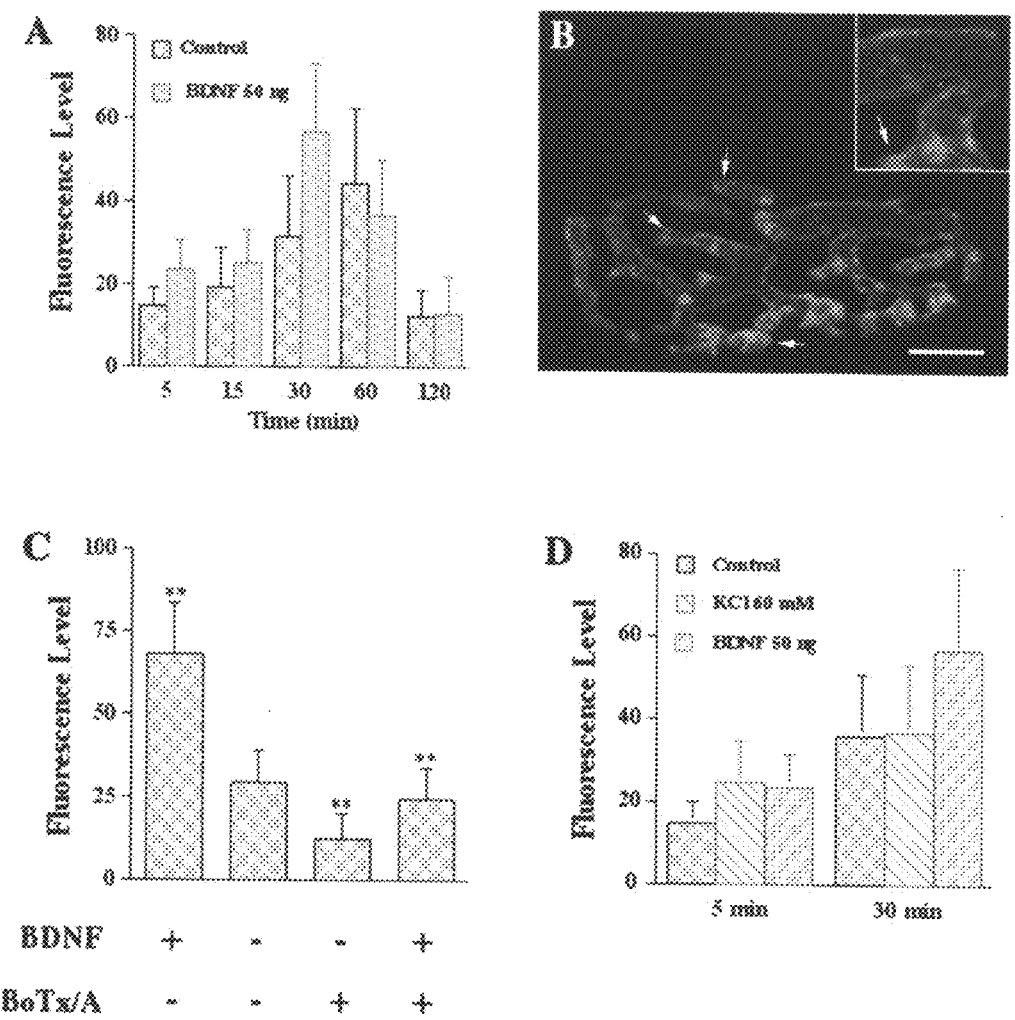

FIG. 9 represents the results of experiments elucidating the mechanisms of GFP-TTC recruitment to the NMJ.

(A) Quantification of GFP-TTC fluorescence was performed, as described in FIG. 7 at various time after co-injection with or without 50 ng BDNF.

(B) After in vitro loading for 45 min with GFP-TTC, the excised LAL muscle was fixed and SV2 protein detected by indirect immunofluorescence (red). SV2 labeling was mostly diffuse and concentrated in a few areas of the NMJ (arrows). Colocalization of SV2 with GFP-TTC staining was only observed in a very limited number of areas. Scale bar: 8 µm.

(C) Treatment with botulinum type-A neurotoxin to block synaptic vesicles exocytosis and endocytosis. 48 hours after BoTx/A injection (as described in material and methods), GFP-TTC, associated or not with 50 ng BDNF, was injected in LAL muscle and GFP fluorescence quantified as previously. ** $P<0.005$; t-test, vs control; * $P<0.005$; t-test vs BoTx/A treatment.

(D) Comparison of KCl induced depolarization and BDNF effects on GFP-TTC localization at the NMJ.

Figure 10:
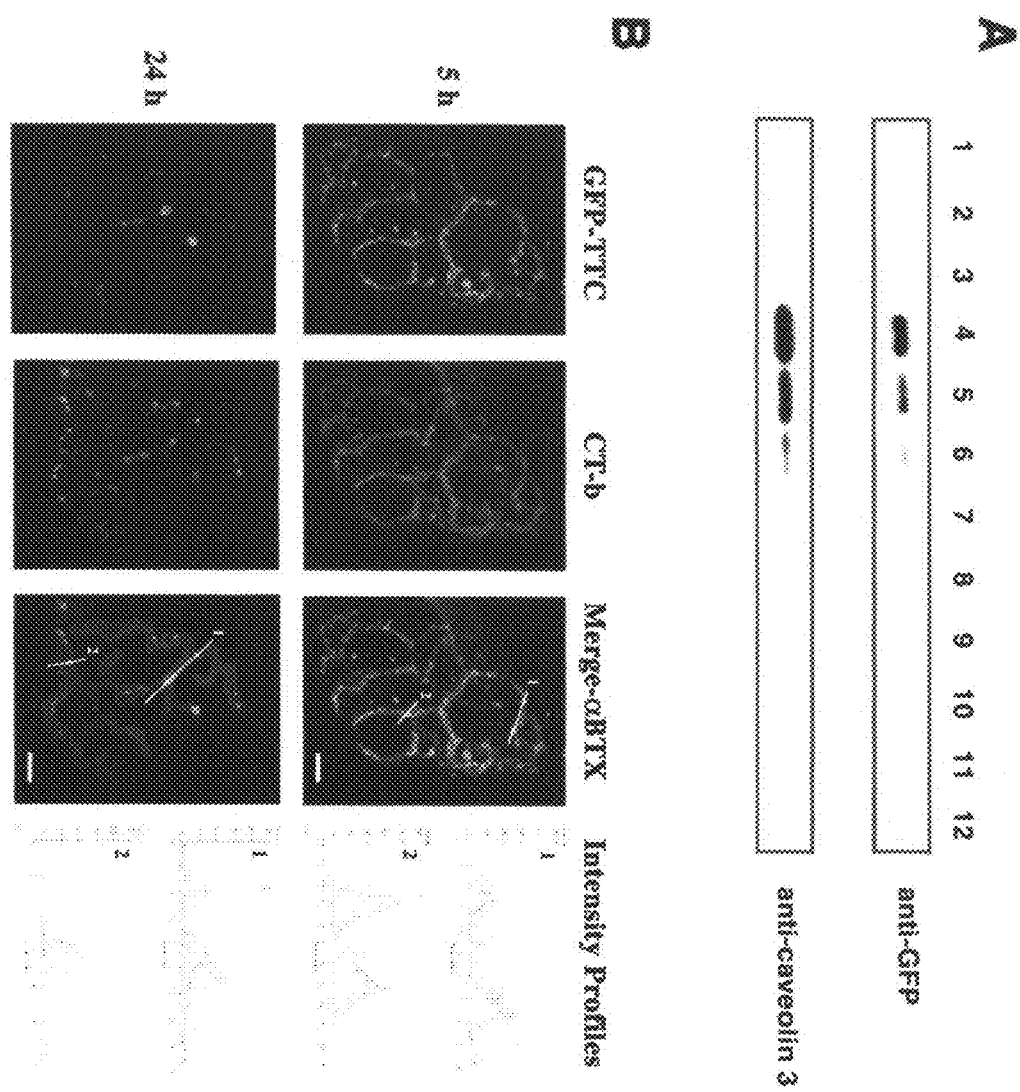

FIG. 10 depicts the localization of GFP-TTC probe in lipid microdomains.

(A) 2 hours after intramuscular injection, GFP-TTC was found in detergent resistant membranes (DRMs) (lanes 4-6) isolated from gastrocnemius muscle, which also contained the raft marker caveolin-3. A small amount of GFP-TTC was also detected in the soluble fraction (lane 12).

(B) GFP-TTC colocalized with the raft marker GM1 at the NMJ. NMJ were identified by Alexa 647-a-BTX binding (in blue). Whereas GFP-TTC was detected in less than 5 min at the NMJ, CT-b requires 3-5 hours. At this time, a diffuse staining which colocalized with the similar GFP-TTC labeling, was obtained, while a few patches labeling only for CT-b were also observed.

(C) Intensity profiles of GFP-TTC (green) and Alexa 594 labeled-CT-b (red) were performed 5 or 24 h after intramuscular co-injection of both probes in gastrocnemius.

Scale bar: 5 µm.

Figure 11:
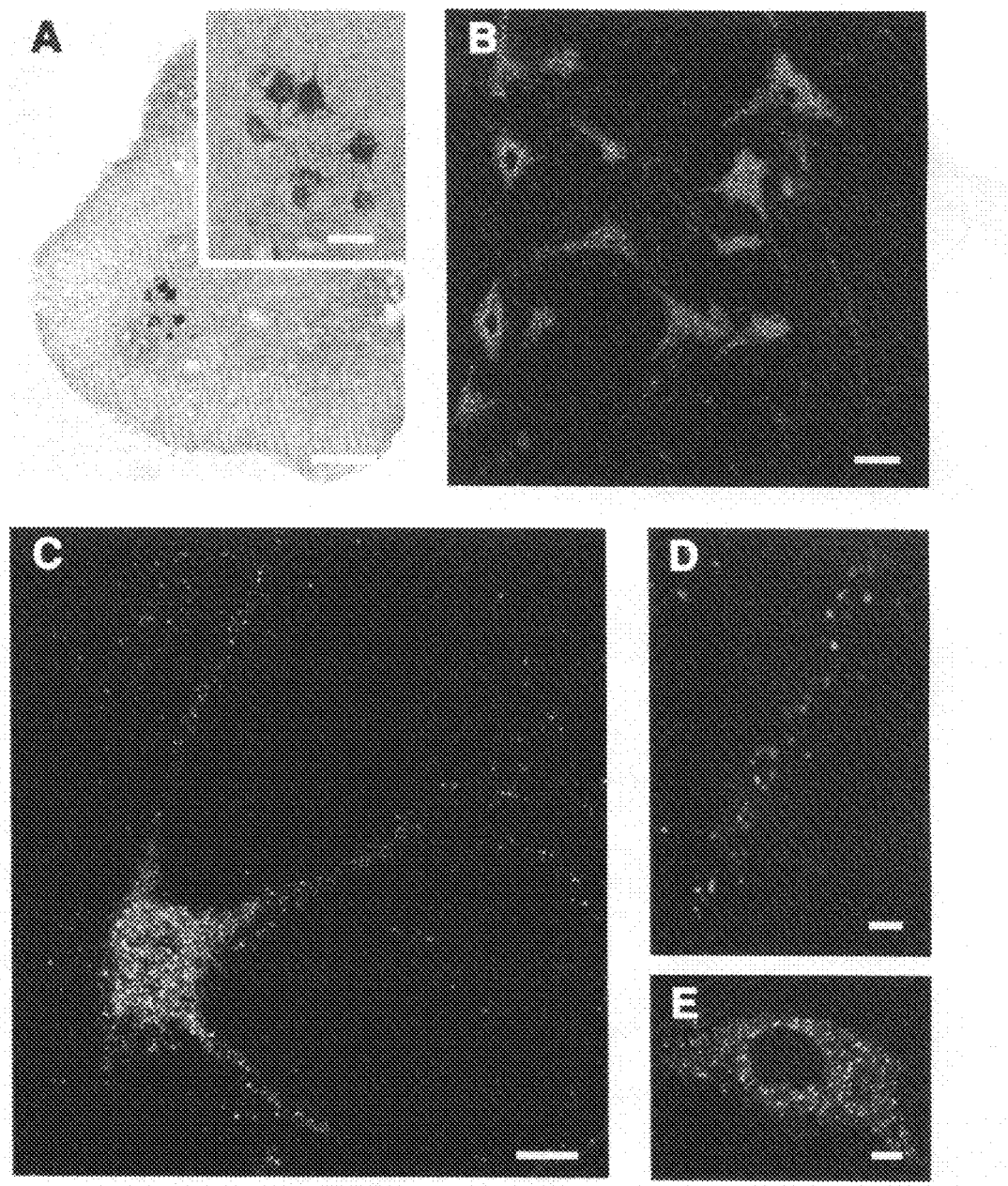

FIG. 11 shows a comparison of GFP-TTC and CT-b localization in motoneuron cell bodies. Twenty four hours after β-gal-TTC (A) or GFP-TTC and CT-b (B-E) intramuscular injection in gastrocnemius muscle, mice were perfused intracardially and their spinal cords removed. (A) X-gal reaction on spinal cord transerve sections showed labeling in motoneuron cell bodies but also in neurites (inset). (B) GFP-TTC and CT-b were detected on longitudinal section of spinal cord in a significant number of motoneurons. (C) Probes were detected in vesicles highly concentrated in cell bodies but also in neurites. (D) In neuronal extensions, GFP-TTC and CT-b were detected in different vesicular-like structures. Note that only few of them were positive for both probes. (E) Note that neither GFP-TTC nor CT-b were detected in the nucleus as shown in one optical section.

Scale bars: A, 0.2 mm; inset, 50 µm; B, 20 µm; C, 10 µm; D, 5 µm; E, 2 µm.

Figure 12:
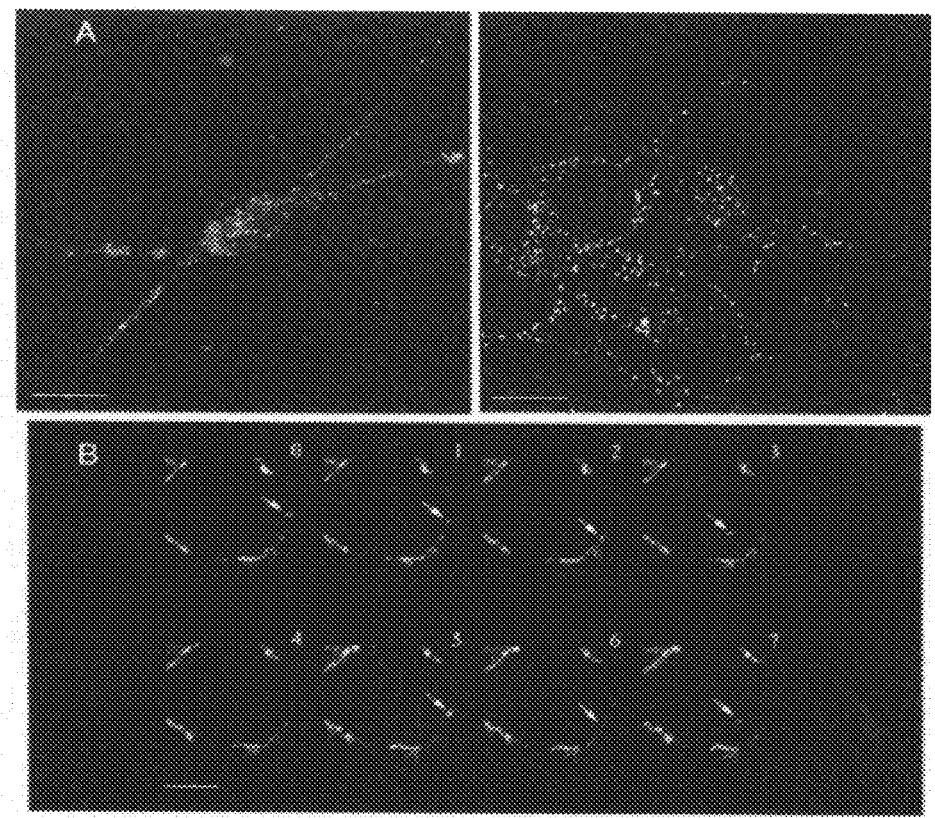

FIG. 12 shows membrane distribution and neuronal activity dependent mobilization of GFP-TTC in cortical cells:

(A) Two representative examples of membrane distribution of the hybrid protein in dissociated cortical cells are illustrated. On the left there is a 2D projection of a cortical cell previously incubated with 1.5 µg/ml GFP-TTC protein (scale bar: 20 µm). As shown, GFP-TTC binds to specific microdomains of the plasma membrane, likely due to an accumulation of its receptors in such regions. On the right there is another example of the distribution pattern of this marker in the membrane. This image shows only one confocal section (scale bar: 20 µm).

(B) This figure represents a time-lapse sequence (min) of a dissociated cortical cell exposed to 1.5 µg/ml GFP-TTC in the presence of 50 mM KCl (scale bar: 5 µm). As shown, membrane microdomains aggregating GFP-TTC are not static, but depending on the cellular activity, they move towards particular regions of the cell membrane where they are internalized in discrete endocytic events. This and all the following images were deconvolved offline by Huygens 2.4.4 (Scientific Imaging Volume, Hilverson, The Netherlands) in order to increase the signal/noise ratio.

Figure 13:
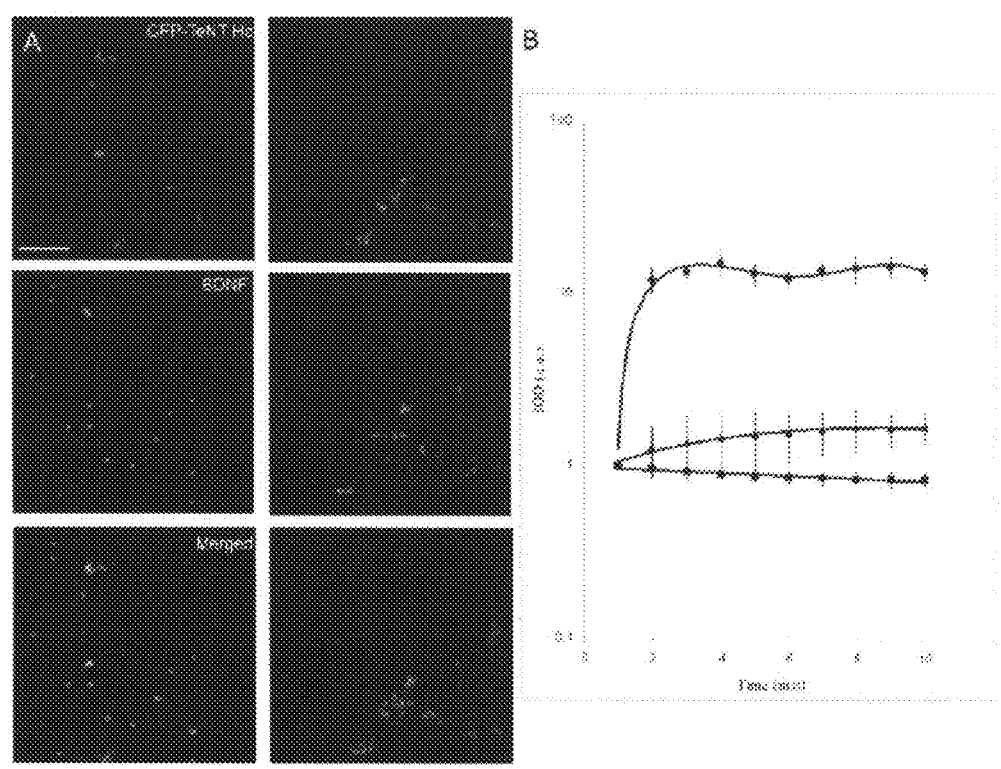

FIG. 13 shows the effect of BDNF in the recruitment of GFP-TTC enriched membrane microdomains and in their internalization within cortical neurons:

(A) This panel shows two examples of the distribution of GFP-TTC (top), BDNF receptors (middle), and the merged image (bottom) at the level of the plasma membrane. Cells were exposed to 1.5 µg/ml GFP-TTC and 50 ng/ml BDNF bound covalently to 500 nm fluorescent microspheres and immediately monitored with a Nipkow Disk confocal microscope. As shown, regions clustering GFP-TTC were often in membrane microdomains adjacent to those presenting BDNF receptors, confirming the existence of interactions among these receptors at the level of the membrane. Scale bar: left panels, 10 µm; right panels, 20 µm.

(B) Internalization kinetics of GFP-TTC within dissociated cortical cells in the absence or presence of BDNF. Whereas GFP recombinant protein did not internalize (■, n=5), GFP-TTC displayed a curve of internalization slow in basal conditions, as assessed by analyzing the level of intracellular fluorescence after incubation of cells with the hybrid protein (▲, n=4). However, during the combined incubation with GFP-TTC and 50 ng/ml BDNF, the internalization kinetics of the hybrid protein increased 10 fold in the first minute of treatment and stayed elevated as long as the experiment lasted (●, n=3). Data represent the average±SEM of the number of cells indicated in each treatment.

Figure 14:
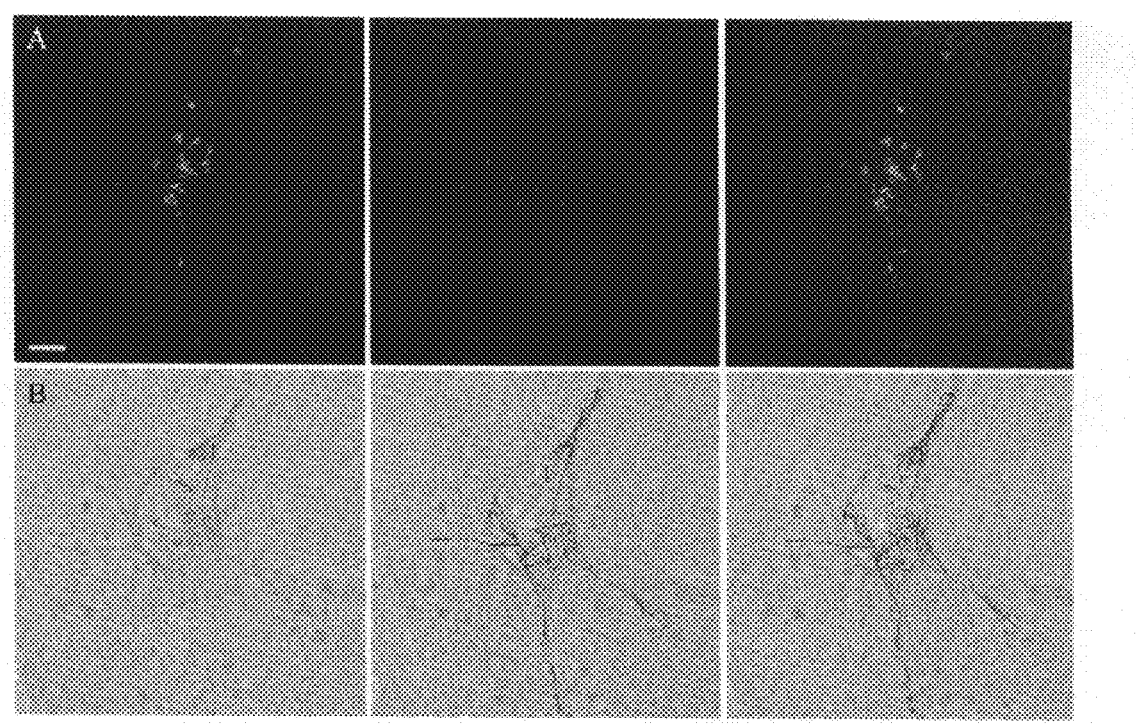

FIG. 14 depicts intracellular retrograde pathways followed by BDNF/receptor- and GFP-TTC-containing vesicles:

(A) This Figure shows a cortical cell incubated with GFP-TTC (left panel) and BDNF-coated fluorescent microspheres of 100 nm in diameter, small enough to be taken up within cells. After 12 h of incubation, the hybrid protein distributed intracellularly forming accumulations, thereby suggesting that GFP-TTC is internalized in intracellular transport vesicles within cortical cells. Moreover, it was observed that GFP-TTC clusters were often associated to BDNF/receptor carriers.

(B) Analysis of vesicle intracellular movement by a particle tracking algorithm developed for Image J (Jeffrey Kuhn, University of Texas). As illustrated, GFP-TTC-containing vesicles and BDNF/receptors-containing vesicles follow similar retrograde trafficking pathways from apical regions of neural processes to the cell soma. Scale bar: 10 µm.

FIG. 15 shows intracellular localization of:

(A) Confocal micrographs of dendritic spines from GFP-TTC-expressing neurons in culture (left panels) and in organotypic slices (right panels). Scale bars represent 5 µm in the first image and 2 µm in the others.

(B) Shown in this Figure is an example of FM143 staining in dendritic arborizations displayed by dissociated cortical cells. This lipophylic dye accumulates preferentially in membrane regions with a high exocytic/endocytic turnover. In this example, after 30 min of incubation the dye located predominantly in round protrusions presenting similar size and morphology that the regions accumulating GFP-TTC (scale bar: 50 µm).

(C) Time-course imaging of FM1-43 binding. The styryl dye binds preferentially to the membrane of presynaptic terminals located in physical proximity of postsynaptic spines accumulating GFP-TTC. Scale bar represents 2 µm.

(D) Quantification of the distribution of GFP or GFP-TTC hybrid proteins within cortical neurons. Data are normalized to the IOD calculated from 24 random dendritic shaft regions selected from 4 diferent cells. Data are expressed as average+SEM. $P<0.05$ vs. averaged IOD in shaft regions.

Figure 16:
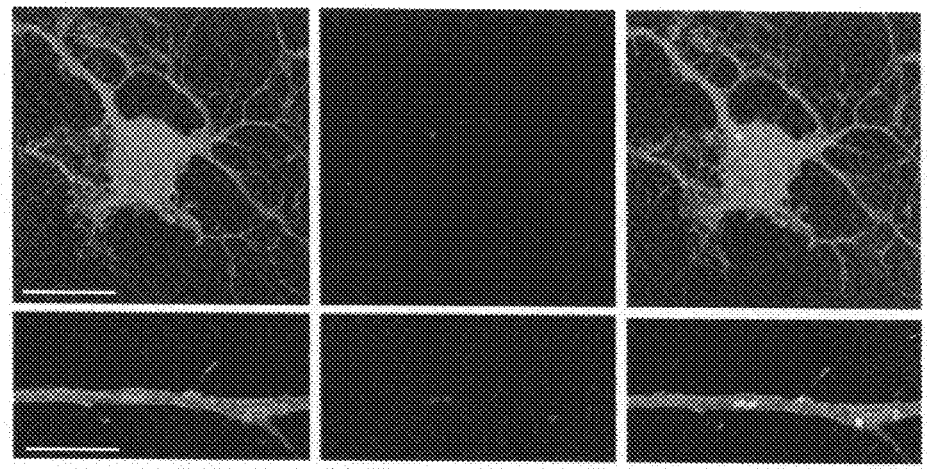

FIG. 16 depicts intracellular distribution of GFP-TTC and PSD-Zip45. Two representative examples of the intracellular distribution of GFP-TTC (left panels) and DsRed-PSD-Zip45 (middle panels) within dissociated cortical cells are shown. After 24-48 h of cotransfection with the constructs pCMV-GFP-TTC and pCMV-DsRed-PSD-Zip45, neurons were scanned and intracellular distribution of both proteins studied. At the level of the cell soma, GFP-TTC and DsRed-PSD-Zip45 were found to be highly colocalized (merged image). Although in a less extent, at the dendritic level both proteins also showed a high colocalization rate. Scale bars: top, 20 µm; bottom, 5 µm.

FIG. 17 shows the effect of BDNF on the exocytosis of GFP-TTC from dissociated cortical cells:

(A) Schematic representation of the methodology used for local administration of DMEM/F12 or 50 ng/ml BDNF. The microinjection pipette was placed in close proximity of GFP- or GFP-TTC-expressing cells, and its content was ejected continuously at a constant pressure of 40 Psi throughout the experiment. Intracellular fluorescence for each time point was calculated offline.

(B) Measurement of intracellular fluorescence after local treatment of dissociated cortical cells with DMEM/F12 (●; n=5) or 50 ng/ml BDNF (■; n=6). As shown, whereas culture medium induced a slow decay in intracellular fluorescence (estimated 50% decay ratio in 70 min) likely due to photobleaching effects, BDNF triggered a rapid loss of intracellular fluorescence (estimated 50% decay ratio in 10 min) that reached statistical difference as fast as 12 s after drug administration ($P<0.05$; Newman-Keuls Multiple Comparison test). To confirm that this decrease in intracellular GFP-TTC was actually caused by an increase exocytic turnover and not by protein degradation, GFP-TTC-expressing cells were microinjected with a monoclonal SNAP-25 neutralizing antibody prior to BDNF local administration (▲; n=6). Thus, after blockage of SNARE-dependent exocytosis, BDNF-induced effects on GFP-TTC intracellular levels were strongly reduced, but not completely inhibited.

Figure 18:
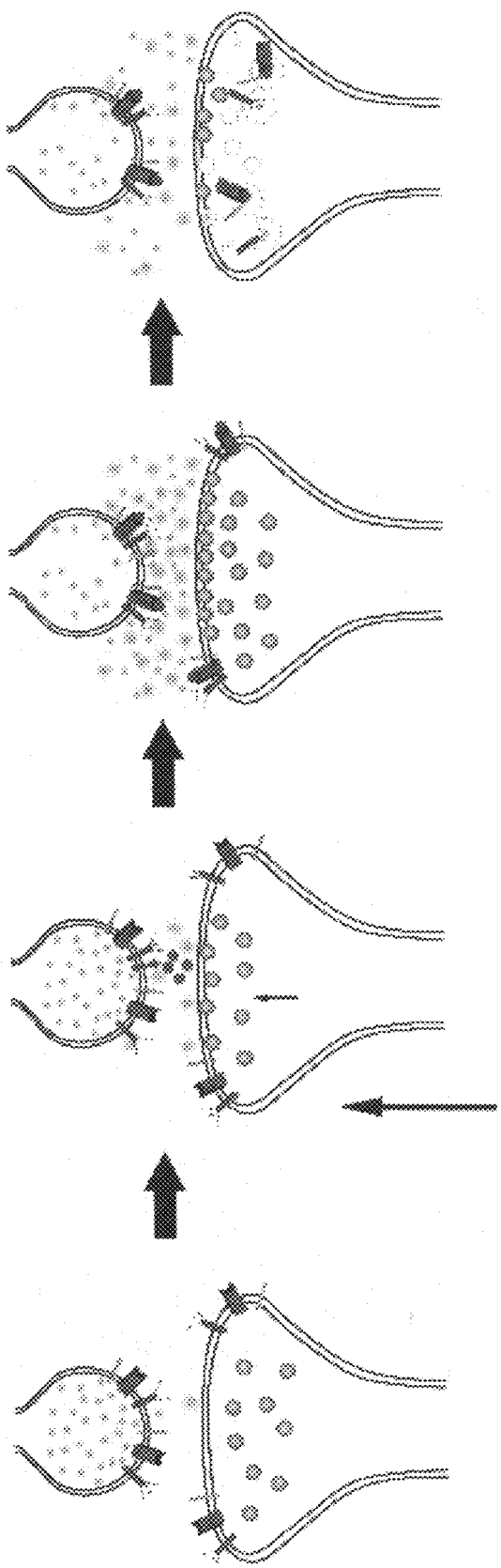

FIG. 18 is a schematic model of BDNF effect on membrane trafficking in the central synapse. Under basal conditions, presynaptic neurons would present a spontaneous activity that would trigger the release of few vesicles into the synaptic cleft, not in appropriate number to propagate the signal towards postsynaptic structures. Likewise, the postsynaptic cell would also display a spontaneous quantal release that would induce the release of small amounts of GFP-TTC. Upon depolarization of the presynaptic cell, a more important neurotransmitter release would be triggered, thereby transmitting the signal to postsynaptic specializations. Thus, stimulation of the postsynaptic neuron would induce secretion of BDNF into the synaptic cleft, which would bind to its receptors in the presynaptic as well as in the postsynaptic neuron. BDNF bound to its receptor complex in the presynaptic side would trigger a massive neurotransmitter release that would reinforce the presynaptic signal propagation. On the other hand, BDNF bound to its postsynaptic receptors would trigger release of neurotoxin, which would bind to the membrane gangliosides associated to BDNF-receptor complexes in both presynaptic and postsynaptic cells. After massive exocytosis in the presynaptic terminal, endocytosis follows and recycling of presynaptic membrane could bring in GFP-TTC/receptor complex, as well as the free extracellular probe.

FIG. 19 shows modulation of GPF-TTC release from postsynaptic processes.

(A) High-speed confocal imaging of intracellular fluorescence after local administration of DMEM/F12 (control conditions) or BDNF nearby dendritic processes of cultured neurons expressing GFP, GFP-TTC, or GFP-TTC previously microinjected with anti-SNAP-25. Data are normalized to the IOD calculated from the first time-point and intracellular fluorescence decay from whole cells (left panels) or randomly-selected regions from distal dendritic processes (right panels) assessed over time. All data are represented as averaged IOD±SEM of, at least, 5 different cells per experimental condition.

(B) Representative examples of GPF-TTC fluorescence loss in a neuron exposed to vehicle (top panels) and BDNF (bottom panels). Scale bar represents 50 μm.

DETAILED DESCRIPTION

It will be recalled that retrograde signaling from postsynaptic to the presynaptic neurons is essential for development, maintenance and activity-dependent modification of synaptic connections (Chao, 2003). This signaling involves neurotrophins, such as nerve growth factor (NGF), brain-derived neurotrophic factor (BDNF), and neurotrophins 3 and 4 (NT3 and NT4), which, in addition to their classical effects on neuronal cell survival, have also been shown to regulate axonal and dendritic growth, neurotransmitter release, long-term potentiation (LTP), and synaptic plasticity (McAllister et al., 1999; Poo, 2001). Neurotrophins are produced and released by the target cells, internalized by presynaptic terminals and retrogradely transported to the cell soma where they exert their effects (Ginty and Segal, 2002; Miller and Kaplan, 2001). In this scenario, it is worth to mention that expression and secretion of NGF and BDNF in central neurons is regulated by neuronal activity, inasmuch as these processes can be triggered by membrane depolarization (Blochl and Thoenen, 1995; Gall and Isackson, 1989; Goodman et al., 1996; Lu et al., 1991; Zafra et al., 1991).

A GFP-tagged biomarker has been developed that allows visualization of retrograde trafficking from the peripheral to the central nervous system, by utilizing the transport properties of the non-toxic fragment of tetanus toxin (TTC). Specifically, it was found that this marker, tagged with GFP or β-Gal, accumulates presynaptically at the neuromuscular junction (NMJ) in a neuronal activity-dependent manner after injection of the hybrid protein in muscles of living mice. The hybrid protein is then transported retrogradely from the NMJ to target tissues in the central nervous system by crossing synapses to interconnected higher-order neurons (Coen et al., 1997; Miana-Mena et al., 2002). Moreover, transgenic expression of GFP-TTC coexpressed with a lacZ reporter gene confirmed the selectivity of this marker to travel in a retrograde direction (Maskos et al., 2002). Thus, throughout evolution tetanus toxin may have parasitized constitutive retrograde pathways in order to reach deeper layers of the central nervous system. Interestingly, it has been shown that a non-specific receptor that recognizes all neurotrophins and their precursor proteins, p75, and the BDNF-binding receptor TrkB establish interactions with membrane gangliosides required for binding of the toxin to the cell surface (Butowt and Von Bartheld, 2003). In light of these results, it has been suggested that pathogenic proteins may "hijack" existing neurotrophin transport machineries to infiltrate within the cells and to travel long distances towards target tissues (Butowt and Von Bartheld, 2003).

To gain a better understanding of retrograde signaling pathways at the cellular level, the present invention characterizes, in real time, the dynamics of binding and internalization of GFP-TTC within dissociated cortical cells, identifies the native molecules being retrogradely cotransported with GFP-TTC, and elucidates the constitutive pathways that the probe uses to translocate from postsynaptic to presynaptic structures. This invention is useful as a new and sophisticated tool to study the role of retrograde signaling in brain functioning in more complex and physiologically relevant neural networks using optical imaging.

This invention examines the cellular mechanisms whereby the neurotrophic factor BDNF modulates membrane traffic in the central nervous system by using the internalization and retrograde transport properties of the non-toxic fragment of tetanus toxin (TTC) tagged with GFP. A growing body of evidence indicates that the location at which BDNF stimulates a cell is critical for determining the signaling pathways activated and, therefore, the biological response of the cell (Heerssen and Segal, 2002). Furthermore, given the high affinity of BDNF for binding to its specific receptor (i.e. TrkB; (Barbacid, 1994)), it is likely that it can not diffuse far from the site of secretion, thereby acting as an autocrine and/or paracrine factor. These characteristics make BDNF a multifunctional factor capable of playing different roles in membrane turnover depending on the neuronal region in which its effect is localized. Consistent with this, the results presented herein indicate that both presynaptic endocytosis and postsynaptic exocytosis of GFP-TTC are cellular processes dependent on BDNF-induced neuronal activity in dissociated cortical neurons.

Figure 15A:
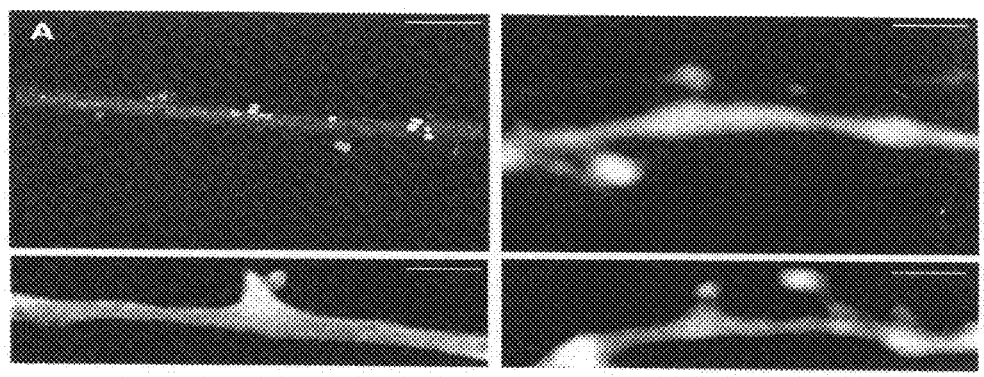

More particularly, this marker, which binds specifically to neurons in the CNS, has been shown to accumulate within postsynaptic specializations in the central synapse (i.e. dendritic spines; see FIG. 15A). In addition, this invention demonstrates that spines accumulating GFP-TTC are associated to active presynaptic endings, inasmuch as they bind rapidly FM1-43 (see FIG. 15C), one of the styryl dyes mentioned above that has been widely used as a presynaptic maker (Betz, 1998). Therefore, this indicates that GFP-TTC can serve as an excellent marker for revealing postsynaptic spines that maintain functional interactions with active presynaptic terminals.

Furthermore, the availability of this probe as reporter plasmid or protein allows researchers to use innovative ways to examine brain function with simple imaging techniques in vitro as well as in transgenic animals, especially non-human transgenic animals. Regarding clinical applications, this probe can be of great interest in early diagnosis of neurodegenerative diseases characterized by a gradual loss of functional synaptic connections in the CNS, such as Alzheimer's and Parkinson's diseases, as well as Epilepsy. Furthermore, GFP-TTC can also be applied for pharmacological screening purposes. Thus, the ability of this probe to be exocytosed from postsynaptic spines (see FIG. 19) by activity-dependent mechanisms can serve as an indicator of the effect of certain drugs on the central synapse.

Tetanus toxin is a potent neurotoxin of 1315 amino acids that is produced by *Clostridium tetani* (1, 2). It prevents the inhibitory neurotransmitter release from spinal cord interneurons by a specific mechanism of cell intoxication (for review see ref 3). This pathological mechanism has been demonstrated to involve retrograde axonal and transynaptic transport of the tetanus toxin. The toxin is taken up by nerve endings at the neuromuscular junction, but does not act at this site; rather, the toxin is transported into a vesicular compartment and travels along motor axons for a considerable distance until it reaches its targets. The transynaptic movement of tetanus toxin was first demonstrated by autoradiographic localization in spinal cord interneurons after injection into a muscle (4). However, previous studies of transynaptic passage of tetanus toxin from motoneurons were limited by the rapid development of clinical tetanus and death of the experimental animal (4, 5, 6).

A fragment of tetanus toxin obtained by protease digestion, the C fragment, has been shown to be transported by neurons in a similar manner to that of the native toxin without causing clinical symptoms (7, 8, 9, 10). A recombinant C fragment was reported to possess the same properties as the fragment obtained by protease digestion (11). The fact that an atoxic fragment of the toxin molecule was able to migrate retrogradely within the axons and to accumulate into the CNS led to speculation that such a fragment could be used as a neurotrophic carrier (12). A C fragment chemically conjugated to various large proteins was taken up by neurons in tissue culture (13) and by motor neurons in animal models (ref. 12, 14, and 15). According to the invention the fragment of tetanus toxin consists of a non-toxic proteolytic fragment of tetanus toxin (TT) comprising a fragment C and a fragment B or a fraction thereof of at least 11 amino acid residues or a non-toxic proteolytic fragment of tetanus toxin (TT) comprising a fragment C and a fragment B or a fraction thereof of at least 11 amino acids residues and a fraction of a fragment A devoid of its toxic activity corresponding to the proteolytic domain having a zinc-binding motif located in the central part of the chain between the amino acids 225 and 245 (cf. Montecucco C. and Schiavo G. Q. Rev. Biophys., (1995), 28:423-472). Thus the fraction of the fragment A comprises, for example, the amino acid sequence 1 to 225 or the amino acid sequence 245 to 457, or the amino acid sequence 1 to 225 associated with amino acid sequence 245 to 457.

The molecule having a biological function is selected from the group consisting of protein of interest, for example, for the compensation or the modulation of the functions under the control of the CNS or the spinal cord or the modulation of the functions in the CNS or the spinal cord, or protein of interest to be delivered by gene therapy expression system to the CNS or the spinal cord. The proteins of interest are, for example, the protein SMN implicated in spinal muscular atrophy (Lefebvre et al., Cell, (1995), 80:155-165 and Roy et al., Cell, (1955), 80:167-178); neurotrophic factors, such as BDNF (Brain-derived neurotrophic factor); NT-3 (Neurotrophin-3); NT-4/5; GDNF (Glial cell-line-derived neurotrophic factor); IGF (Insulin-like growth factor) (Oppenheim, Neuron, (1996), 17:195-197; Thoenen et al., Exp. Neurol., (1933), 124:47-55 and Henderson et al., Adv. Neurol., (1995), 68:235-240); or PNI (protease nexin 1) promoting neurite outgrowth (this factor can be used for the treatment of Alzheimer disease (Houenou et al., PNAS, (1995), 92:895-899)); or SPI3 a serine protease inhibitor protein (Safaei, Dev. Brain Res., (1997), 100: 5-12); or ICE (Interleukin-1β converting Enzyme) a factor implicated in apoptosis, to avoid apoptosis (Nagata, Cell, (1997), 88:355-365); or Bcl-2, a key intracellular regulator of programmed cell death (Jacobson, M. D. (1997), Current Biology, 7:R277-R281); or green fluorescent protein (Lang et al., Neuron, (1997), 18:857-863) as a marker; enzyme (ex: β-Gal); endonuclease like 1-SceI (Choulika A., et al. (1995), Molecular and Cellular biology, 15 (4):1968-

1973 or CRE (Gu H., et al. (1994), Science, 265:103-106); specific antibodies; drugs specifically directed against neurodegenerative diseases such as latero spinal amyotrophy. Several molecules can be associated with a TT fragment.

In association means an association obtained by genetic recombination. This association can be realized upstream as well as downstream to the TT fragment. The preferred mode of realization of the invention is upstream and is described in detail; a downstream realization is also contemplated. (Despite Halpern et al., J. Biol. Chem., (1993), 268(15):11188-11192, who indicated that the carboxyl-terminal amino acids contain the domain required for binding to purified gangliosides and neuronal cells.)

The desired CNS area means, for example, the tongue which is chosen to direct the transport to hypoglossal motoneuron; the arm muscle which is chosen to direct the transport to the spinal cord motoneurons.

For this realization of transplantation of a neuron to the CNS or the spinal cord see Gage, F. H. et al. (1987), Neuroscience, 23:725-807, "Grafting genetically modified cells to the brain: possibilities for the future."

The techniques for introducing the polynucleotides to cells are described in U.S. Pat. Nos. 5,580,859 and 5,589,466, which is relied upon and incorporated by reference herein. For example, the nucleotides may be introduced by transfection in vitro before reimplantation in area of the CNS or the spinal cord.

A chemical linkage is considered for a particular embodiment of the invention and comprises the association between the TT fragment and a polynucleotide encoding the molecule of interest with its regulatory elements, such as promoter and enhancer capable of expressing said polynucleotide. Then the TT fragment allows the retrograde axonal transport and/or the transynaptic transport, and the product of the polynucleotide is expressed directly in the neurons. This chemical linkage can be covalent or not, but preferably covalent performed by thiolation reaction or by any other binding reaction as described in "Bioconjugate Techniques" from Gret T. Hermanson (Academic press, 1996).

The axonal retrograde transport begins at the muscle level, where the composition of interest is taken up at the neuromuscular junction, and migrates to the neuronal body of the motoneurons (which are also called the first order neurons) in the CNS or spinal cord. First order neurons mean neurons that have internalized the composition of interest, and thus in this case, correspond to motoneurons.

The transynaptic retrograde transport corresponds to interneuron communications via the synapses from the motoneurons, and comprises second order neurons and higher order neurons (fourth order corresponding to neurons in the cerebral cortex).

The different stages of the neuronal transport are through the neuromuscular junction, the motoneuron, also called first order neuron, the synapse at any stage between the neurons of different order, neuron of order second to fourth order, which corresponds to the cerebral cortex.

In one embodiment of this invention, it is shown that a β-gal-TTC (TT-fragment C) hybrid protein retains the biological activities of both proteins in vivo. Therefore, the hybrid protein can undergo retrograde and transneuronal transport through a chain of interconnected neurons, as traced by its enzymatic activity. These results are consistent with those of others who used chemically conjugated TTC, or TTC fused to other proteins (12, 13, 14, 15). In these in vitro analyses, the activity of the conjugated or hybrid proteins was likewise retained or only weakly diminished. Depending on the nature of the TTC fusion partner, different types of potential applications can be envisioned. For example, this application can be used to deliver a biologically active protein into the CNS for therapeutic purposes. Such hybrid genes can also be used to analyze and map synaptically connected neurons if reporters, such as lacZ or the green fluorescent protein (GFP; 29) gene, were fused to TTC.

The retrograde transport of the hybrid protein may be demonstrated as follows. When injected into a muscle, β-gal activity rapidly localized to the somata of motoneurons that innervate the muscle. The arborization of the whole nerve, axon, somata and dendrites can easily be visualized. However, in comparison to the neurotropic viruses, the extent of retrograde transneuronal transport of the hybrid protein from the hypoglossal neurons indicates that only a subset of interconnected neurons is detected, although most areas containing second-order interneurons have been identified by the β-gal-TTC marker. Transneuronal uptake is mostly restricted to second order neurons. In such experiments, when a limited amount of a neuronal tracer is injected into a muscle or cell, only a fraction will be transported through a synapse, thereby imposing an experimental constraint on its detection. Presently, the most efficient method, in terms of the extent of transport, relies on neurotropic viruses. Examples include: alpha-herpes viruses, such as herpes simplex type 1 (HSV-1), pseudorabies virus (PrV), and rhabdoviruses (24, 25). Viral methods are very sensitive because each time a virus infects a new cell, it replicates, thereby amplifying the signal and permitting visualization of higher order neurons in a chain. Ultimately, however, one wants to map a neuronal network in an in vivo situation such as a transgenic animal. Here, the disadvantage of viral labeling is its potential toxicity. Most viruses are not innocuous for the neural cell, and their replication induces a cellular response and sometimes cell degeneration (24). Furthermore, depending on experimental conditions, budding of the virus can occur leading to its spread into adjoining cells and tissues.

Differences in mechanisms of transneuronal migration could also account for the restricted number of neurons labeled by β-gal-TTC. Matteoli et al have provided strong evidence that the intact tetanus toxin crosses the synapses by parasitizing the physiological process of synaptic vesicle recycling at the nerve terminal (22). The toxin probably binds to the inner surface of a synaptic vesicle during the time the lumen is exposed to the external medium. Vesicle endocytosis would then presumably provide the mechanism for internalization of the toxin. Because the TTC fragment is known to mimic the migration of the toxin in vivo, it could therefore direct the fusion protein along a similar transynaptic pathway. If this hypothesis is confirmed, it would strongly suggest that synaptic activity is required for the transneuronal transport of β-gal-TTC. Therefore, only active neuronal circuits would be detected by the hybrid protein. The possible dependence of β-gal-TTC on synaptic vesicle exocytosis and endocytosis could be further investigated, since techniques are now available to record synaptic activity in neural networks in vitro (30). In contrast, the transneuronal pathway of neurotropic viruses has not yet been elucidated and could be fundamentally different, involving virus budding in the vicinity of a synapse. Finally, the transneuronal transport of the hybrid protein might depend on a synaptic specificity, although the tetanus toxin is not known to display any (7, 23). It is therefore likely that a virus would cross different or inactive synapses. In summary, the restricted spectrum of interneuronal transport, in addition to its non-toxicity, make the β-gal-TTC hybrid protein a novel and powerful tool for analysis of neural pathways.

One advantage of the fusion gene of the invention for neuronal mapping is that it derives from a single genetic entity that is amenable to genetic manipulation and engineering. Several years ago, a technique based on homologous recombination in embryonic stem cells was developed to specifically replace genes in the mouse (31, 32). This method generates a null mutation in the substituted gene, although in a slightly modified strategy, a dicistronic messenger RNA can also be produced (33, 34). When a reporter gene, such as *E. coli* lacZ, is used as the substituting gene, this technique provides a means of marking the mutated cells so that they can be followed during embryogenesis. Thus, this technique greatly simplifies the analysis of both the heterozygote expression of the targeted gene as well as the phenotype of null (homozygous) mutant animals.

Another advantage of this invention is that the composition comprising the fusion gene may encode an antigen or antigens. Thus, the composition may be used to elicit an immune response in its host and subsequently confer protection of the host against the antigen or antigens expressed. These immunization methods are described in Robinson et al., U.S. Pat. No. 5,43,578, which is herein incorporated by reference. In particular, the method of immunizing a patient or animal host comprises introducing a DNA transcription unit encoding comprising the fusion gene of this invention, which encodes a desired antigen or antigens. The uptake of the DNA transcription unit by the host results in the expression of the desired antigen or antigens and the subsequent elicitation of humoral and/or cell-mediated immune responses.

Neural cells establish specific and complex networks of interconnected cells. If a gene were mutated in a given neural cell, we would expect this mutation to have an impact on the functions of other, interconnected neural cells. With these considerations in mind, a genetic marker that can diffuse through active synapses would be very useful in analyzing the effect of the mutation. In heterozygous mutant animals, the cells in which the targeted gene is normally transcribed could be identified, as could the synaptically connected cells of a neural network. In a homozygous animal, the impact of the mutation on the establishment or activity of the neural network could be determined. The feasibility of such an in vivo approach depends critically on the efficiency of synaptic transfer of the fusion protein, as well as its stability and cellular localization.

Another extension of the invention is to gene therapy applied to the CNS. This invention provides for uptake of a non-toxic, enzyme-vector conjugate by axon terminals and conveyance retrogradely to brainstem motoneurons. A selective retrograde transynaptic mechanism subsequently transports the hybrid protein into second-order connected neurons. Such a pathway, which by-passes the blood-brain barrier, can deliver macromolecules to the CNS. In fact, pathogenic agents, such as tetanus toxin and neurotropic viruses, are similarly taken up by nerve endings, internalized, and retrogradely transported to the nerve cell somata. In such a scenario, the lacZ reporter would be replaced by a gene encoding a protein that provides a necessary or interesting activity and/or function. For example, the human CuZn superoxide dismutase, SOD-1, and the human enzyme, β-N-acetylhexosamimidase A, HexA, have been fused or chemically coupled to the TTC fragment (13, 16), and their uptake by neurons in vitro was considerably increased and their enzymatic functions partially conserved. Combined with the in vivo experiments described here using β-gal-TTC, a gene therapy approach based on TTC hybrid proteins appears to be a feasible method of delivering a biological function to the CNS. However, ways have to be found to target the TTC hybrid proteins, which are likely to be sequestrated into vesicles, to the appropriate subcellular compartment. Such a therapeutic strategy could be particularly useful for treating neurodegenerative and motoneuron diseases, such as amyotrophy lateral sclerosis (ALS, 35), spinal muscular atrophies (SMA, 36, 37), or neurodegenerative lysosomal storage diseases (38, 39). Injection into selected muscles, even in utero, could help to specifically target the appropriate neurons. In addition, such an approach would avoid the secondary and potentially toxic effects associated with the use of defective viruses to deliver a gene (40, 41).

BDNF-Dependent GFP-TTC Endocytosis

In previous studies, it has been demonstrated that tetanus neurotoxin enters through synaptic terminals of hippocampal neurons in vitro by an activity-dependent mechanism (Matteoli et al., 1996). Furthermore, a recent study carried out on mice in vivo has shown that accumulation of the nontoxic fragment of this neurotoxin at the neuromuscular junction is also a process dependent on neuronal activity, inasmuch as axotomy of the sciatic nerve prior to injection of the hybrid protein in the gastrocnemius muscle affected radically TTC distribution (Miana-Mena et al., 2002). However, to date the cellular and molecular mechanisms underlying this neuronal activity remain unknown.

The present invention reports, for the first time, a direct role of BDNF in GFP-TTC internalization by activation of BDNF receptors, which were found often associated to TTC-receptor-enriched membrane microdomains. Consistent with these results, a recent study showed that TTC and the neutrophin receptor p75 (i.e. $p75^{NTR}$) share common endocytic carriers in dissociated rat spinal cord motoneurons, thereby suggesting that entry of the probe may be triggered by activation and internalization of $p75^{NTR}$ (Lalli and Schiavo, 2002). $p75^{NTR}$ is a member of the NGF/TNF receptor superfamily that binds nonselectively all neurotrophins as well as their precursor proteins and that is highly expressed in early stages of CNS development (Chao and Bothwell, 2002). Once development is completed, $p75^{NTR}$ expression is strictly regulated to reach a precise equilibrium with the expression of other neurotrophin receptors (i.e. TrkA, TrkB and TrkC), with which $p75^{NTR}$ establishes interactions in order to strengthen the affinity for their ligands (Chao, 2003). In this scenario, Butowt and colleagues (Butowt and Von Bartheld, 2003) have found that this receptor complex also interacts with a membrane ganglioside required for binding of TTC to the cell membrane (i.e. $G_{T1b}$), although the physiological relevance of this interaction is not clear yet. The formation of this multiprotein complex comprising up to five molecules (i.e. BDNF/TrkB/$p75^{NTR}$/$G_{T1b}$/TTC) may well explain the fact that a tight colocalization between GFP-TTC and BDNF-coated beads was not found at the level of the plasma membrane. Taken together, it is reasonable to propose that activation of TrkB/$p75^{NTR}$ complex by BDNF, which increases the number of docking vesicles at active zones thereby augmenting the exocytic/endocytic turnover (Tyler and Pozzo-Miller, 2001), could enhance binding of TTC to its receptors and induce an elevated endocytic rate in its region of action favoring GFP-TTC uptake.

BDNF- and PSD-Dependent GFP-TTC Intracellular Trafficking

Intracellular traffic of GFP-TTC is a two pronged process: firstly, the probe undergoes a retrograde transport from synaptic terminals to the cell soma. This transport appears to be associated to retrograde pathways used by activated neurotrophin receptors. Thus, in the present invention it was found that GFP-TTC-containing vesicles were in intimate contact with TrkB/BDNF-containing vesicles and that both carriers undergo a similar but independent retrograde transport towards the cell soma. In light of these results, it is hypothesized that TTC would "hijack" the native retrograde motor system used by the activated TrkB receptor (Yano et al., 2001) to reach the neuronal cell body avoiding degradation in the process. Supporting this idea, Lalli and Schiavo reported recently a substantial colocalization between TTC and NGF neurotrophic factor within newborn motoneurons in culture (Lalli and Schiavo, 2002). However, in that work they also observed a morphologically different subpopulation of GFP-TTC-containing vesicles that did not colocalize with NGF, suggesting that these vesicles are transported in a different retrograde pathway. Accordingly, although in different proportions, this invention demonstrates two subpopulations of GFP-TTC retrograde carriers in dissociated cortical neurons: one, representing the 56% of the overall GFP-TTC-containing vesicle population, localized in close proximity to BDNF-containing vesicles and a second, representing the remaining 44%, displaying no interactions with BDNF carriers. Interestingly, it has been found recently that TTC activates intracellular signaling pathways common to Trk receptor phosphorylation, this effect being dependent on the interaction of the protein with the cell membrane inasmuch as TTC triggers activation of the same signals as tetanus toxin (Gil et al., 2003). Thus, the population of GFP-TTC-containing vesicles displaying no interactions with BDNF-containing vesicles may correspond to the fraction of Trk receptors directly activated by TTC independently from BDNF.

Secondly, GFP-TTC is transported from the neuronal cell soma to postsynaptic structures, such as dendritic spines, where it accumulates. These structures are spherical protrusions distributed all along the neuronal dendritic arbors, where intracellular cascades of anterograde and retrograde signaling processes begin (Hering and Sheng, 2001). Spines could then act as structures for transynaptic passage of the GFP-TTC to presynaptic cells. During this trafficking stage, GFP-TTC could make use of another intracellular transport pathway to be specifically addressed towards these postsynaptic structures, the PSD protein localization. In fact, in this invention it has been observed that intracellular GFP-TTC clusters colocalize with PSD-Zip45, one of the numerous components of the PSD (Kato et al., 1998; Xiao et al., 1998). PSD-Zip45 has been shown to display a rapid redistribution in the PSD depending on neuronal activity (Okabe et al., 2001). Thus, during cell depolarization PSD-Zip45 would be addressed to dendritic spines in a fast and precise manner and GFP-TTC could capitalize upon this transportation to reach postsynaptic zones. Nevertheless, further studies will be required to elucidate the molecular mechanisms whereby GFP-TTC recognizes this intracellular pathway, as well as the possible interactions that the hybrid protein and PSD proteins could display.

BDNF-Dependent GFP-TTC Exocytosis

Recent studies have demonstrated that intramuscular injections of the TTC fused to a marker protein (i.e. β-Gal) into the tongue of mice undergoes a retrograde transport towards the central nervous system (Miana-Mena et al., 2002). However, to date little information is available on how TTC can travel retrogradely throughout different neuronal layers. In light of the results presented in this work, the inventors hypothesized that, once GFP-TTC has reached postsynaptic specializations, it can be released into the synaptic cleft and taken up by the presynaptic neuron in a BDNF-induced neuronal activity-dependent process. This process may occur as illustrated in FIG. 18. Depolarization of the presynaptic cell would trigger neurotransmitter release, thereby propagating the signal to the postsynaptic neuron. Thus, stimulation of postsynaptic specializations would induce secretion of BDNF into the synaptic cleft, which would bind to its receptors in the presynaptic as well as in the postsynaptic neuron. BDNF bound to presynaptic TrkB receptor complex would trigger a massive neurotransmitter release that would reinforce the presynaptic signal propagation. On the other hand, BDNF bound to postsynaptic receptors would trigger release of GFP-TTC, which would bind to the membrane gangliosides associated to TrkB receptor complex in both presynaptic and postsynaptic cells. After massive exocytosis in the presynaptic terminal, endocytosis follows, and recycling of presynaptic membrane could bring GFP-TTC/receptor complex within the presynaptic cell. The participation of BDNF in GFP-TTC uptake is not surprising when taking into account the fact that snake venoms contain high levels of NGF, which has been proposed to facilitate the access of toxins to their target tissues (Kostiza and Meier, 1996). However, the fraction of GFP-TTC-containing vesicles not associated to BDNF/receptor complex found in this study could be the result of GFP-TTC endocytosis by a caveolae-like membrane recycling pathway (i.e. potocytosis). This mechanism, independent of the clathrin-coated pit endocytic pathway, has been considered responsible of internalizing some molecules within cells, including pathogens and pathogen-derived molecules, and delivering them to the ER (Anderson, 1998). Another possibility could be that GFP-TTC activates directly Trk receptors, as it has been recently suggested, inasmuch as TTC stimulates common intracellular signaling cascades as those activated after Trk-receptor phosphorylation (Gil et al., 2003). Thus, this mechanism would represent an alternative pathway whereby GFP-TTC would invade presynaptic cells even in the absence of neurotrophin-induced neuronal activity. This could represent a generalized mechanism for neuronal invasion by neurotoxins and neurodegenerative viruses.

In conclusion, the present invention provides new information on the membrane traffic taking place at the central synapse and the role that neurotrophin-induced synaptic activity plays in this process. Taken together, these results show that the membrane trafficking pathways described above would participate in bringing in and out of the active synapse (at the presynaptic as well as the postsynaptic side) necessary components for modulating synapse activity.

EXAMPLE 1

Figure 2:
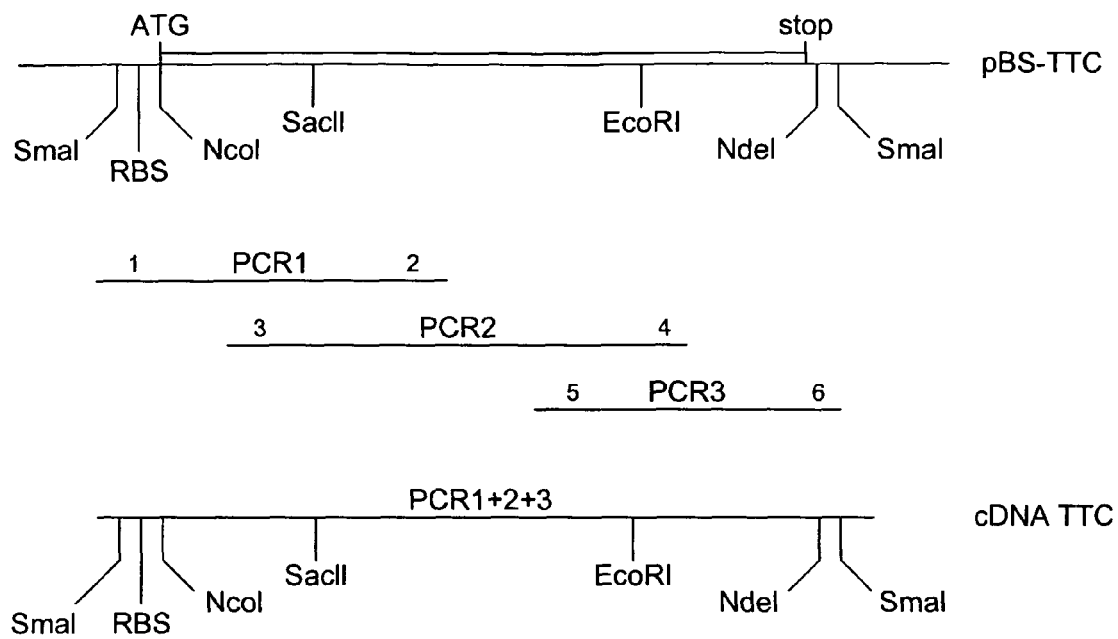
FIG. 2 shows the details of construct pBS:TTC. TTC cDNA isolation: The TTC cDNA was isolated from a *Clostridium Tetani* strain using Polymerase Chain Reaction. We used a three time PCR to generate three overlapping fragments respectively of 465 bp (PCR1; primer 1:5'-CCC CCC GGG CCA CCA TGG TTT TTT CAA CAC CAA TTC CAT TTT CTT ATT C-3' (SEQ ID NO:4) & primer 2: 5'-CTA MAA CAG TAA TTT CTG 3' (SEQ ID NO:5) of 648 bp (PCR2; primer 3: 5'-AAT TAT GGA CTT TAA AAG ATT CCG C-3' (SEQ ID NO:6) & primer 4: 5'-GGC ATT ATA ACC TAC TCT TAG AAT-3 (SEQ ID NO:7) and of 338 bp (PCR3; primer 5: 5'-MT GCC TTT AAT AAT CTT GAT AGA AAT-3' (SEQ ID NO:8) & primer 6: 5-CCC CCC GGG CAT ATG TCA TGA ACA TAT CAA TCT GTT TAA TC-3' (SEQ ID NO:9), and each fragment was sequentially cloned into pBluescript KS+ to produce plasmid pBS-TTC. The upstream primer contained the Ribosome Binding Site (RBS) and translation initiation signals.

Plasmid Constructions (A) TTC Cloning:

Full length TTC DNA was generated from the genomic DNA from the *Clostridium Tetani* strain (a gift from Dr. M. Popoff, Institut Pasteur) using PCR. Three overlapping fragments were synthesized: PCR1 of 465 by (primer 1: 5'-CCC CCC GGG CCA CCA TGG TTT TTT CAA CAC CAA TTC CAT TTT CTT ATT C-3' (SEQ ID NO: 4) and primer 2: 5'-CTA AAC CAG TAA TTT CTG-3') (SEQ ID NO: 5), PCR2 of 648 by (primer 3: 5'-AAT TAT GGA CTT TAA AAG ATT CCG C-3' (SEQ ID NO: 6) and primer 4: 5'-GGC ATT ATA ACC TAC TCT TAG AAT-3' (SEQ ID NO: 7)), and PCR3 of 338 by (primer 5: 5'-AAT GCC TTT AAT AAT CTT GAT AGA AAT-3' (SEQ ID NO: 8) and primer 6: 5'-CCC CCC GGG CAT ATG TCA TGA ACA TAT CAA TCT GTT TAA TC-3' (SEQ ID NO: 9)). The three fragments were sequentially introduced into pBluescript KS+ (Stratagene) to give pBS:TTC plasmid. The upstream primer 1 also contains an optimized eukaryotic Ribosome Binding Site (RBS) and translational initiation signals. The TTC fragment (462 amino acids) represents the amino acids 854-1315 of tetanus holotoxin, i.e. the carboxy-terminal 451 amino acids of the heavy chain, which constitute the fragment C plus 11 amino acids of the heavy chain that immediately precede the amino terminus of the fragment C. The DNA sequence and amino acid sequence of the TTC fragment cloned in pBS:TTC is shown in FIG. 1. The construct pBS:TTC is shown in FIG. 2.

Figure 3:
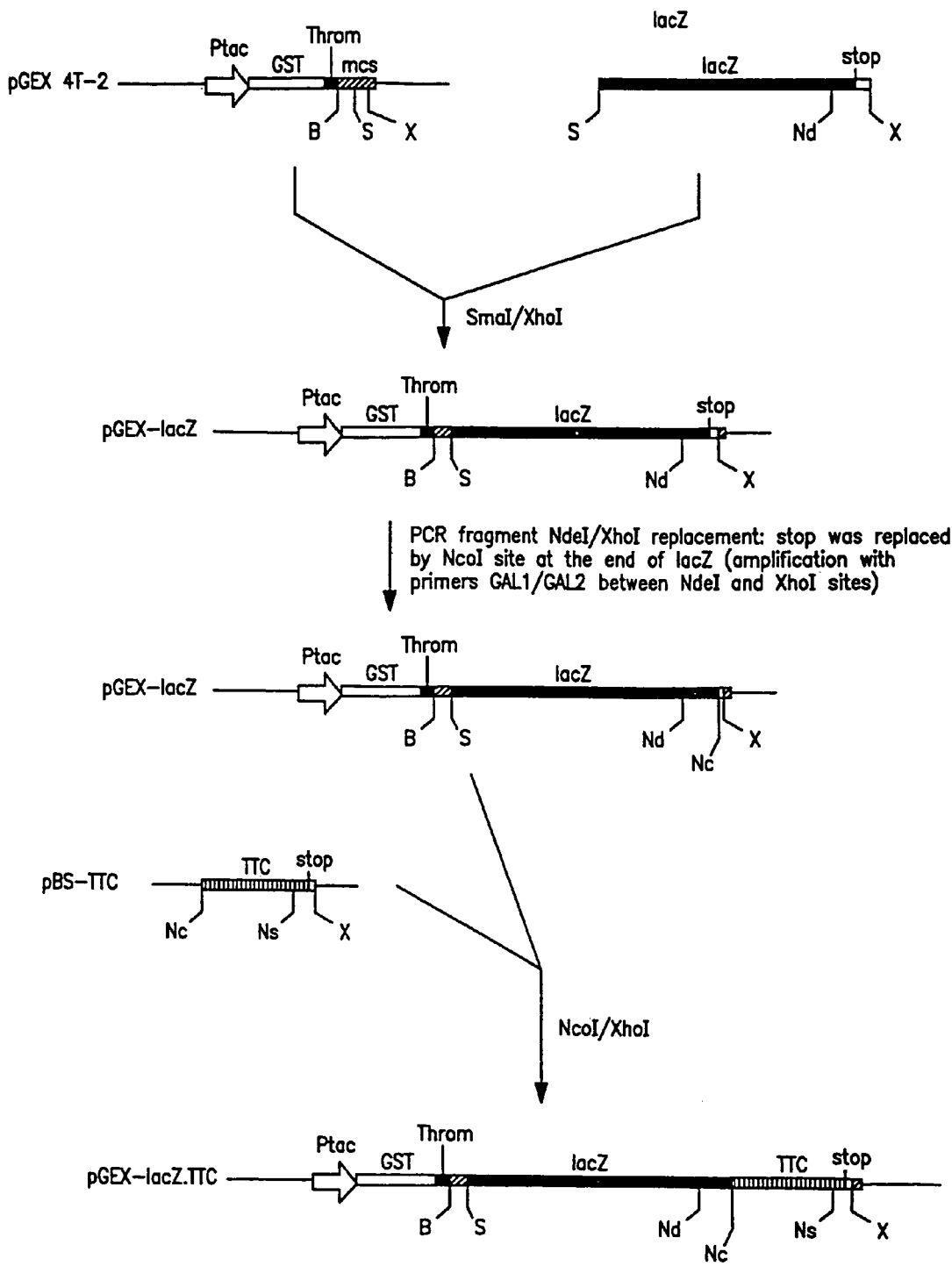
FIG. 3 depicts pGEX:lacZ-TTC construct.

(B) pGEX:lacZ-TTC:

pGEX:IacZ was obtained by cloning a SmaI/XhoI lacZ fragment from the pGNA vector (a gift from Dr. H. Le Mouellic) into pGEX 4T-2 (Pharmacia). PCR was used to convert the IacZ stop codon into an NcoI restriction site. Two primers (upstream: 5'-CTG AAT ATC GAC GGT TTC CAT ATG-3' (SEQ ID NO: 10) and downstream: 5'-GGC AGT CTC GAG TCT AGA CCA TGG CTT TTT GAC ACC AGA C-3' (SEQ ID NO: 11)) were used to amplify the sequence between NdeI and XhoI, generating pGEX:lacZ(NcoI) from pGEX:IacZ. pGEX:IacZ-TTC was obtained by insertion of the TTC NcoI/XhoI fragment into pGEX:lacZ(NcoI), fusing TTC immediately downstream of the lacZ coding region and in the same reading frame. FIG. 3 shows the details of the pGEX:IacZ-TTC construct.

Figure 4:
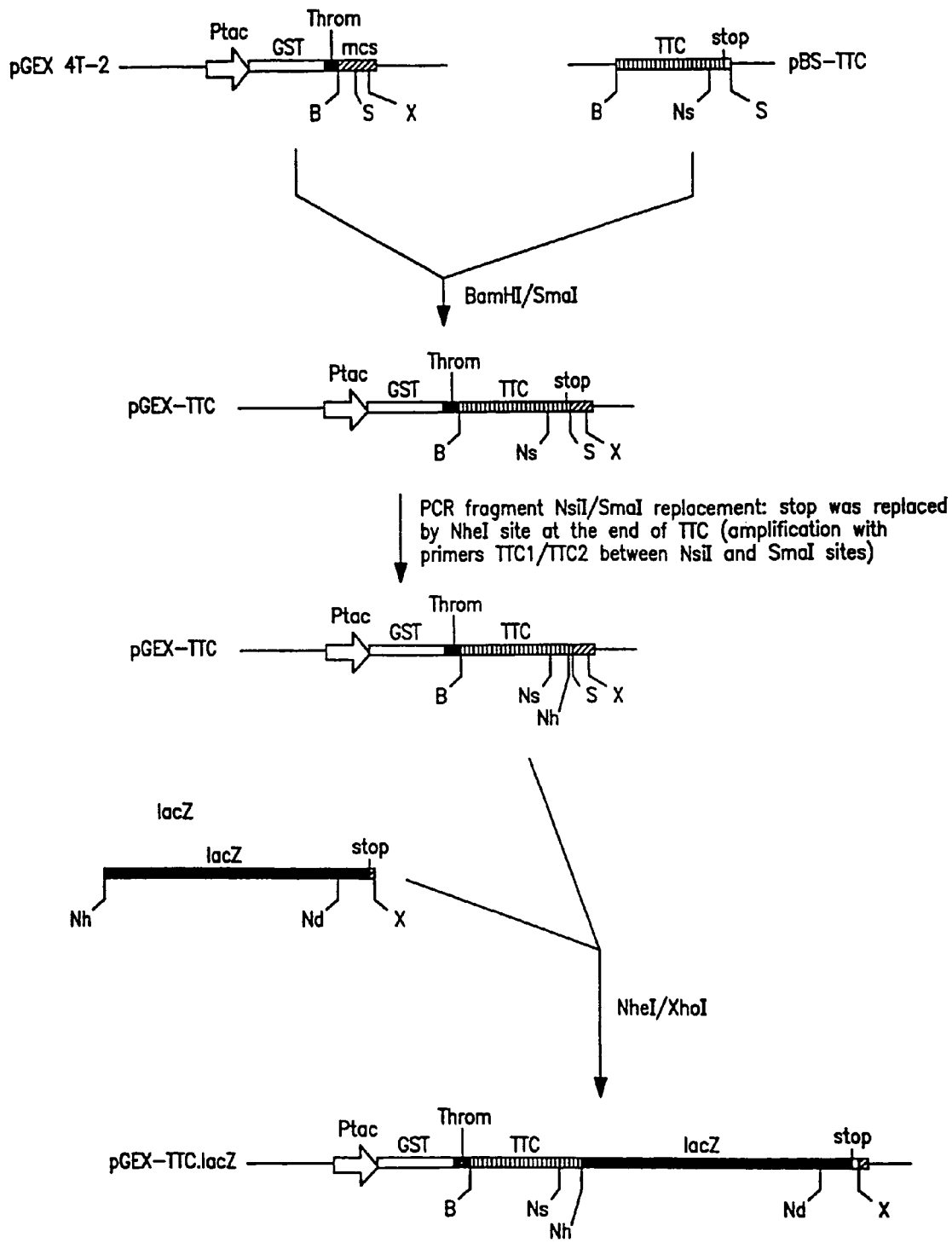
FIG. 4 shows construct pGEX:TTC-lacZ.
Figure 5:
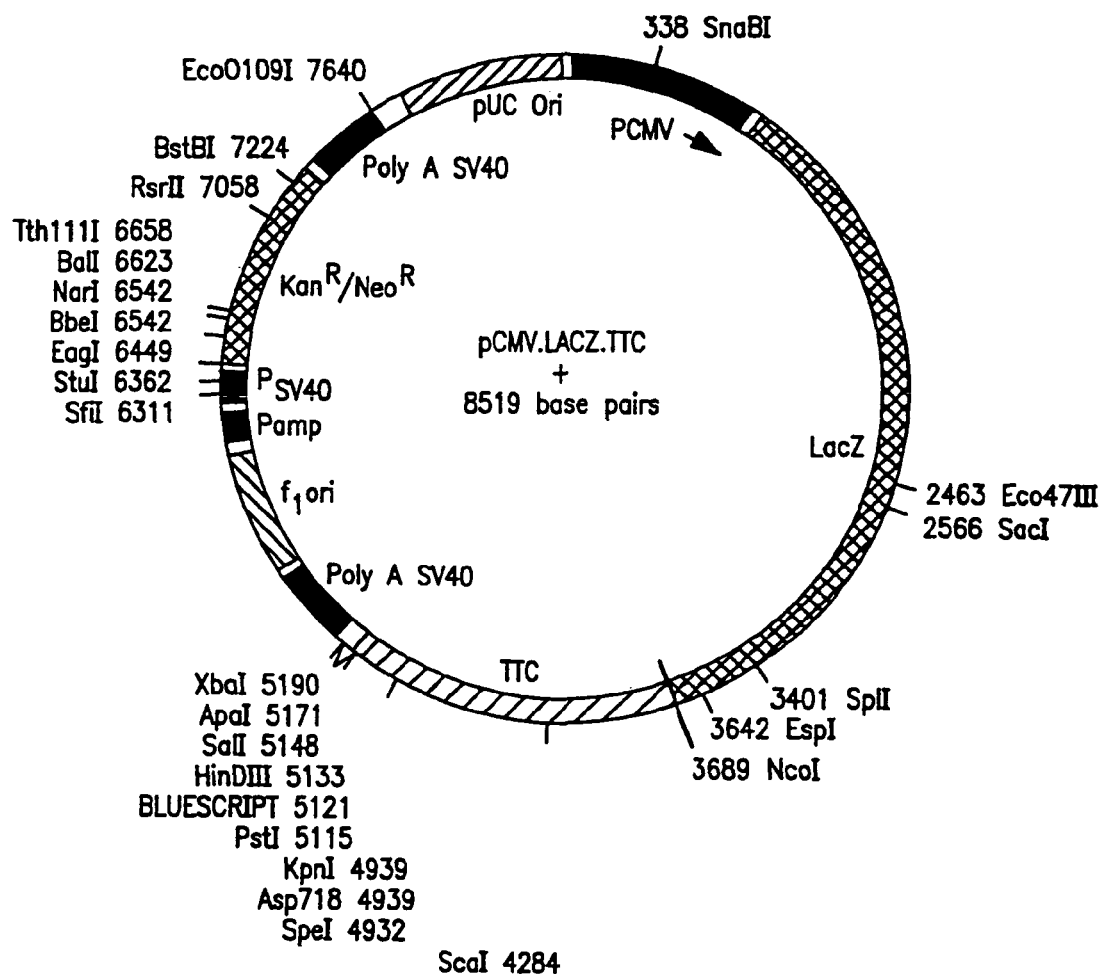
FIG. 5 depicts the details of the construct pCMV:lacZ-TTC.

(C) pGEX:TTC-lacZ:

pBS:TTC was modified to change NcoI into a BamHI restriction site (linker 5'-CAT GAC TGG GGA TCC CCA GT-3' (SEQ ID NO: 12)) at the start of the TTC DNA, to give pBS:TTC(BamHI) plasmid. pGEX:TTC was obtained by cloning. The TTC BamHI/SmaI fragment from pBS:TTC (BamHI) into pGEX 4T-2 (Pharmacia). PCR was used to convert the TTC stop codon into an NheI restriction site. Two primers (upstream: 5'-TAT GAT MA MT GCA TCT TTA GGA-3' (SEQ ID NO: 13) and downstream: 5'-TGG AGT CGA CGC TAG CAG GAT CAT TTG TCC ATC CTT C-3' (SEQ ID NO: 14)) were used to amplify the sequence between NsiI and SmaI, generating pGEX:TTC(NheI) from pGEX:TTC. The lacZ cDNA from plasmid pGNA was modified in its 5' extremity to change SacII into an NheI restriction site (linker 5'-GCT AGC GC-3' (SEQ ID NO: 15)). pGEX: TTC-lacZ was obtained by insertion of the IacZ NheI/XhoI fragment into pGEX:TTC(NheI), fusing IacZ immediately downstream of the TTC coding region and in the same reading frame. The details of the construct of pGEX:TTC-IacZ are shown in FIG. 4.

(D) pCMV:lacZ-TTC:

pCMV vector was obtained from pGFP-C1 (Clontech laboratories) after some modifications: GFP sequence was deleted by a BglII/NheI digestion and religated, and SacII in the polylinker was converted into an AscI restriction site (linkers 5'-GAT ATC GGC GCG CCA GC-3' (SEQ ID NO: 16) and 5'-TGG CGC GCC GAT ATC GC-3' (SEQ ID NO: 17)).

pBluescript KS+ (Stratagene) was modified to change XhoI into an AscI restriction site (linker 5'-TCG ATG GCG CGC CA-3' (SEQ ID NO: 18)), giving pBS(AscI) plasmid. pBS:lacZ-TTC was obtained by cloning a XmaI lacZ-TTC fragment from pGEX:IacZ-TTC into pBS(AscI). pCMV: lacZ-TTC was obtained by insertion of the lacZ-TTC XmnI/AscI fragment into pCMV vector at the XhoI and AscI sites (XhoI and XmnI was eliminated with the clonage), putting the fusion downstream of the CMV promotor. FIG. 8 shows the details of the construct pCMV:lacZ-TTC. Plasmid pCMV:lacZ-TTC was deposited on Aug. 12, 1997, at the Collection Nationale de Cultures de Microorganisms (CNCM), Institut Pasteur, 25, Rue de Docteur Roux, F-75724, Paris Cedex 15, France, under Accession No. 1-1912.

EXAMPLE 2

Purification of the Hybrid Protein

The *E. coli* strain SR3315 (a gift from Dr. A. Pugsley, Institut Pasteur) transfected with pGEX:lacz-TTC was used for protein production. An overnight bacterial culture was diluted 1:100 in LB medium containing 100 µg/ml ampicillin, and grown for several hours at 32° C. until an OD of 0.5 was reached. Induction from the Ptac promoter was achieved by the addition of 1 mM IPTG and 1 mM $MgCl_2$ and a further 2 hrs incubation. The induced bacteria were pelleted by centrifugation for 20 min at 3000 rpm, washed with PBS and resuspended in lysis buffer containing 0.1 M Tris pH 7.8, 0.1 M NaCl, 20% glycerol, 10 mM EDTA, 0.1% Triton-X100, 4 mM DTT, 1 mg/ml lysozyme, and a mixture of anti-proteases (100 µg/ml Pefablok, 1 µg/ml leupeptin, 1 µg/ml pepstatin, 1 mM benzamidine). After cell disruption in a French Press, total bacterial lysate was centrifuged for 10 min at 30000 rpm. The resulting supernatant was incubated overnight at 4° C. with the affinity matrix Glutathione Sepharose 4B (Stratagene) with slow agitation. After centrifugation for 5 min at 3000 rpm, the matrix was washed three times with the same lysis buffer but without lysozyme and glycerol, and then three times with PBS. The resin was incubated overnight at 4° C. with Thrombin (10 U/ml; Sigma) in PBS in order to cleave the β-gal-TTC fusion protein from the Glutatione-S-transferase (GST) sequence and thereby elute it from the affinity column. Concentration of the eluted fusion protein was achieved by centrifugation in centricon X-100 tubes (Amicon; 100,000 MW cutoff membrane).

Purified hybrid protein was analyzed by Western blotting after electrophoretic separation in 8% acrylamide SDS/PAGE under reducing conditions followed by electrophoretic transfer onto nitrocellulose membranes (0.2 mm porosity, Bio-Rad). Immunodetection of blotted proteins was performed with a Vectastaln ABC-alkaline phosphatase kit (Vector Laboratories) and DAB color development. Antibodies were used as follows: rabbit anti-β-gal antisera (Capel), dilution 1:1000; rabbit anti-TTC antisera (Calbiochem), dilution 1:20000. A major band with a relative molecular mass of 180 kDa corresponding to the β-Gal-TTC hybrid protein was detected with both anti-β-Gal anti-TTC antibodies.

EXAMPLE 3

Binding and Internalization of Recombinant Protein in Differentiated 1009 Cells

The 1009 cell line was derived from a spontaneous testicular teratocarcinoma arising in a recombinant inbred mouse strain (129×B6) (17). The 1009 cells were grown in Dulbecco's modified Eagle's medium (DMEM) containing 10% fetal calf serum and passaged at subconfluence. In vitro differentiation with retinoic acid and cAMP was performed as described (18). Eight days after retinoic acid treatment, cells were used for the internalization experiments with either the hybrid protein or β-gal.

Binding and internalization of the β-Gal-TTC fusion were assessed using a modified protocol (16). Differentiated 1009 cells were incubated for 2 hrs at 37° C. with 5 µg/ml of δ-Gal-TTC or β-Gal protein diluted in binding buffer (0.25% sucrose, 20 mM Tris acetate 1 mM CaCl2, 1 mM $MgCl_2$, 0.25% bovine serum albumin, in PBS). The cells were then incubated with 1 µg/ml Pronase E (Sigma) in PBS for 10 min at 37° C., followed by washing with proteases inhibitors diluted in PBS (100 µg/ml Pefablok, 1 mM benzamidine).

The cells were fixed with 4% formalin in PBS for 10 min at room temperature (RT) and then washed extensively with PBS. β-gal activity was detected on fixed cells by an overnight staining at 37° C. in X-Gal solution (0.8 mg/ml X-Gal, 4 mM potassium ferricyanide, 4 mM potassium ferrocyanide, 4 mM $MgCl_2$ in PBS). For electron microscopy, the cells were further fixed in 2.5% glutaraldehyde for 18 hrs, and then processed as described (19).

For immunohistochemical labeling, cells were fixed with 4% paraformaldehyde in PBS for 10 min at RT then washed extensively with PBS, followed by a 1 hr incubation at RT with 2% BSA/0.02% Triton X-100 in PBS. Cells were co-incubated in primary antibodies diluted in 2% BSA/0.02% Triton X-100 in PBS for 2 hrs at RT. Antibodies used were a mouse anti-neurofilament antibody (NF 200 Kd, dilution 1:50; Sigma) or the rabbit anti-TTC antibody (dilution 1:1000). The labeling was visualized using fluorescent secondary antibodies: Cy3, goat anti-rabbit IgG (dilution 1:500; Amersham) or anti-mouse IgG with extravidin-FITC (dilution 1:200; Sigma). Cells were mounted in moviol and visualized with epifluorescence.

EXAMPLE 4

In Vivo Recombinant Protein Injection 14-week old B6D2F1 mice were obtained from IFFA-CREDO. The animal's tongue muscle was injected using an Hamilton syringe (20 µl per animal) while under general anesthesia with 3% Avertin (15 µl/g of animal). The protein concentration was 0.5 to 5 µg/µl in PBS; therefore, mice received approximately 10 to 100 µg per injection. Animals were kept alive for 12 hrs to 48 hrs post-injection to permit migration of the injected protein, and in no case were any tetanus symptoms detected. The mice were sacrificed by intracardiac perfusion with 4% paraformaldehyde in PBS while under deep anesthesia. Brains were harvested, rinsed in PBS and incubated in 15% sucrose overnight at 4° C., then mounted in tissue-tek before sectioning, 15 µm thick slices using a cryostat.

EXAMPLE 5

Histology, Immunohistology, and X-Gal Staining

For in toto X-Gal staining of the dissected brain and tongue, mice (10 animals) were sacrificed and fixed as described above. The brain was further cut with a scalpel along a median plane and directly incubated for 12 hrs in X-Gal solution.

For immunohistology, sections were incubated In a 1:5000 dilution of anti-TTC antibody in 2% BSA/0.02% Triton X-100 in PBS overnight at 4° C. after nonspecific antibody binding sites were blocked by a 1 hr incubation in the same buffer. Antibody detection was carried out using the Vectastain ABC-alkaline phosphatase kit with DAB color development. For X-Gal staining, sections were incubated in X-Gal solution and counterstained for 30 sec with hematoxylin 115 (v/v) in PBS. Histology on adjacent sections was done after X-Gal staining, using a 30 sec incubation in hematoxylin/thionin solution. All sections were mounted in moviol before eight microscopy analysis.

EXAMPLE 6A

Internalization of the β-gal-TTC Fusion Protein by Neurons In Vitro

Differentiation of 1009 cells with retinoic acid and cAMP in vitro yields neuronal and glial cells (18, 20). X-Gal staining or immunolabeling were performed after incubation with the β-gal-TTC fusion protein or with either the β-gal or TTC proteins alone. Only when the hybrid protein was incubated with differentiated 1009 cells was a strong X-Gal staining detected in cells having a neuronal phenotype. No signal was detected when β-gal alone was incubated under the same conditions. A similar X-Gal staining pattern was obtained after pronase treatment of the cells to remove surface bound proteins, indicating that the hybrid protein had been internalized. The intracellular localization of the hybrid protein was further confirmed by electron microscopic analysis of X-Gal-stained cells. Furthermore, the enzymatic activity observed in axons seemed to be localized in vesicles associated with filaments, which is in agreement with previous work on TTC fragment or native tetanus toxin (14, 21, 22). Co-labeling with anti-TTC and anti-neurofilament antibodies revealed that β-gal activity co-localized with TTC fragment in neuronal cells. No glial cells were labeled with either antibody.

EXAMPLE 6B

Internalization of the TTC-β-gal Fusion Protein by Neurons In Vitro

The method used for the internalization was identical to that described in Example 6 above. The results show efficiently internalization of the hybrid as in Example 6 above.

EXAMPLE 7

Retrograde Transport of the Hybrid Protein In Vivo

To study the behavior of the β-gal-TTC protein in vivo, the hybrid protein was tested in a well characterized neuronal network, the hypoglossal system. After intramuscular injection of β-gal-TTC protein into the mouse tongue, the distribution of the hybrid protein in the CNS was analyzed by X-Gal staining. Various dilutions of the protein were injected and sequential time points were analyzed to permit protein transport into hypoglossal motoneurons (XII), and its further transneuronal migration into connected second order neurons.

A well-defined profile of large, apparently retrogradely labeled neurons was clearly evident in the hypoglossal structure, analyzed in toto at 12 hrs post-injection. A strong labeling was also apparent in the hypoglossal nerve (XIIn) of the tongue of the injected mice. At the level of muscle fibers, button structures were observed that might reflect labeling of neuromuscular junctions where the hybrid protein was internalized into nerve axons. These data demonstrate that the β-gal-TTC hybrid protein can migrate rapidly by retrograde axonal transport as far as motoneuron cell bodies, after prior uptake by nerve terminals in the tongue. This specific uptake and the intraaxonal transport are similar to the properties that have been described for the native toxin (6, 21, 23).

Transport of the hybrid protein was examined in greater detail by analyzing X-Gal-stained brain sections. Motoneurons of the hypoglossal nucleus became labeled rapidly, with 12 hrs being the earliest time point examined. Most of the label was confined to neuronal somata, the cell nuclei being unlabeled. The intensity of the labeling depends upon the concentration of the β-gal-TTC protein injected: when 10 µg of protein was injected, only the hypoglossal somata were detected, whereas with 25 to 50 µg a fuzzy network of dendrites was visualized; transynaptic transfer was detected with 100 µg of hybrid protein. An identical distribution of label was observed then brain sections were immunostained with an anti-TTC antibody, demonstrating that β-gal and TTC fragment co-localize within cells. Finally, injection of β-gal alone did not result in labeling of the hypoglossal nuclei and therefore confirms that transport of the hybrid protein is TTC-dependent. Labeling with an anti-TTC antibody was less informative than detection of β-gal activity; for instance, the nerve pathway to the brain could not be visualized by anti-TTC immunostaining. At 18 hrs post-injection, labeling was observed in the hypoglossal nuclei: all motoneuron cell bodies and the most proximal part of their dendrites were very densely stained. In contrast, no labeling was ever detected in glial cells adjoining XII motoneurons or their axons. Our results are in accordance with others who reported an identical pattern of immunolabeling after injection of the TTC fragment alone (9). Transneuronal transfer is detectable after 24 hrs. An additional 24 hrs and beyond did not yield a different staining.

EXAMPLE 8

Transneuronal Transport of the Hybrid Protein

Second order interneurons, as well as higher order neurons that synapse with the hypoglossal motoneurons, have been extensively analyzed using conventional markers, such as the wheat germ agglutinin-horseradish peroxidase complex (WGA-HRP) or neurotropic viruses such as alpha-herpes (24) and rhabdoviruses (25). An exhaustive compilation of regions in the brain that synaptically connect to the hypoglossal nucleus has also been described recently (25). In this invention, the distribution of the β-gal-TTC fusion depended on the initial concentration of protein injected into the muscle and the time allowed for transport after injection. Up to 24 hrs post-injection, labeling was restricted to the hypoglossal nuclei. After 24 hrs, the distribution of second order transneuronally labeled cells in various regions of the brain was consistent and reproducible. Even at longer time points (e.g. 48 hrs), labeling of the hypoglossal nucleus remained constant. At higher magnification, a discrete and localized staining of second-order neurons was observed, suggesting that the hybrid protein had been targeted to vesicles within cell somata, synapses and axons. A similar patchy distribution was previously described for tetanus toxin and TTC fragment alone (14, 21, 22).

Intense transneuronal labeling was detected in the lateral reticular formation (LRF), where medullary reticular neurons have been reported to form numerous projections onto the hypoglossal nucleus (26, 27). β-gal activity was detected bilaterally in these sections. Label led LRF projections formed a continuous column along the rostrocaudal axis, beginning lateral to the hypoglossal nucleus, with a few neurons being preferentially stained in the medullary reticular dorsal (MdD) and the medullary reticular ventral (MdV) nuclei. This column extends rostrally through the medulla, with neurons more intensely labeled in the parvicellular reticular nucleus (PCRt, caudal and rostral). After 48 hrs, cells in MdD and PCRt were more intensely stained. A second bilateral distribution of medullary neurons projecting to the hypoglossal nucleus was detected in the solitary nucleus (Sol) but the labeling was less intense than in the reticular formation, presumably because relatively few cells of the solitary nucleus project onto the hypoglossal nucleus (26). However, no labeling was found in the spinal trigeminal nucleus (Sp5), which has also been shown to project onto the hypoglossal nucleus (26). Transynaptic transport of the β-gal-TTC protein was also detected in the pontine reticular nucleus caudal (PnC), the locus coeruleus (LC), the medial vestibular nucleus (MVe) and in a few cells of the inferior vestibular nucleus (IV). These cell groups are known to project onto the hypoglossal nucleus (25), but their labeling was weak, probably because of the greater length of their axons. A few labeled cells were observed in the dorsal paragigantocellular nucleus (DPGi), the magnocellular nucleus caudal (RMc), and the caudal raphe nucleus (R); their connections to the hypoglossal nucleus have also been reported (25). Finally, labeled neurons were detected bilaterally in midbrain projections, such as those of the mesencephalic trigeminal nucleus (Me5), and a few neurons were stained in the mesencephalic central gray region (CG). These latter nuclei have been typed as putative third order cell groups related to the hypoglossal nucleus (25).

Neurons in the motor trigeminal nucleus (Mo5) and the accessory trigeminal tract (Acs5) were also labeled, along with a population of neurons in the facial nucleus (N7). However, interpretation of this labeling is more ambiguous, since it is known that motoneurons in these nuclei also innervate other parts of the muscular tissue, and diffusion of the hybrid protein might have occurred at the point of injection. Conversely, these nuclei may have also projected to the tongue musculature via nerve XII, since neurons in N7 have been reported to receive direct hypoglossal nerve input (28). This latter explanation is consistent with the fact that labeling in these nuclei was detected only after 24 hrs; however, this point was not further investigated.

Together, the data summarized in Table 1 clearly establish transneuronal transport of the β-gal-TTC fusion protein from the hypoglossal neurons into several connected regions of the brainstem.

TABLE 1

Transneuronal transport of the lacZ-TTC fusion from the XII nerve: labeling of different cells types in the central nervous system.

| Cell groups | 12-18 hrs | 24-48 hrs |
|---|---|---|
| First order neurons | | |
| First category: | | |
| XII, hypoglossal motoneurons | ++ | +++ |
| Second category: | | |
| N7, facial nu | – | ++ |
| Mo5, motor trigeminal nu | – | ++ |
| Acs5, accessory trigeminal nu | – | + |
| Second order cell groups | | |
| MdD, medullary reticular nu, dorsal | – | ++ |
| MdV, medullary reticular nu, ventral | – | +/– |
| PCRt, parvicellular reticular nu, caudal | – | ++ |
| PCRt, parvicellular reticular nu, rostral | – | ++ |
| Sol, solitary tract nu | – | + |
| DPGi, dorsal paragigantocellular nu | – | +/– |
| PnC, pontine reticular nu, caudal | – | + |
| RMc, magnocellular reticular nu | – | +/– |
| R, caudal raphe nu | – | +/– |
| MVe, medial vestibular nu | – | + |
| IV, inferior vestibular nu | – | +/– |
| LC, locus coeruleus | – | + |
| Me5, mesencephalic trigeminal nu (*) | – | + |
| CG, mesenphalic central gray (*) | – | +/– |

(*) Represents second order cell groups that also contain putative third order neurons (see text).
–, no labeling;
+ to +++, increased density of label;
+/– weak labeling.
16 animals were analysed for the 12-18 hrs p.i. data;
6 animals were analysed for the 24-48 hrs p.i. data.

In another embodiment of the invention, we have constructed a fusion protein (GFP-TTC) comprising the C-terminal fragment of tetanus toxin and the GFP reporter gene, and have demonstrated its effectiveness to map a simple neural network retrogradely and transsynaptically in transgenic mice. (Maskos et al., 2002). The GFP-TTC fusion protein permits the visualization of membrane traffic at the presynaptic level of the neuromuscular junction and can be detected opticaly without immunological or enzymatic reactions. The GFP-TTC fusion protein, therefore, permits observation of active neurons with minimal disturbance of their physiological activities.

We have also previously shown that, without neural activity, localization of a TTC fusion protein at the NMJ is impaired (Miana-Mena et al., 2002). In this aspect of the invention, therefore, we investigated in vivo, the influence of neurotrophic factors on neuronal localization and internalization of GFP-TTC and the mechanisms by which certain neurotrophic factors influence neuronal trafficking in vivo. We found that localization of GFP-TTC at the NMJ is rapidly induced by neurotrophic factors such as Brain Derived Neurotrophic Factor (BDNF), Neurotrophin 4 (NT-4), and Glial-Derived Neurotrophic Factor (GDNF) but not by Nerve Growth Factor (NGF), Neurotrophin 3 (NT-3), and Ciliary Neurotrophic Factor (CNTF).

Co-injection of various amounts of BDNF with the GFP-TTC probe induces an increase of the fluorescence measured at the neuromuscular junction (NMJ). This effect, which is detectable as early as 5 min after injection and reaches a maximum level at about 30 min after injection, indicates that BDNF treatment enhances neuronal endocytosis. Among other functions, BDNF stimulates the secretion of neurotransmitter from *Xenopus* nerve muscle co-cultures and from hippocampal neurons (Lohof et al., 1993; Tyler and Pozzo-Miller, 2001). Since tetanus toxin is known to enter neurons by means of synaptic vesicle endocytosis (Matteoli et al., 1996), BDNF might increase GFP-TTC internalization through enhancement of synaptic vesicle turnover. In our study, BDNF effects persisted after BoTx/A treatment, which blocks exocytosis and endocytosis of synaptic vesicles, showing that BDNF increases the kinetics and localization of a TTC-containing fusion protein at the NMJ through another endocytic pathway. Therefore, intramuscular injection of GFP-TTC and visualization of transport mechanisms revealed at least two different endocytic pathways: a clathrin-dependent and a clathrin-independant pathways. We found that after intramuscular injection of GFP-TTC, it displayed characteristics consistent with localization in lipid rafts, including biochemical colocalization with caveolin 3 and colocalization with GM1, a raft marker identified by CT-b binding (Orlandi and Fishman, 1998; Wolf et al., 1998). Accordingly, the clathrin-independent pathway used by GFP-TTC, appears to involve lipid microdomains. Analysis by confocal microscopy revealed morphologically two different labelings. Firstly, a GFP-TTC diffuse staining, which partially overlaps with the synaptic vesicle SV2 but also with the raft marker CT-b, indicating a mixing of synaptic vesicles and lipid rafts. Secondly, highly fluorescent domains, which are detected before and persist after the more diffuse pattern and that appear to be invaginations or infoldings of the synaptic membrane. These GFP-TTC patches contained only CT-b labeling. Indeed, lipid microdomains which play a role in cellular functions such as vesicular trafficking and signal transduction (Simons and Toomre, 2000), can move laterally and cluster into larger patches (Harder et al., 1998). They might also be specific zones of exocytosis in the presynaptic compartment, undergoing a rapid form of internal traffic in response to retrograde signaling from target cells. Similar infolding and cisternae structures have been described in frog motor nerve terminals which replesnish the pool of synaptic vesicles in a manner dependent upon neuronal activity (Richards et al., 2000). In CHO cells, tubular caveolae have also been described (Mundy et al., 2002).

Based on the kinetics of probes for NMJ localization, we observed different trafficking behaviours for GFP-TTC and CT-b. It has been postulated that targeting of toxin into the cell depends on the structure and function of endogenous ganglioside receptors, which could couple toxins to specific lipid raft microdomains (Wolf et al., 1998). Thus, in vivo, endogenous or injected BDNF might increase the amount of lipid microdomains containing TTC receptors. Tetanus toxin and cholera toxin bind to different gangliosides, known as GD1b/GT1b and GM1, respectively. Hence, the difference we observed in the dynamics of recruitment at the presynaptic motor nerve terminal may be relevant to different lipid microdomains having specific glycosphingolipids and protein composition. Neuronal membranes are rich in gangliosides and different microdomains are likely to co-exist on the cell surface. Indeed, Thy-1 and PrP prion protein, two functionally different GPI proteins, are found in adjacent microdomains (Madore et al., 1999). Similarly, syntaxins are concentrated in cholesterol-dependent microdomains, which are distinct from rafts containing GPI-linked proteins (Lang et al., 2001).

Like BDNF, NT-4 was also found to increase the concentration of GFP-TTC at the NMJ, whereas NGF and NT-3 had no effect. Since the TrkB receptor is specifically activated by BDNF and NT-4, TrkB activation might be involved in this neoronal trafficking. Interestingly, high-frequency neuronal activity and synaptic transmission have been shown to elevate the number of TrkB receptors on the surface of cultured hippocampal neurons (Du et al., 2000), apparently by recruiting extra TrkB receptors to the plasma membrane (Meyer-Franke et al., 1998). Moreover, TrkB is highly enriched in lipid microdomains from neuronal plasma membrane (Wu et al., 1997). However, no specific colocalization between GFP-TTC and TrkB or p-Trk receptors were detected at the NMJ. Thus, TrkB may act indirectly on the detected traffic at the presynaptic motor nerve membrane.

It is worth noting that the TTC fragment has been detected in cultured motoneurons in the same vesicles as $p75^{NTR}$ (Lalli and Schiavo, 2002). This colocalization may be explained by the tight association of $p_{75}^{NTR}$, which is expressed mainly during development and in pathological conditions, with GT1b ganglioside (Yamashita et al., 2002). Binding of neurotrophins to their Trk receptors leads to phosphorylation of tyrosine residues that are recognized by several intracellular signaling proteins. Such interactions lead to the activation, by means of a kinase cascade, of the MAP kinase, PI 3-kinase and phospholipase-C-γ pathways (for review see (Huang and Reichardt, 2003)). Many of the intermediates in these signaling cascades are also present in lipid rafts (Simons and Toomre, 2000; Tsui-Pierchala et al., 2002). Activation of PKA is required for translocation of activated $p75^{NTR}$ to lipid rafts (Higuchi et al., 2003). Similarly, the coreceptor GFRα1, which binds GDNF and thus allows activation of the c-RET tyrosine kinase receptor, localize to lipid rafts. GFRα1 recruits RET to lipid rafts after GDNF stimulation and results in strong and continuous signal transduction (Paratcha et al., 2001; Tansey et al., 2000).

Another neurotrophic factor, GDNF, also induced GFP-TTC localization at the NMJ. GDNF, however, activates a different receptor (i.e., a GFRa/cRET receptor) than BDNF and NT-4. Because BDNF/NT-4 and GDNF activate different receptors, we postulated that component(s) of their activation pathways may activate the trafficking of GFP-TTC receptors in specific lipid microdomains. Indeed, various stimuli can lead to internalization of caveolae, a specialized form of lipid rafts. Thus, simian virus 40 stimulates its internalization in caveolae and transport via caveosomes (Pelkmans et al., 2001). Similarly, the albumin-docking protein pg60 activates its transendothelial transport by interaction with caveolin-1 and subsequent activation of Src kinase signaling (Minshall et al., 2000). Recently, it has been reported that tetanus toxin can activate, through the TTC fragment, intracellular pathways involving Trk receptors, extracellular signal-regulated kinases (ERK) and protein kinase C isoforms (Gil et al., 2001; Gil et al., 2000; Gil et al., 2003). In this way, tetanus toxin could therefore autoactivate its neuronal endocytosis via an uncoated pathway rather than by clathrin-dependent pathway to avoid the lysosomal degradation.

Finally, we have demonstrated that GFP-TTC trafficking is regulated by neurotrophic factors. By visualization of GFP-TTC trafficking, our data show that BDNF can stimulate both clathrin-coated and uncoated endocytic pathways, presumably via TrkB activation. Since tetanus toxin, as other pathogens or toxins, uses constitutive mechanisms for its internalization and traffic in cells, we have been able to visualize with GFP-TTC, a physiological response to neurotrophic factors.

This aspect of the invention is further discussed in the following examples.

EXAMPLE 9

GFP-TTC Localization at the NMJ

Figure 6:
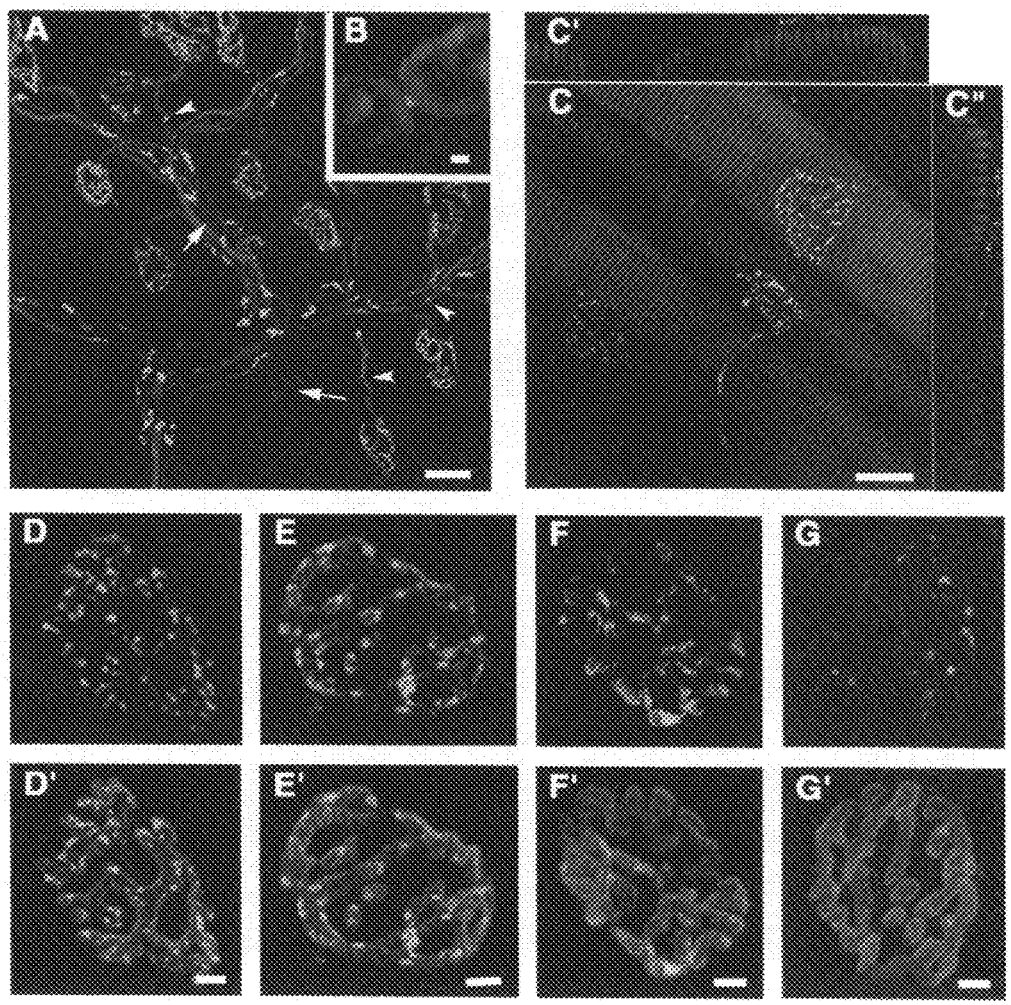
FIG. 6 shows the confocal immunofluorescence analysis of GFP-TTC membrane traffic at mature mouse LAL NMJs.

To determine the characteristics of the GFP-TTC distribution at the NMJ, a single injection of the GFP-TTC fusion protein was performed in the immediate vicinity of the Levatorauris longus (LAL) muscle and at various times after the injection, the LAL was removed and examined as a whole mount. As LAL is a thin and flat muscle consisting of only a few layers of fibers, the entirety of the neuromuscular preparation with associated nerves could be examined by confocal analysis (FIG. 6A). As shown in FIG. 6, GFP-TTC rapidly concentrates at the NMJ, as identified by the staining of muscle nicotinic acetylcholine receptors with TRITC-conjugated a-bungarotoxine (a-BTX). A patchy clustering of GFP-TTC was observed after approximately 5 min following the deposit of the fusion protein onto the surface of the LAL muscle (FIGS. 6D and D'). After 30 min, a more diffuse staining was observed that was distributed over the entire surface of the NMJ (FIGS. 6E and E'), and which persisted for about 2 h (FIGS. 6F and F'). Immunostaining experiments, performed with an antibody that recognizes troponin T confirmed that GFP-TTC is concentrated mainly in presynaptic motor nerve terminals of the NMJ (FIGS. 6C and C'). We could also detect a strong GFP-TTC labeling at the nodes of Ranvier of intramuscular myelinated axons and in sensory nerve fibers (FIGS. 6A and B; arrows and arrowheads respectively). It is likely that most of the GFP-TTC probe was internalized within 24 h, since only a few fluorescent patches persisted at the NMJ 24 h after its injection (FIGS. 6G and G').

EXAMPLE 10

Influence of BDNF on GFP-TTC Trafficking in Motor Nerve Terminals

To assess whether exogenously applied neurotrophins affected GFP-TTC recruitment in motor nerve terminals, increasing concentrations of BDNF (2.5-250 ng) were co-injected with GFP-TTC in the vicinity of LAL muscles, while control mice were injected with GFP-TTC alone. Mice were sacrificied and LAL muscles harvested 30 min after injection. GFP fluorescence was quantified by confocal microscopy analysis at NMJs, after identification by TRITC-a-BTX labeling. BDNF injection produced a statistically significant concentration-dependent enhancement of GFP-TTC fluorescence at the NMJ, with the highest effect obtained with 50 ng BDNF (FIG. 7B and Table 2) while higher doses (100 and 250 ng) resulted in weaker elevations in the level of GFP-TTC concentration at the NMJ ($1.72 \pm 0.12$ and $1.15 \pm 0.22$ fold respectively). The higher GFP-TTC axonal labeling observed at these higher doses (FIG. 7A, arrows), probably correlates to an enhanced internalization of the probe.

In TrkB mutant mice, a physiological phenotype in the facial nerve nucleus, which innervates LAL muscle has been reported (Klein et al., 1993; Silas-Santiago et al., 1997). To exclude the possibility that the BDNF effect observed could be LAL specific, a different muscle, the gastrocnemius, was also analyzed. Thirty minutes after injecting GFP-TTC ($\pm$BDNF 50 ng) in gastrocnemius, muscles were fixed, removed and serially sectioned. For each muscle, different serial sections were quantified for GFP-TTC fluorescence at the motor nerve terminals as described in material and methods. We found that the BDNF-dependent increase of GFP-TTC concentration at the NMJ, closely resembled that observed in LAL ($1.51 \pm 0.12$ fold increase vs $2.12 \pm 0.19$ respectively).

EXAMPLE 11

Influence of Other Neurotrophic Factors on GFP-TTC Localization at Motor Nerve Terminals We also examined the effect of five additional trophic factors on GFP-TTC localization at the NMJ, including the neurotrophins NT-3; NT-4 and NGF as well as the neurocytokine CNTF (Ciliary Neurotrophic Factor), a member of the LIF cytokine family, and GDNF (Glial-Derived Neurotrophic Factor), a member of the TGF-β superfamily (Table 2). Many BDNF actions in neurons are mediated via the high affinity receptor tyrosine kinase TrkB, which is also the receptor for NT4. Like BDNF, NT-4 also induced GFP-TTC localization at the NMJ (a $1.54 \pm 0.23$ fold increase). A level of induction similar to NT-4 was also observed for GDNF (Table 2). On the other hand, even at high concentrations, neither NGF, NT-3, nor CNTF exhibited a significant effect on GFP-TTC localization.

TABLE 2

Effect of various neurotrophic factors on nerve terminal's GFP-fluorescence level 30 min after in vivo GFP-TTC injection.

|  | Receptor | Relative increase in fluorescence level |
| --- | --- | --- |
| BDNF | TrkB | $2.12 \pm 0.19$** |
| NT-4 | TrkB | $1.49 \pm 0.23$** |
| NT-3 | TrkC | $0.94 \pm 0.05$ |
| NGF | TrkA | $1.06 \pm 0.06$ |
| CNTF | CNTFRα | $0.95 \pm 0.05$ |
| GDNF | GFRα/cRET | $1.51 \pm 0.02$* |

GFP-TTC was co-injected with increasing concentrations of neurotrophic factors and GFP fluorescence quantified 30 min after as previously described. Mean of relative increase of GFP fluorescence of 2 or 3 independent experiments are indicated. Maximum fold induction was obtained for 50 ng of neurotrophic factor injected except for NT-3 (2.5 ng).
**$P < 0.005$;
*$P < 0.05$ t-test vs control.

EXAMPLE 12

Comparison of Trk Receptors Distribution and GFP-TTC Localization at Motor Nerve Endings Detection of either TrkB mRNA or protein in adult skeletal muscle and motoneurons has been reported in several studies (Funakoshi et al., 1993; Gonzalez et al., 1999; Griesbeck et al., 1995; Yan et al., 1997). Since our results indicated that the BDNF effect on GFP-TTC localization is dependent on TrkB receptor activation, it was of interest to determine whether GFP-TTC colocalized with TrkB at the NMJ of LAL muscles. Consistent with previous studies (Gonzalez et al., 1999; Sakuma et al., 2001), TrkB immunostaining was confined to the NMJ (FIG. 8). In the presynaptic side, TrkB staining was adjacent to, but not colocalized to the clusters of GFP-TTC labeling. Similar results were also obtained with an antibody that recognizes the activated Trk receptors (p-Trk, data not shown). This observation suggests that the mechanism whereby BDNF has an influence on the concentration of GFP-TTC at the nerve terminals, does not involve a direct interaction between TrkB and GFP-TTC or its receptors.

EXAMPLE 13

Mechanisms Involved in BDNF Effect on GFP-TTC Concentration at the NMJ

Possible explanations for the BDNF-induced enrichment of GFP-TTC at the NMJ could involve an elevated rate of localization of the probe at the NMJ, and/or an increased neuronal endocytosis of the probe. Confocal analysis performed 5, 15, 30, 60 and 120 min after GFP-TTC injection (±BDNF 50 ng) showed maximal labeling intensity at 30 min with BDNF injection, whereas in controls, the maximal staining occurred at 1 h and reached a level lower than that obtained with BDNF co-injection. After the first hour, similar levels of GFP-TTC were recorded at the NMJ in both conditions (FIG. 9A). These results are in accordance with previous results in *Xenopus* nerve-muscle co-culture indicating a time-limiting effect of BDNF (Lohof et al., 1993).

In vitro, tetanus neurotoxin internalization in neurons appears to involve both coated and uncoated-vesicular pathways (Herreros et al., 2001; Matteoli et al., 1996). Experiments performed either in vitro on excised LAL muscles with the endocytic fluid marker RH414 (data not shown), or immunostained against the SV2 synaptic vesicle proteins (FIG. 9B) and synaptophysin (data not shown) showed some overlapping with GFP-TTC labeling, indicating that the endocytosis of GFP-TTC was in part via recycling of neuronal synaptic vesicles. To differentiate between clathrin-dependent and clathrin-independent endocytic pathways, we used treatment with botulinum neurotoxin serotype A (BoTx/A), which blocks neurotransmitter release and endocytosis in motor nerve terminals (de Paiva et al., 1999). When BoTx/A was applied 48 hours before GFP-TTC injection, the probe level at the NMJ was markedly decreased by 50% (FIG. 9C), indicating that both clathrin-dependent and independent pathways are used to a comparable degree.

Enhanced synaptic transmission produced by application of exogenous BDNF; NT-3 or NT-4 involves a potentiation of neurotransmitter release (Lohof et al., 1993; Stoop and Poo, 1996; Wang and Poo, 1997). The increasing amount of GFP-TTC at the NMJ induced by BDNF injection could therefore be due in part to an elevated recycling of synaptic vesicles. To explore this hypothesis, increased exocytosis and endocytosis of synaptic vesicles were induced by GFP-TTC injection in a high-potassium medium. Five minutes after injection, exposure to high $K^+$ medium or BDNF induced a similar increase of GFP-TTC level at the NMJ. However, after 30 min, the effect of high $K^+$ was no longer detectable, whereas maximal induction was reached with BNDF at this time (FIG. 9D). Finally, even after neurotransmitter release and synaptic vesicle recycling were blocked by BoTX/A, an increased GFP-TTC signal was induced by BDNF treatment (FIG. 9C) with an amplitude comparable to that recorded in the non-paralyzed control NMJ (2.05 fold increase vs 2.12 respectively). Taken together, these results indicate that BDNF enhances an alternative endocytic pathway that appears to involve uncoated vesicles.

EXAMPLE 14

Evidence for Association of GFP-TTC in Detergent-Insoluble Membrane at the Neuromuscular Junction Binding of TTC to plasma membranes involves association to polysialogangliosides GD1b and GT1b, as well as a N-glycosylated 15 kDa protein. These three components partition preferentially in membrane microdomains called rafts. In vitro, TTC has been shown to associate with such microdomains in NGF-differentiated PC12 cells and in cultured spinal cord neurons (Herreros et al., 2001; Vyas, 2001). To test in vivo whether GFP-TTC associated to lipid rafts, gastrocnemius muscles were submitted to detergent extraction to isolate lipid microdomains after GFP-TTC intramuscular injection. Twelve fractions from the discontinuous sucrose gradient were collected and analyzed for distribution of GFP-TTC.

Neurons do not contain caveolin or morphologically distinct caveolae (Anderson, 1998), but significant fractions of cholesterol and glycosphingolipids are found in detergent-insoluble complexes, which are indistinguishable using the criteria of detergent insolubility from those associated with caveolae (Schnitzer et al., 1995). Thus, caveolin 3, a specific muscular caveolar marker (Tang et al., 1996), was used to identify the detergent-resistant fractions. Immunoblot analysis revealed that GFP-TTC co-migrated with raft microdomains, which contain caveolin 3 (FIG. 10A).

To investigate whether the GFP-TTC patches observed in vivo in motor nerve terminals correspond to lipid microdomains, we performed co-staining with Alexa 594-conjugated cholera toxin-B fragment (CT-b). CT-b specifically binds to ganglioside GM1, which is enriched in cholesterol-rich membrane microdomains, and is commonly used as a marker for membrane rafts and caveolae (Orlandi and Fishman, 1998; Schnitzer et al., 1995; Wolf et al., 1998). GFP-TTC and Alexa 594-conjugated CT-b fragment were co-injected into the gastrocnemius and confocal analysis was performed 1; 3; 5; 9 and 24 h later, with the NMJ being identified by AlexaFluor 647-conjugated A-BTX (FIG. 10B). Although the GFP-TTC labeling of motor nerve terminals was easily visualized in less than the 5 min necessary to process the tissue (FIGS. 6D and D'), CT-b was detectable at the NMJ only several hours after injection (3-5 h). Thus, the dynamics of trafficking of CT-b and TTC receptors to active synapse are clearly different. However, after 5 h, the distribution obtained for CT-b was similar to GFP-TTC staining, as characterized by diffuse staining and patches having an extensive overlap of the staining patterns obtained with GFP-TTC, indicating a localization of the TTC probe in lipid microdomains in motor nerve endings (FIG. 10B). Twenty four hours after gastrocnemius injection, both toxins had been internalized since only few patches, most of them positive for both toxins, persisted at the NMJ (FIGS. 10B and C). At this time, GFP-TTC and CT-b staining were detected in the same motoneuron cell bodies in the ventral horn of the spinal cord, but in different vesicular compartments (FIG. 11). Taken together, these results indicate that GFP-TTC used different lipid microdomains for neuronal binding and/or internalization pathways than CT-b.

Materials and Methods

Antibodies and Reagents.

Rabbit anti-GFP polyclonal antibodies was obtained from Invitrogen (1:5000 dilution). Mouse monoclonal antibody against caveolin 3 was from Transduction Laboratories (1:500). The monoclonal anti-neurofilament 200 (clone NE14) and the rabbit polyclonal antitroponin T were obtained from Sigma. AlexaFluor 594-conjugated Cholera toxin subunit B (CT-b); AlexaFluor 488-conjugated goat-antirabbit IgG, AlexaFluor 647-conjugated a-bungarotoxin (a-BTX) and RH414 were obtained from Molecular Probes. Cy3-conjugated goat anti-rabbit IgG and Cy3-conjugated rat anti-mouse IgG were from Jackson Laboratories. TRITC-conjugated a-bungarotoxin was obtained from Calbiochem. The rabbit anti-TrkB (794) and the anti-p-Trk polyclonal antibody were obtained from SantaCruz. The monoclonal antibody against synaptic vesicle protein SV2, developed by K. Buckley, was obtained from the Developmental Studies Hybridoma Bank developed under the auspices of the NICHD and maintained by The University of Iowa, Department of Biological Sciences, Iowa City. Monoclonal antibody against synaptic vesicle synaptophysin protein was obtained from Chemicon. The goat anti-rabbit and anti-mouse IgG antibodies conjugated to horseradish peroxydase were obtained from Pierce as well as the SuperSignal detection reagent. Recombinant neurotrophic factors rat CNTF; human NT3; human NT4, human BDNF, human GDNF and purified mouse NGF 7S were purchased from Alomone labs. Neurotrophic factors were prepared as stock solutions (10 µg/ml) and kept in aliquots at −80° C.

In Vivo Intramuscular Injection.

Experiments were performed in accordance with French and European Community guidelines for laboratory animal handling. Six-week-old Swiss female mice were obtained from Charles River Breeding Laboratories. Intramuscular injections of β-gal-TTC, GFP-TTC fusion proteins, produced as previously described (Coen et al., 1997), or AlexaFluor 594-conjugated CT-b were intramuscular injected into the gastrocnemius muscle or subcutaneously in the immediate vicinity of the Levator auris longus (LAL) muscle on anesthetized mice. For fluorescence quantification, 25 µg of GFP-TTC fusion protein were injected in PBS in 50 µl final volume. For immunodetection or biochemical extraction, 50 µg of GFP-TTC probe were used. When co-injections with neurotrophic factors were performed, the volume injected was kept constant (50 µl). For injection in high $K^+$, a physiological solution containing 60 mM KCl was co-injected with the probe.

Botulinum Type-A toxin Injection.

*Clostridium botulinum* type-A toxin (BoTx/A) was injected subcutaneously as a single dose of 0.05 ml containing about 0.5 pg of the purified neurotoxin in the vicinity of the LAL muscle of female Swiss mice (body weight 24-27 g). 48 h after BoTx/A treatment, a time sufficient for inducing muscle paralysis in the LAL due to blockade of neurotransmitter release (de Paiva et al., 1999), GFP-TTC (25 μg) was injected associated or not with BDNF (50 ng) in the vicinity of the LAL muscle. Mice were killed by intracardial injection of PFA 4% 30 min after injection and LAL muscle harvested and processed for confocal analysis.

In vitro analysis of GFP-TTC localization and confocal acquisition.

LAL muscles with their associated nerves were isolated from female Swiss-Webster mice (20-25 g), killed by dislocation of the cervical vertebrae. LAL muscles were mounted in Rhodorsil$^R$-lined organ baths (2 ml volume) superfused with a standard oxygenated physiological solution of the following composition (mM): NaCl 154; KCl 5; $CaCl_2$ 2; $MgCl_2$ 1; HEPES buffer 5 (pH=7.4) and glucose 11. Muscles were loaded for 45 min in the dark and at room temperature with both 25 μg GFP-TTC and 30 μM of RH414, dissolved in standard solution or, for synaptic vesicle recycling, in high $K^+$ isotonic solution (with 60 mM KCl replacing 60 mM NaCl). Preparations were washed out of the GFP-TTC and RH414 dye, and rinsed several times with dye-free standard medium before being imaged with a Leica TCS SP2 confocal laser scanning microscope system (Leica Microsystems, Germany) mounted on a Leica DM-RXA2 upright microscope equipped with a x40 water immersion lens (Leica, NA 0.8). The confocal system was controlled through Leica-supplied software running on a Windows NT workstation.

Preparation of Detergent-Resistant Membrane (DRMs) Fractions and Western Blot.

Preparation of detergent-resistant membrane fractions is one of the most widely used methods for studying lipid rafts. Two hours after GFP-TTC injection (50 μg), mouse gastrocnemius muscle tissue was harvested, minced with scissors and homogenized in 2 ml of MES-buffered saline containing 1% (v/v) Triton X-100. Homogenization was carried out with a Polytron tissue grinder. After centrifugation at low speed for 5 min, supernatant was adjusted to 40% sucrose. A 5-30% linear sucrose gradient was formed above the homogenate and centrifuged at 39,000 rpm for 18 h in a SW41 rotor. Then, 11-12 fractions of 1 ml were collected from the top of the gradient and precipitated with 6.5% trichloroacetic acid in the presence of 0.05% sodium deoxycholate and washed with 80% cold acetone. Samples were analyzed by Western Blot after separating on a 4-15% SDS-PAGE followed by Western Blot. Membranes were probed first with polyclonal anti-GFP and monoclonal anti-caveolin 3 antibodies, and then incubated with goat anti-rabbit IgGs and goat anti-mouse IgGs antibodies conjugated with horseradish peroxydase. The SuperSignal (Pierce) was used to visualize the reaction.

Quantification of GFP-TTC Fluorescence Intensity at the NMJ.

After intracardiac perfusion and fixation, LAL muscles were harvested, washed in PBS for 20 min, stained with TRITC-conjugated a-bungarotoxin (TRITC-a-BTX) (2 μg/ml) for 45 min at 37° C. in PBS and washed twice in PBS. Images were acquired on an Axiovert 200M laser scanning confocal microscope (LSM-510 Zeiss; version 3.2) through a x40/1.2 water-immersion objective using LP560 and BP505-550 filters. The pinhole aperture was set to 1 airy unit, and images were digitized at 8-bit resolution into a 512×512 pixel array. To be able to compare the intensity of GFP staining between different experiments, laser illumination, photomultiplier gain in regard of linear response, and other acquisition variables were standardized. To quantify GFP-TTC localization at the NMJ, series of "look-through" projection (of MIP: Maximum Intensity Projection) was generated. Images from each NMJ were processed identically: NMJ surface area (in $\mu m^2$) was determined by TRITC-a-BTX labeling and GFP fluorescence global intensity (sum of each pixel intensity) was then measured only in this predefined area. This value, divided by the NMJ area yielded GFP fluorescence intensity per square micrometer, which thus defined the fluorescence level expressed as arbitrary units. For each condition, ~15 to 20 synapses were quantified and results were expressed as the mean±SD. Statistical significance was defined as p<0.05 using a two-tailed t test. Each experiment was repeated at least two or three times.

Analysis of Spinal Cord.

24 hours after β-gal-TTC or GFP-TTC and CT-b injection into the gastrocnemius muscle (50 µg each), mice deeply anesthetized were perfused intracardially with 4% PFA. The spinal cord was harvested and embedded in Tissue Tek embedding media after overnight incubation in 25% sucrose in PBS 0.1 M. Longitudinal cryostat sections (30 µm thickness) were cut and mounted onto coated slides.

X-gal Reaction.

X-gal reaction was performed as previously described (Coen et al., 1997).

EXAMPLE 15

Culture Preparation

Cortical tissues are dissected from newborn (P0-P2) Swiss mice. Dissociated cortical neurons are obtained by gentle treatment with 0.25% trypsin for 2 min. at RT, followed by 0.1 mg/ml DNase for 2 min. at RT. Cellular suspension is then washed with DMEM/F12 (Life Technologies, Cergy Pontoise, France) supplemented with 10% FBS, mechanically dispersed with Pasteur pipettes of decreasing calibers, and passed through a nylon filter (80 µm pore size; Millipore, Bedford, Mass.). Cells are plated in 35-mm, glass bottom plates (MatTek Co., Ashland, Mass.) at a density of 20,000 cells/cm$^2$, and cultured at 37 C in a water-saturated atmosphere of 95% air and 5% $CO_2$ for 14 days before experimental manipulation. Culture medium consists of. DMEM/F12 (Life Technologies) supplemented with 1% penicillin/streptomycin, and 100 µg/ml transferrin (Sigma-Aldrich, Lyon, France), 20 nM selenium (Sigma-Aldrich), 20 nM hydrocortisone (Sigma-Aldrich), 20 nM progesterone (Sigma-Aldrich). and 5 µg/ml insulin (Sigma-Aldrich) in order to enhance neuronal survival and suppress glial proliferation (Brunner, 1981). Culture medium is renewed only once, 24 h after plating the cells.

For organotypic slices, entire blocks of the brain are positioned ventrally under a McIlwain Tissue Chopper (Campden Instruments Ltd., UK) and 400-µm thick coronal slices from cortex are obtained. Carefully, slices are placed on collagen-coated, 3-µm pore size membranes (Transwell-Col; Corning B.V., Schiphol-Rijk, The Netherlands) and incubated in DMEM/F12 with 1% penicillin/streptomycin, and supplemented with the same compounds listed above for dissociated cell cultures. Medium level is adjusted to slightly above the collagen-coated membrane to keep a mixed phase of culture medium and gases, and is renewed twice a week. Slices are maintained for up to 14 days at 37 C (95% air and 5% $CO_2$).

EXAMPLE 16

Binding and Internalization of GFP-TTC

The hybrid protein reporter utilized in this invention, consisting of the jellyfish green fluorescent protein (GFP) bound to the non-toxic, C terminal fragment of tetanus toxin (TTC), was purified as described elsewhere with slight modifications (Coen et al., 1997). Briefly, E. coli strain SR3315 was transfected with pGEX:GFP-TTC plasmid and grown overnight at 32° C. in Luria-Bertani medium containing 100 µg/ml ampicillin. Protein expression was induced by incubation with 1 mM isopropyl β-D-thiogalactoside and 1 mM $MgCl_2$ for 2 hr. Bacteria were then centrifuged (20 min, 3,000 rpm), washed with lysis buffer [0.1 M Tris pH 7.8, 0.1 M NaCl, 10 mM EDTA, 4 mM 1,4-Dithio-DL-threitol, 20% glycerol, 1 mg/ml lysozyme and 100 µg/ml anti-protease mixture (Roche)], lysated in a French Press and spun at 30,000 rpm for 10 min. The supernatant was incubated with glutathione-Sepharose 4B (Stratagene) overnight at 4° C. and with gentle agitation. Afterwards, the matrix was washed with lysis buffer (without lysozyme and glycerol) and with PBS three times each. Cleavage of GFP-TTC-glutathione transferase was achieved by overnight incubation with 10 units/ml Thrombin (Sigma-Aldrich). Finally, GFP-TTC was concentrated by centrifugation at 5,000 rpm for 20 min in YM-50 centricon tubes (Amicon) and protein yield calculated by Bradford assay.

To study binding of GFP-TTC to the surface of dissociated cortical neurons, cells were exposed to 1.5 µg/ml GFP-TTC at 37° C. for 30 min. Cells were then washed with culture medium and placed on the temperature-controlled stage of a confocal laser scanning microscope (Axiovert 200M; Carl Zeiss) equipped with an argon-helium/neon laser built in multitrack operating mode and fitted with a Carl Zeiss Plan Apochromat 63X/NA 1.4 and 100X/NA 1.4 oil immersion objectives. Cells were then epiillumunited at 488 nm to acquire the GFP fluorescent signal with a 500-550 nm bandpass filter. Z-stack image acquisition was controlled by the package software LSM 510 (Carl Zeiss).

For colocalization experiments, cortical cells previously incubated with GFP-TTC were exposed to 500-nm or 100-nm diameter, carboxylate-modified, red fluorescent beads (580/605 nm FluoSpheres®; Molecular Probes) coated with brain-derived neurotrophic factor (BDNF; final concentration 50 ng/ml) as indicated in the kit instructions.

Green and red fluorophores were excited at 488 and 543 nm, respectively, and emitted fluorescent signals recorded in a Nipkow Disk confocal microscope (Perkin Elmer) equipped with a Plan Apochromat 63X/NA 1.4 or a Plan Apochromat 100X/NA 1.4 oil immersion objectives, or a confocal scanning microscope (Carl Zeiss) fitted with a Plan Apochromat 63X/NA 1.4 oil immersion objective.

Images of binding distribution at the cell membrane and intracellular mobilization of the hybrid protein were collected as 0.5-1 µm optical sections and projected offline in one single image. When the Nipkow Disk confocal was used, image acquisition was controlled by the package software Ultra-View (binning 2; Perkin Elmer). In studies designed to investigate at real time the effect of BDNF in the internalization of GFP-TTC within cortical neurons, cells were exposed to a 1-µl droplet of 1 µg/µl GFP hybrid protein (final concentration 1 µg/ml; Clontech), 1 µg/µl GFP-TTC (final concentration 1 µg/ml), or a mixture containing 1 µg/µl GFP-TTC and 50 ng/µl BDNF (final concentrations 1 µg/ml and 50 ng/ml, respectively). Subsequently, fluorescent images were captured every 1 min with a confocal laser scanning microscope (Carl Zeiss), and intracellular optical density was calculated for each time point. When possible, bright field images of the cells were captured at the beginning and at the end of each recording for reference purposes.

EXAMPLE 17

Intracellular Localization and Trafficking of GFP-TTC

To investigate the intracellular distribution and mobilization of GFP-TTC in dissociated cortical neurons, cells were transfected with a construct expressing TTC downstream of the coding sequence of the GFP (pGFP-TTC). Gene expression was under the regulation of the strong cytomegalovirus (CMV) promoter. Culture cells are transfected by incubation with a mix of Lipofectamine 2000 (BD Biosciences Clontech, Palo Alto, Calif.) and GFP-TTC reporter plasmid (3:1) at 37 C (95% air and 5% $CO_2$) for 24-48 h before visualization. For transfection of cortical cells in organotypic slices, these are exposed to $5\times10^8$ particles of a canine adenovirus (CAV-2; (5)) expressing GFP-TTC (generously provided by Dr. Eric J. Kremer, Molecular Genetic Institute, Montpellier, France) for 5 days at 37° C. (95% air and 5% $CO_2$).

Visualization of cortical neurons expressing the reporter construct GFP-TTC is assessed by placing the culture plates on the temperature-controlled stage of a confocal microscope equipped with an argon-helium/neon laser built in multitrack operating mode and fitted with a Plan Apochromat 63X/NA 1.4 objective (Carl Zeiss, Le Pecq, France). Epiillumination is set up at 488 nm to acquire the GFP fluorescent signal with a 500-550 nm band-pass filter. For visualization of GFP-TTC-expressing neurons in organotypic slices, multiphoton microscopy consisting of a Mira 900 Modelocked Titanium:Sappbire laser system (Coherent Inc., Santa Clara, Calif., USA) and a Verdi diode-pumped solid-state argon laser at 10 W (Coherent Inc.) is used. Image acquisition is assessed with an Achroplan 20X/NA, 0.75 objective (Carl Zeiss), using as excitation wavelength 880-920 nm depending on the depth of the focal penetration. To normalize image acquisition conditions for different set of experiments, 50 stacks (1024×1024 bits) per region of interest are captured setting up electronic gain and offset just below saturation level in the brightest confocal plane. The software package used for both cortical cells in culture and organotypic slice imaging is LSM 510 (Carl Zeiss).

Positive neurons were selected and scanned at high magnification (Plan Apochromat 63X/NA 1.4) to identify dendrites and postsynaptic structures. Images were acquired every 0.1-0.2 µm and three-dimensionally reconstructed in one single image.

Association of GFP-TTC-accumulating structures with functional presynaptic endings is determined by time-lapse imaging of FM1-43 binding concurrently to GEP-TTC visualization. The reason to use FM1-43 as presynaptic site marker is that this styryl dye has been shown to bind to membrane regions where membrane turnover is important (Cochilla, 1999). Inasmuch as presynaptic endings have a high exocytic/endocytic turnover due to neurotransmitter release, FM1-43 will bind earlier to these sites than other regions of the membrane. Culture GFP-TTC-expressing neurons are localized and dendritic spines chosen as regions of interest. Cells are then exposed to 2 µM FM 1-43 and regions of interest imaged every 3 s to visualize binding of FM1-43 over time.

Identification of endo/exocytic active structures was performed by FM1-43 (Molecular Probes) imaging studies. This lipophilic fluorescent dye has been used extensively for visualizing vesicle recycling in active zones of the membrane (Cochilla et al., 1999). Accordingly, the present invention used FM1-43 to label postsynaptic structures displaying an important membrane turnover. Thus, cortical neurons expressing GFP-TTC were exposed to 2 µM FM1-43 and monitored every 3 min with a laser scanning confocal microscope equipped with a spectral-deconvolution hardware able to calculate and separate emission spectra online from different fluorescent dyes in a particular sample.

In studies designed to investigate the intracellular pathways used by GFP-TTC to reach the postsynaptic terminals, cortical neurons were cotransfected with pGFP-TTC and pDsRed2-PSD-Zip45. The latter protein, also named as Homer 1 c and Vesl-1 L (Kato et al., 1998; Xiao et al., 1998), is an anchoring-scaffolding protein localized to excitatory postsynaptic sites (Okabe et al., 2001). EGFP coding region was excised from the coding sequence of pEGFP-C2-PSD-Zip45 (generously provided by Dr. Shigeo Okabe; Tokyo Dental and Medical University) and fused in frame to the coding sequence of DsRed2 to generate PSD-Zip45 N-terminally labeled with DsRed2.

Cotransfection of cortical neurons was performed by addition of 1 µg of each plasmid construct in 3 µl Lipofectamine 2000 (Clontech). After 24-48 hr incubation at 37° C. and 5% $CO_2$, positive neurons were imaged on a confocal microscope (Carl Zeiss). Optical section images were acquired every 0.2-0.5 µm, projected in a single image and the degree of colocalization of both proteins calculated offline.

EXAMPLE 18

Transneuronal Traffic of GFP-TTC

To determine the nature of GFP-TTC mobilization in cortical neurons, transfected cells are located in a high-speed image acquisition Nipkon Disk confocal microscope (binning 2; Perkin Elmer, Wellesley, Mass.) fitted with a Plan Apochromat 63X/NA 1.4 oil immersion objective, and locally treated with DMEM/F12 (control conditions) or 50 ng/ml brain-derived neurotrophic factor (BDNF) by means of a microinjection pipette (Eppendorf, Hamburg, Germany) placed nearby dendritic processes of the cell under observation. BDNF has been chosen as treatment inasmuch as this factor has been shown to modulate synapse activity (Kovalchuk, 2002) and remodeling of postsynaptic sites (Shimada, 1998). The same protocol is applied for cortical neurons expressing GEP alone in order to corroborate that the effect of BDNF is specific for ITC.

To ascertain whether changes in intracellular GFP-TTC pool after treatment with BDNF are actually related to secretory mechanisms, GFP-TTC-expressing cells are microinjected with a neutralizing antibody against SNAP-25. Inasmuch as this protein is a key constituent of the vesicle docking complex (Nehta, 1996), its blockage will arrest vesicle release and will allow the evaluation of the involvement of this secretory pathway in GFP-TTC egress. Cells are exposed to 488 nm laser illumination and 20 optical sections are collected every 6 s for as long as 2 min using a 500-550 um band-pass filter. Image acquisition is controlled by the package software UltraView (Perkin Elmer).

To elucidate the role of BDNF in the transynaptic traffic of the hybrid protein, dissociated cortical cells were transfected with the construct coding for GFP alone or GFP-TTC and 24-48 hr later, placed on a Nikon Disk confocal microscope (binning 2; Perkin Elmer). GFP- and GFP-TTC-expressing cells were located and locally treated with DMEM/F12 or 50 ng/ml BDNF by means of a microinjection pipette (Eppendorf) placed nearby the cell imaged. To determine whether the loss of intracellular fluorescence caused by BDNF was actually due to an increase of exocytosis or, on the other hand, to an intracellular degradation of the protein, the inventors immunodepleted SNAP-25 pool by microinjecting a neutralizing antibody raised against mouse SNAP-25 (Sternberg Monoclonals Inc.) and monitored the effect of local application of BDNF on the gradual disappearance of GFP-TTC. This antibody has been shown to completely and rapidly arrest stimulus-dependent exocytosis in synaptosomal preparations (Mehta et al., 1996) and hypothalamic neurons (Vazquez-Martinez et al., 2001 a; Vazquez-Martinez et al., 2001 b) by inhibiting SNAP-25 activity. Under these conditions, 20 optical sections of GFP-TTC-expressing neurons were collected every 6 s for as long as 2 min and intracellular fluorescence determined offline for each time point.

EXAMPLE 19

Quantification of GFP-TTC Accumulation Within Spines

To compare GFP-TTC accumulation in different intracellular regions, images are first processed with the deconvolution software Huygens 2.4.4 (Scientific Imaging Volume, Hilverson, The Netherlands) and projected in a single image. Random, 1-$\mu m^2$ regions of interest in dendritic shafts are selected and their integrated optical densities (IODs) calculated by ImageJ I.29x software (NIH, Bethesda, Md.) and compared to IODs obtained from dendritic spines. All data are normalized to the averaged IOD calculated from all the regions chosen within dendritic shafts and then statistically compared (Newman Keuls Multiple Comparison test; statistical significance considered if $P<0.05$). To determine whether the differences in IOD in these neuronal regions depend on TTC being specifically addressed or to an unexpected compartmentalization of GFP, the same analysis of intracellular fluorescence is carried out in cortical neurons transfected with a plasmid expressing only GFP using the same transfection protocol than that for pGFP-TTC.

EXAMPLE 20

Analysis of GFP-TTC Intracellular Mobilization

GFP-TTC intracellular mobilization is assessed by projecting Nipkon Disk confocal planes in single images and calculating IODs over time from whole cells and from randomly selected, 1 $\mu m^2$ regions of interest within dendritic processes using ImageJ I.29x. Data from DMEM/F12- and BDNF-treated cells are normalized to the first time points, averaged, and statistically compared (Newman Keuls Multiple Comparison test). GFP-TTC-expressing neurons microinjected with anti-SNAP-25 and GFP-expressing neurons treated with BDNF undergo the same analytical procedure.

The following results were obtained in the Examples 15-20.

GFP-TTC binds to Specific Microdomains of the Plasma Membrane that are Internalized Within Cortical Cells via BDNF-Induced Neuronal Activity First, the distribution pattern of the GFP-TTC was characterized in the membrane of dissociated cortical cells. After 30-min incubation, it was found that GFP-TTC binds to the cell surface of cortical neurons in a punctuated fashion all over the cell. Shown in FIG. 12A are two representative examples of cortical neurons exhibiting such a patched distribution of GFP-TTC. Accumulations of GFP-TTC in the membrane showed an averaged area of 1.16±0.11 $\mu m^2$ and a density of 3.50±0.71 patches/1 $\mu m^2$. Inasmuch as GFP-TTC accumulates in particular regions of the plasma membrane, but the recombinant GFP alone under the same experimental conditions does not, these results suggest the existence of specific membrane microdomains exhibiting high affinity for TTC in cortical neurons. Furthermore, it was found that these microdomains, which are dynamic structures that move on the surface of neuronal cells, act as endocytic carriers for GFP-TTC in an activity-dependent manner. Thus, in this invention it was found that a generalized membrane depolarization triggered GFP-TTC uptake in particular membrane microdomains. As illustrated in FIG. 12B, after local administration of 50 mM KCl membrane microdomains bearing GFP-TTC clusters moved towards distinct regions of the membrane, in which internalization occurred as discrete endocytic bursts, suggesting that the endogenous receptors of TTC are located in lipid rafts, that are membrane microdomains with a composition in cholesterol different to other regions of the membrane, which confers to these regions a certain mobility that can be regulated and addressed.

Previous studies have demonstrated that neurotrophin receptors, such as TrkB and p75, establish interactions with other receptors at the plasma membrane, including toxin-binding gangliosides, strengthening intracellular signaling cascades associated to neurotrophin-receptor phosphorylation (Chao, 2003). Therefore, it has been suggested that pathogens and neurotoxins may "hijack" existing endocytic machineries for neurotrophin receptors in order to invade the cells and to travel retrogradely long distances towards target tissues (Butowt and Von Bartheld, 2003).

Then, the next goal of this invention was to investigate the relationship that GFP-TTC internalization and neurotrophin receptor activation may exhibit. Using 500-nm fluorescent microspheres coated with brain-derived neurotrophic factor (i.e. BDNF), it was found that the aggregations of GFP-TTC at the plasma membrane were often in intimate contact with fluorescent beads, thereby indicating that, prior to internalization, TTC-binding receptors reside in membrane microdomains adjacent to BDNF receptors (FIG. 13A).

Inasmuch as BDNF enhances quantal neurotransmitter release and, consequently, synaptic vesicle retrieval (Tyler et al., 2002; Tyler and Pozzo-Miller, 2001), it was then considered whether this neurotrophic factor is involved in GFP-TTC uptake within cortical neurons. In contrast to GFP-TTC alone, cells exposed to 50 ng/ml BDNF in the presence of GFP-TTC exhibited within 1 minute of treatment a 10-fold increase in intracellular GFP fluorescence that persisted throughout the duration of the experiment (FIG. 13B). These results indicate that BDNF-receptor activation represents a key component of the activity-dependent internalization of GFP-TTC within cortical neurons, likely due to an enhanced endocytic vesicle recycling at active zones.

GFP-TTC travels retrogradely from presynaptic sprouts to the cell soma and from it to postsynaptic sites using similar pathways to those used by activated BDNF receptors and postsynaptic density proteins, respectively Next, to investigate the intracellular trafficking of GFP-TTC in real time, time-lapse monitoring of intracellular GFP-TTC mobilization was performed concurrently with the retrograde transport of activated BDNF receptors by high-speed confocal Nipkow scanning microscopy. To do this, cells were incubated with 100 nm fluorescent beads (which are small enough to be actively endocytosed by cells as opposed to the 500 nm beads) coated with BDNF in combination with GFP-TTC, and their intracellular transport was recorded every 30 s for as long as 30 min. As illustrated in the representative example shown in FIG. 14A, BDNF-coated beads were often in the proximity of GFP-TTC intracellular clusters. Time-lapse monitoring revealed that both proteins followed similar intracellular retrograde paths to reach the cell soma, as assessed by a particle tracking plug-in developed by Jeffrey Kuhn, University of Texas, for ImageJ I.29x (FIG. 14B). Furthermore, velocities calculated in function of the distance crossed by fluorescent clusters were similar for both GFP-TTC and BDNF-coated beads (1.73±0.37 vs. 1.24±0.18 $\mu m/min$, respectively), and diffusion coefficients were 20 and 25 times slower than the diffusion coefficients expected in case of intracellular Brownian motion. Thus, these findings indicate that, within cells, free movement of these proteins is severely restricted by what appears to be a common intracellular retrograde transport mechanism. However, the fact that a perfect overlapping of green and red fluorescent signals within the cells was not found and that transport of GFP-TTC and BDNF-coated beads was often independent, suggests that GFP-TTC and activated BDNF receptors are actually confined within separate trafficking vesicles, which may be the result of different endocytic pathways.

The traffic of GFP-TTC from the cell soma to postsynaptic sites was then investigated. First, cortical neurons were transfected with a plasmid construct coding for GFP in tandem with the sequence of TTC and optical sections of distant dendritic processes were captured by laser scanning confocal microscopy. It was found that the GFP-TTC produced by neurons accumulated in round, spine-like structures of 0.99±0.06 µm diameter (FIG. 15A).

To estimate the exocytic/endocytic activity in these neuronal structures, GFP-TTC-expressing cortical neurons were exposed to the styryl dye FM1-43 and its binding was monitored over time to active zones. Shown in FIG. 15B is a representative example of the distribution of FM1-43 fluorescence after 30 min incubation. As illustrated, the dye clustered in discrete regions of neuronal processes morphologically similar to postsynaptic spines (i.e. round protrusions with a diameter of 0.92±0.04 µm).

Moreover, time-lapse experiments revealed that dendritic protrusions accumulating GFP-TTC were the first targets for FM1-43 binding. Represented in FIG. 15C are time-sequence images at high magnification of a dendritic protrusion that accumulates GFP-TTC. FM1-43 added into the culture medium began to accumulate in certain regions of dendritic protrusions preferentially than in other regions of the plasma membrane, thereby indicating that these sites represent zones with a high exocytic/endocytic turnover.

In view of these findings, the next question raised was how the probe expressed by these neurons is localized specifically to these postsynaptic structures. It was thought that GFP-TTC could parasitize intracellular trafficking pathways used by anchoring-scaffolding proteins that are localized specifically to postsynaptic densities (PSD). This family of proteins comprises PSD proteins containing interacting motifs, which are critical for specific localization of particular receptors in the PSD. To date, the best documented molecular organization of PSD proteins is that of the NMDA-type glutamate receptor-interacting PSD-95 (Sheng, 2001). However, in the present invention, a recently isolated member of the HomerNesl family was chosen, named PSD-Zip45 (also referred as Homer 1c and Vesl-1 L (Kato et al., 1998; Xiao et al., 1998)), which, similarly to GFP-TTC, undergoes a rapid redistribution towards postsynaptic structures depending on neuronal activity. In contrast, PSD-95 forms stable clusters over periods of a few hours (Okabe et al., 2001). The activity-dependent addressing of this structural protein to postsynaptic spines may indicate the existence of a relationship between the transport mechanisms used by both proteins to reach these structures.

To examine this possibility, cells were cotransfected with pGFP-TTC and pDsRed2-PSD-Zip45 reporter constructs and monitored for intracellular distribution of both proteins. Shown in FIG. 16 are two examples of cortical cells expressing both GFP-TTC and DsRed2-PSD-Zip45 proteins. Although most of the intracellular fluorescence from GFP-TTC is diffuse, there are regions of the cell where the probe accumulates. These accumulations are not the result of probe precipitation inasmuch as cortical cells transfected with a construct expressing GFP alone and imaged after a similar incubation time did not display such an intracellular distribution of the fluorescent signal. Furthermore, intracellular accumulations of GFP-TTC colocalized strongly with PSD-Zip45 clusters within cell somas as well as dendritic projections, thereby indicating that both proteins share common trafficking pathways in order to reach postsynaptic regions.

GFP-TTC is Exocytosed from Cortical Cells Via a BDNF-Dependent Process

To date, there is a growing body of evidence indicating that BDNF, as well as other neurotrophins, exerts its effect not only in a retrograde fashion, but can also function as an anterograde factor, thereby affecting the postsynaptic cell as well (Heerssen and Segal, 2002). In the latter, it has been demonstrated that local application of BDNF causes $Ca^{2+}$ transients in adjacent spines, leading to a rapid and robust induction of long-term potentiation (Kovalchuk et al., 2002). Given this, next explored was the possibility that BDNF may also play a role in transynaptic transport of GFP-TTC from postsynaptic to presynaptic neurons. To do this, the above-mentioned microinjection system was used to eject small amounts (in the order of picoliters) of BDNF nearby GFP-TTC-expressing cells, and, over time, changes in intracellular fluorescence were monitored (FIG. 17A).

Using this experimental approach, it was found that BDNF induces a gradual loss of intracellular fluorescence, which reached significant levels within 12 s after BDNF administration (FIG. 17B). Furthermore, the calculated time required for a cell to lose 50% of its intracellular fluorescent level was 7-fold faster in the presence than in the absence of BDNF (10.1±2.2 min vs. 69.6±29.4, respectively; $P<0.05$, Newman-Keuls test).

To determine the specificity of BDNF inducing GFP-TTC exocytosis, the inventors proceeded to expose to BDNF cells transfected with a construct coding for GFP alone and they analyzed the variations of intracellular fluorescence after the treatment. Under these conditions, BDNF administration resulted in a slow decay of intracellular fluorescence similar to that observed when the GFP-TTC-expressing cells were exposed to culture medium (loss of 50% of intracellular fluorescence in 71.53±27.29 min), indicating that BDNF modulates specifically the exocytic machinery used by GFP-TTC to leave the cell. However, to discard the possibility that loss of intracellular fluorescence may be caused by fast degradation of the protein instead of increased exocytic turnover, SNAP-25, a protein critical for fusion of vesicles to the cell membrane (Mehta et al., 1996), was immunoneutralized by microinjection of a monoclonal antibody within GFP-TTC-expressing neurons prior to BDNF administration. By using this approach, it was found that, after blockage of SNARE-dependent exocytosis, the effect of BDNF on the decrease of intracellular fluorescence was severely reduced, but not completely inhibited (FIG. 17). Although one can not rule out the possibility that the efficiency of the anti-SNAP-25 antibody injection in blocking stimulus-dependent exocytosis was not 100%, several studies have reported that this antibody inhibits completely exocytosis from synaptosomal preparations (Mehta et al., 1996) and hypothalamic neurons (Vazquez-Martinez et al., 2001 a; Vazquez-Martinez et al., 2001b) in a very rapid and precise manner. Thus, it is suggested that BDNF would stimulate GFP-TTC exocytosis in dissociated cortical cells by SNARE-dependent as well as by SNARE-independent mechanisms.

Use of GFP-TTC as Marker of Functional Postsynaptic Spines

Figure 15D:
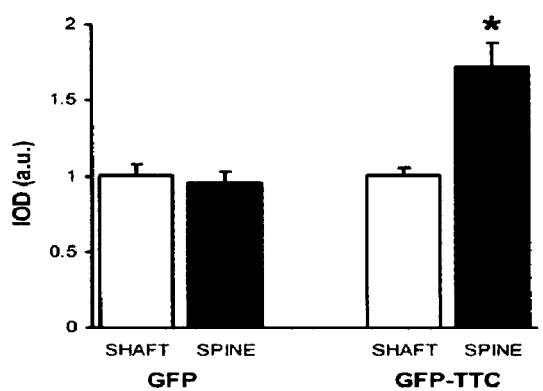

FIG. 15 illustrates the intracellular distribution of GFP-TTC in dendritic arborizations. As shown in FIG. 15A, GFP- TTC labeling is predominantly accumulated in round, spiny dendritic protrusions of about 1 μm² area in dissociated cortical neurons (left panels), as well as in cortical neurons within thick organotypic slices (right panels). Moreover, averaged GFP-TTC fluorescent intensity in these structures is about 70% higher than in regions of similar sizes chosen from dendritic shafts, whereas averaged GFP fluorescent signals are similar in both neuronal compartments (FIG. 15D).

The assembly of these results indicates that GFP-TTC protein accumulates in dendritic spines. The capacity of GFP-TTC to seek these postsynaptic structures can be used as a novel approach to visualize them directly by optical microscopy. However, as depicted in the confocal micrographs, GFP-TTC intracellular fluorescence distributes in a diffuse manner, likely due to an overexpression of the GFP-TTC gene driven by the strong CMV virus promoter. This caveat makes necessary the use of offline quantitative imaging processing to determine regions of GFP-TTC accumulation. Notwithstanding, the simplicity of the mathematical process that follows image acquisition and the availability of user-free, Java-based software packages for image processing (i.e. ImageJ I.29x) make of this approach a simple and rapid method for offline quantification of dendritic spines in particular brain regions under experimental and/or pathological conditions.

Although the averaged GFP-TTC fluorescent intensity is elevated in the dendritic spines of a given GFP-TTC-expressing neuron, not all of them accumulate the probe. Approximately, 30% of the dendritic spines examined show a similar or lower fluorescent level than the randomly selected shaft regions. This appears to be the result of the functional state of these structures depending on whether they are forming synaptic connections with presynaptic terminals or not. This is shown in FIG. 15C, in which the time-course of FM1-43 binding to a presynaptic site associated with a GFP-TTC-accumulating postsynaptic spine is illustrated. These results confirm that GFP-TTC is specifically addressed to those postsynaptic spines located in physical proximity with presynaptic terminals displaying high exocytic/endocytic turnover. Thanks to this characteristic of GFP-TTC, this invention provides for the use of this probe for evaluating the state of networking activity in dissociated neurons, organotypic slices, or even living animals. To mention an example, by using GFP-TTC-CAV-2 adenovirus transduction combined with multiphoton confocal microscopy, it would be possible to assess the number of functional synaptic connections in thick living brain slices and compare it with that estimated from model knockout animals that mimic symptomatologies of certain neurodegenerative diseases, such as Alzheimer's and Parkinson's diseases, as well as other brain dysfunctions characterized for an alteration in synaptic contact arrangement.

Use of GFP-TTC for Pharmacological Screening

It has recently been demonstrated that GFP-TTC undergoes a retrograde transport from the peripheral to the central nervous system (Coen. 1997, Maskos 2002). This traffic has been shown to depend on neuronal activity at the neuromuscular junction inasmuch as it is blocked by pharmacological treatment with tetrodotoxin (Miana-Mena, 2002). Given this, it is reasonable to think that GFP-TTC mobilization and transcytosis are regulated processes. Accordingly, treatment of GFP-TTC-expressing cells with agents affecting neuronal activity would alter GFP-TTC egress from the postsynaptic neuron. This is shown in FIG. 19A, in which the time-course profiles of GFP-TTC intracellular fluorescence alter local treatment with BDNF are illustrated. When whole-cells are considered (FIG. 19A left panel), BDNF induces an intracellular fluorescence decay 6-fold higher than the vehicle 2 min. after treatment. However, in distal regions of dendritic processes, loss of intracellular GFP-TTC is more evident than in whole cells, reaching fluorescence decay values 23-fold higher than in control conditions. In FIG. 19B, representative examples of cells treated with vehicle (top panels) and BDNF (bottom panels) are shown. This observation indicates that stimulus-dependent mobilization of GFP-TTC is more rapid in dendritic processes than in cell bodies, thereby supporting that this probe is released predominantly from postsynaptic regions to cross synapses to interconnected higher-order neurons.

The characteristic of GFP-TTC to be released from postsynaptic neurons via activity-dependent mechanisms can serve to screen the effects of endogenous modulators of neuronal activity and pharmacological drugs in complex neuronal networks. This invention is illustrated with BDNF, but the same protocol can be easily modified and applied for other substances of interest thought to alter the overall synaptic activity in particular brain regions.

REFERENCES

The following publications, which have been cited herein, are relied upon and incorporated by reference in their entireties herein.

1. Eisel, U., Jarausch, W., Goretzki, K., Henschen, A., Engels, J., Weller, U., Hudel, M., Habermann, E. & Niemann, H. (1986) *EMBO J.* 5, 2495-2502.
2. Fairweather, N. F. & Lyness, V. A. (1986) *Nucleic Acids Res.* 14, 7809-7812.
3. Montecucco, O. & Schiavo, G. (1995) *Quart. Rev. Biophys.* 28, 423-472.
4. Schwab, M. E. & Thoenen, H. (1976) *Brain Res.* 105, 213-227.
5. Schwab, M. E. & Thoenen, H. (1977) *Brain Res.* 122, 459-474.
6. Price, D. L., Griffin, J. W. & Peck. K. (1977) *Brain Res.* 121, 379-384.
7. Bizzini, B., Stoeckel, K. & Schwab, M. (1977) *J. Neurochem.* 28, 529-542.
8. Evinger, O. & Erichsen, J. T. (1986) *Brain Res.* 380, 383-388.
9. Fishman, P. S. & Carrigan, D. R. (1987) *Brain Res.* 406, 275-279.
10. Manning, K. A., Erichsen, J. T. & Evinger, 0. (1990) *Neurosci.* 34, 251-263.
11. Halpern, J. L., Habig, W. H., Neale, E. A. & Stibitz, S. (1990) *Infection and Immunity* 58, 1004-1009.
12. Bizzini, B., Grob, P., Glicksman, M. A. & Akert, K. (1980) *Brain Res.* 193, 221-227.
13. Dobrenis, K., Joseph, A. & Rattazzi, M. G. (1992) *Proc. Natl. Acad. Sci. USA* 89, 2297-2301.
14. Fishman, P. S. & Savift, J. M. (1989) *Exp. Neurol.* 106, 197-203.
15. Beaude, P., Delacour, A., Bizzini, B., Domuado, D. & Remy, M. H. (1990) *Biochem.* 271, 87-91.
16. Francis, J. W., Hosler, B. H., Brown, R. H., Jr. & Fishman, P. S. (1995) *J. Biol. Chem.* 270, 15434-15442.
17. Fellous. M., Gunther, E., Kemler, R., Weils, J., Berger, R., Guenet, J. L., Jakob, H. & Jacob, F. (1978) *J. Exp. Med.* 148, 58-70.
18. Jakob, H. & Nicolas, J. F. (1987) *Methods Enzymol.* 151, 66-84.
19. Whitehouse, R. L. S., Benichou, J. O. & Ryter, A. (1977) *Biol. Cell.* 30, 155-158.

20. Wojcik, B. E., Nothias, F., Lazar, M., Jouin, H., Nicolas, J. F. & Peschanski, M. (1993) *Proc. Natl. Acad. Sci. USA* 90, 1305-1309.
21. Price, D. L., Griffin, J. Young, A. Peck, K. & Stocks, A. (1975) *Science* 188, 945-947.
22. Matteoli, M., Verderio, C., Rossetto, O., Iezzi, N., Ooco. S. Schiavo, G. & Montecucco, G, (1996) *Proc. Natl. Acad. Sci. USA* 93, 13310-13315.
23. Stockel, K., Schwab, M. & Thoenen, H. (1975) *Brain Res.* 99, 1-16.
24. Ugolini, G. (1995a) in *Viral Vectors: Gene Therapy and Neuroscience Applications*, eds. Loewy, A. D. & Kaplift M. G. (New York: Academic Press), pp. 293-317.
25. Ugolini, G. (1995b) *The Journal of Comparative Neurology* 356, 457-480.
26. Borke, R. C., Nau, M. E. & R. L Ringler, J. (1983) *Brain Research* 269, 47-55.
27. Horst, G. T. T., Copray, J. C. V. M., liem, R. S. B. & Willigen, J. D. V. (1991) *Neuroscience* 40, 735-758.
28. O'Reilly, P. M. R. & Fitzgerald, M. J. T. (1990) *J. Anat.* 172, 227-243.
29. Chalfie, M. Tu, Y., Euskirchen, G., Ward, W. W. & Prasher, D. C. (1994) *Science* 263, 802-805.
30. Miesenbock, G. & Rothman, J. E. (1997) *Proc. Natl. Acad. Sci. USA* 94, 3402-3407.
31. Le Mouellic, H., Lallemand, Y. & BrOlet, P. (1990) *Proc. Natl. Acad. Sci. USA* 87, 4712-4716.
32. Le Mouellic, H., Lallemand, Y. & Brûlet, P. (1992) *Cell* 69, 251-264.
33. Mombaerts, P., Wang, F., Dulac, C. Chao, S. K., Nemes, A., Mendelsohn, M., Edmondson, J. & Axel, R. (1996) *Cell* 87, 675-686.
34. Mountford, P. S. & Smith, A. G. (1995) *Trends Genet.* 11, 179-184.
35. Rosen, D. R. & al (1993) *Nature* 362, 59-62.
36. Lefebvre, S., Büglen, L., Reboullet, S. Clermont, O., Bûrlet, P., Viollet, L, Benichou, B., Cruaud, O., Millasseau, P., Zeviani, M., Paslier, D. L., Frézal, J., Cohen, D., Weissenbach, J., Munnich, A. & Melki, J. (1995) *Cell* 80, 155-165.
37. Roy, N. & al (1995) *Cell* 80, 167-178.
38. Wolfe, J. H., Deshmane, S. L. & Fraser, N. W. (1992) *Nature genetics* 1, 379-384.
39. Sango, K., Yamanaka, S., Hoffmann, A., Okuda, Y., Grinberg, A., Westphal, H., McDonald, M. P., Crawley, J. N., Sandhoff, K., Suzuki, K. & Proia, R. L. (1995) *Nature Genetics* 11, 170-176.
40. Duarte, R. G. (1995) *Neurologia* 1, 56-61.
41. Ghadge, G. D., Roos, R. P., Kang, U. J., Wollmann, R., Fishman, P. S., Kalynych, A M., Barr, E. & Leiden, J. M. (1995) *Gene Therapy* 2, 132-137.

Anderson, R. G. W. 1998. The caveolae membrane system. *Annu. Rev. Biochem.* 67:199-225.

Bothwell, M. 1995. Functionnal interactions of neurotrophins and neurotrophin receptors. *Annu. Rev. Neurosci.* 18:223-225.

Coen, L., R. Osta, M. Maury, and P. Brulet. 1997. Construction of hybrid proteins that migrate retrogradely and transynaptically into the central nervous system. *Proc. Natl. Acad. Sci. USA.* 94:9400-9405.

de Paiva, A. M., F. A. Meunier, J. Molgo, R. Aoki, and J. O. Dolly. 1999. Functional repair of motor endplates after botulinum neurotoxin type A poisoning: biphasic switch of synaptic activity between nerve sprouts and their parent terminals. *Proc. Natl. Acad. Sci. USA.* 96:3200-3205.

Du, J., L. Feng, F. Yang, and B. Lu. 2000. Activity and $Ca^{2+}$-dependent modulation of surface expression of brain-derived neurotrophic factor receptors in hippocampal neurons. *J. Cell Biol.* 150:1423-1434.

Funakoshi, H., N. Belluardo, E. Arenas, Y. Yamamoto, A. Casabona, H. Persson, and C. F. Ibanez. 1995. Muscle-derived neurotrophin-4 as an activity-dependent trophic signal for adult motor neurons. *Science.* 268:1495-1499.

Funakoshi, H., J. Frisen, G. Barbany, T. Timmusk, O. Zachrisson, V. M. K. Verge, and H. Persson. 1993. Differential expression of mRNAs for neurotrophins and their receptors after axotomy of the sciatic nerve. *J. Cell Biol.* 123: 455-465.

Gil, C., I. Chaib, J. Blasi, and J. Aguilera. 2001. Hc fragment of tetanus toxin activates protein kinase C isoforms and phosphoproteins involved in signal transduction. *Biochem. J.* 356:97-103.

Gil, C., I. Chaib, P. Pellicioni, and J. Aguilera. 2000. Activation of signal transduction pathways involving TrkA, PLCγ, PKC isoforms and ERK-1/2 by tetanus toxin. *FEBS.* 481:177-182.

Gil, C., I. Chaib-Oukadour, and J. Aguilera. 2003. C-terminal fragment of tetanus toxin heavy chain activates Akt and MEK/ERK signaling pathways in a Trk receptor-dependent manner in cultured cortical neurons. *Biochem. J.* 373: 613-620.

Gonzalez, M., F. P. Ruggiero, Q. Chang, Y.-J. Shi, M. M. Rich, S. Kraner, and R. J. Balice-Gordon. 1999. Disruption of TrkB-mediated signaling induces disassembly of postsynaptic receptor clusters at neuromuscular junction. *Neuron.* 24:567-583.

Griesbeck, O., A. S. Parsadenian, M. Sendtner, and H. Thoenen. 1995. Expression of neurotrophins in skeletal muscle: quantitative comparison and significance for motoneuron survival and maintenance of function. *J. Neurosci. Res.* 42:21-33.

Harder, T., P. Scheiffele, P. Verkade, and K. Simons. 1998. Lipid domain structure of the plasma membrane revealed by patching of membrane components. *J. Cell Biol.* 141: 929-942.

Herreros, J., T. Ng, and G. Schiavo. 2001. Lipid rafts act as specialized domains for tetanus toxin binding and internalization into neurons. *Mol. Biol. Cell.* 12:2947-2960.

Higuchi, H., T. Yamashita, H. Yoshikawa, and M. Tohyama. 2003. PKA phosphorylates the p75 receptor and regulates its localization to lipid rafts. *Embo J.* 22:1790-1800.

Huang, E. J., and L. F. Reichardt. 2003. Trk receptors: roles in neuronal signal transduction. *Annu. Rev. Biochem.* 72:609-642.

Klein, R., R. J. Smeyne, W. Wurst, L. K. Long, A. B. A, A. L. Joyner, and M. Barbacid. 1993. Targeted disruption of the trkB neurotrophin receptor gene results in nervous system lessions and neonatal death. *Cell.* 75:113-122.

Lalli, G., and G. Schiavo. 2002. Analysis of retrograde transport in motor neurons reveals common endocytic carriers for tetanus toxin ans neurotrophin receptor $p75^{NTR}$ *J. Cell Biol.* 156:233-239.

Lang, T., D. Bruns, D. Wenzel, D. Riedel, P. Holroyd, C. Thiele, and R. Jahn. 2001. SNAREs are concentrated in cholesterol-dependent clusters that define docking and fusion sites for exocytosis. *Embo J.* 20:2202-2213.

Lohof, A. M., N. Y. Ip, and M. M. Poo. 1993. Potentiation of developing neuromuscular synapses by the neurotrophins NT-3 and BDNF. *Nature.* 363:350-353.

Madore, N., K. L. Smith, C. H. Graham, A. Jen, K. Brady, S. Hall, and R. Morris. 1999. Functionally different GPI proteins are organized in different domains on the neuronal surface. *Embo J.* 18:6917-6926.

Maskos, U., K. Kissa, C. Saint Cloment, and P. Brûlet. 2002. Retrograde trans-synaptic transfer of green fluorescent protein allows the genetic mapping of neuronal circuits in transgenic mice. *Proc. Natl. Acad. Sci. USA*. 95:10120-10125.

Mafteoli, M., C. Verderio, O. Rossetto, N. Iezzi, S. Coco, G. Schiavo, and C. Montecucco. 1996. Synaptic vesicle endocytosis mediates the entry of tetanus neurotoxin into hippocampal neurons. *Proc. Natl. Acad. Sci. USA*. 93:13310-13315.

McAllister, A. K., L. C. Katz, and D. C. Lo. 1999. Neurotrophins and synaptic plasticity. *Annu. Rev. Neurosci.* 22:295-318.

Meyer-Franke, A., G. A. Wilkinson, A. Kruttgen, M. Hu, E. Munro, M. G. J. Hanson, L. F. Reichardt, and B. A. Barres. 1998. Depolarization and cAMP elevation rapidly recruit TrkB to the plasma membrane of CNS neurons. *Neuron*. 21:681-693.

Miana-Mena, F. J., S. Roux, J.-C. Bénichou, R. Osta, and P. Brûlet. 2002. Neuronal activity-dependent membrane traffic at the neuromuscular junction. *Proc. Natl. Acad. Sci. USA*. 99:3234-3239.

Minshall, R. D., C. Tiruppathi, S. M. Vogel, W. D. Niles, A. Gilchrist, H. E. Hamm, and A. B. Malik. 2000. Endothelial cell-surface gp60 activates vesicle formation, and trafficking via Gi-coupled Src kinase signaling pathway. *J. Cell Biol*. 150:1057-1069.

Mundy, D. I., T. Machleidt, Y. S. Ying, R. G. W. Anderson, and G. S. Bloom. 2002. Dual control of caveolar membrane traffic by microtubules and the actin cytoskeleton. *J. Cell Science*. 115:4327-4339.

Orlandi, P. A., and P. H. Fishman. 1998. Filipin-dependent inhibition of cholera toxin: evidence for toxin internalization and activation through caveolae-like domain. *J. Cell Biol*. 141:905-915.

Paratcha, G., F. Ledda, L. Baars, M. Coulpier, V. Besset, J. Anders, R. Scott, and C. F. Ibanez. 2001. Released GFRalpha 1 potentiates dowstream signaling, neuronal survival, and differenciation via a novel mechanism of recruitment of c-Ret to lipid rafts. *Neuron*. 29:171-184.

Pelkmans, L., J. Kartenbeck, and A. Helenius. 2001. Caveolar endocytosis of simian virus 40 reveals a new two-step vesicular-transport pathway to the ER. *Nat. Cell Biol*. 3:473-483.

Poo, M. M. 2001. Neurotrophins as synaptic modulators. *Nature Rev. Neurosci.* 2:24-32.

Richards, D. A., C. Guatimosim, and W. J. Betz. 2000. Two endocytic recycling routes selectively fill two vesicle pools in frog motor nerve terminals. *Neuron*. 27:551-559.

Sakuma, K., K. Watanabe, M. Sano, I. Uramoto, H. Nakano, Y.-J. Li, S. Kaneda, Y. Sorimachi, K. Yoshimoto, M. Yasuhara, and T. Totsuka. 2001. A possible role for BDNF, NT-4 and TrkB in the spinal cord and muscle of rat subjected to mechanical overload, bupivacaine injection and axotomy. *Brain Res*. 907:1-19.

Schnitzer, J. E., D. P. McIntosh, A. M. Dvorak, J. Liu, and P. Oh. 1995. Separation of caveolae from associated microdomains of GPI-anchored proteins. *Science*. 269:1435-1439.

Silas-Santiago, I., A. M. Fagan, M. Garber, B. Fritzsch, and M. Barbacid. 1997. Severe sensory deficits but normal CNS development in newborn mice lacking TrkB and TrkC tyrosine protein kinase receptors. *Eur. J. Neurosci.* 9:2045-2056.

Simons, K., and D. Toomre. 2000. Lipid rafts and signal transduction. *Nat. Rev. Mol. Cell Biol*. 1:31-40.

Stoop, R., and M. M. Poo. 1996. Synaptic modulation by neurotrophic factors: differential and synergistic effects of brain-derived neurotrophic factor and ciliary neurotrophic factor. *J. Neurosci.* 16:3256-3264.

Tang, Z. L., P. E. Scherer, T. Okamoto, K. Song, C. Chu, D. S. Kohtz, I. Nishimoto, H. F. Lodish, and M. P. Lisanti. 1996. Molecular cloning of caveolin-3, a novel member of the caveolin gene family expressed predominantly in muscle. *J. Biol. Chem.* 271:2255-2261.

Tansey, M., R. H. Baloh, J. Milbrandt, and E. M. J. Johnson. 2000. GFRα mediated localization of RET to lipid rafts is required for effective downstream signaling, differenciation and neuronal survival. *Neuron*. 25:611-623.

Tao, H. W., and M. M. Poo. 2001. Retrograde signaling at central synapses. *Proc. Natl. Acad. Sci. USA*. 98:11009-11015.

Tsui-Pierchala, B. A., M. Encinas, J. Milbrandt, and E. M. J. Johnson. 2002. Lipid raft in neuronal signaling and function. *Trends Neurosci.* 25:412-417.

Tyler, W. J., and L. D. Pozzo-Miller. 2001. BDNF enhances quantal neurotransmitter release and increases the number of docked vesicles at the active zones of the hippocampal excitatory synapses. *J. Neurosci.* 21:4249-4258.

Vyas. 2001. Segregation of gangliosides GM1 and GD3 on cell membranes, isolated membrane rafts and defined supported lipid monolayers. *Biol. Chem*. 382:241-250.

Wang, X. H., and M. M. Poo. 1997. Potentiation of developing synapses by postsynaptic release of neurotrophin-4. *Neuron*. 19:825-835.

Wolf, A. A., M. G. Jobling, S. Wimer-Mackin, M. Ferguson-Maltzman, J. L. Madara, R. K. Holmes, and W. I. Lencer. 1998. Ganglioside structure dictates signal transduction by cholera toxin and association with caveolae-like membrane domains in polarized epithelia. *J. Cell Biol*. 141:917-927.

Wu, C., S. Butz, Y. Ying, and R. G. W. Anderson. 1997. Tyrosine kinase receptors concentrated in caveolae-like domains from neuronal plasma membrane. *J. Biol. Chem.* 272:3554-3559.

Xie, K., T. Wang, P. Olafsson, K. Mizuno, and B. Lu. 1997. Activity-dependent expression of NT-3 in muscle cells in culture: implications in the development of neuromuscular junctions. *J. Neurosci.* 17:2947-2958.

Yamashita, T., H. Higuchi, and M. Tohyama. 2002. The p75 receptor transduces the signal from myelin-associated glycoprotein to Rho. *J. Cell Biol*. 157:565-570.

Yan, Q., M. J. Radeke, D. R. Matheson, J. Talvenheimo, A. A. Welcher, and P. Feinstein. 1997. Immunocytochemical localization of trkB in the central nervous system of the adult rat. *J. Comp. Neurol.* 378:135-157.

Anderson, R. G. (1998). The caveolae membrane system. *Annu Rev Biochem* 67, 199-225.

Barbacid, M. (1994). The Trk family of neurotrophin receptors. J Neurobiol 25, 1386-1403.

Blochl, A., and Thoenen, H. (1995). Characterization of nerve growth factor (NGF) release from hippocampal neurons: evidence for a constitutive and an unconventional sodium-dependent regulated pathway. Eur J Neurosci 7, 1220-1228.

Brunner, G., Lang, K., Wolfe, R. A., McClure, D. B., and Sato, G. H. (1981). Selective cell culture of brain cells by serum-free, hormone-supplemented media: a comparative morphological study. Brain Res 254, 563-575.

Butowt, R., and Von Bartheld, C. S. (2003). Connecting the dots: trafficking of neurotrophins, lectins and diverse pathogens by binding to the neurotrophin receptor p75NTR. Eur J Neurosci 17, 673-680.

Chao, M. V. (2003). Neurotrophins and their receptors: a convergence point for many signalling pathways. Nat Rev Neurosci 4, 299-309.

Chao, M. V., and Bothwell, M. (2002). Neurotrophins: to cleave or not to cleave. Neuron 33, 9-12.

Cochilla, A. J., Angleson, J. K., and Betz, W. J. (1999). Monitoring secretory membrane with FM1-43 fluorescence. Annu Rev Neurosci 22, 1-10.

Coen, L., Osta, R., Maury, M., and Brulet, P. (1997). Construction of hybrid proteins that migrate retrogradely and transynaptically into the central nervous system. Proc Natl Acad Sci USA 94, 9400-9405.

Gall, C. M., and Isackson, P. J. (1989). Limbic seizures increase neuronal production of messenger RNA for nerve growth factor. Science 245, 758-761.

Gil, C., Chaib-Oukadour, I., and Aguilera, J. (2003). C-terminal fragment of tetanus toxin heavy chain activates Akt and MEK/ERK signalling pathways in a Trk receptor-dependent manner in cultured cortical neurons. Biochem J 373, 613-620.

Ginty, D. D., and Segal, R. A. (2002). Retrograde neurotrophin signaling: Trk-ing along the axon. Curr Opin Neurobiol 12, 268-274.

Goodman, L. J., Valverde, J., Lim, F., Geschwind, M. D., Federoff, H. J., Geller, A. I., and Hefti, F. (1996). Regulated release and polarized localization of brain-derived neurotrophic factor in hippocampal neurons. Mol Cell Neurosci 7, 222-238.

Heerssen, H. M., and Segal, R. A. (2002). Location, location, location: a spatial view of neurotrophin signal transduction. Trends Neurosci 25, 160-165.

Hering, H., and Sheng, M. (2001). Dendritic spines: structure, dynamics and regulation. Nat Rev Neurosci 2, 880-888.

Kato, A., Ozawa, F., Saitoh, Y., Fukazawa, Y., Sugiyama, H., and Inokuchi, K. (1998). Novel members of the Vesl/Homer family of PDZ proteins that bind metabotropic glutamate receptors. J Biol Chem 273, 23969-23975.

Kostiza, T., and Meier, J. (1996). Nerve growth factors from snake venoms: chemical properties, mode of action and biological significance. Toxicon 34, 787-806.

Kovalchuk, Y., Hanse, E., Kafitz, K. W., and Konnerth, A. (2002). Postsynaptic Induction of BDNF-Mediated Long-Term Potentiation. Science 295, 1729-1734.

Lalli, G., and Schiavo, G. (2002). Analysis of retrograde transport in motor neurons reveals common endocytic carriers for tetanus toxin and neurotrophin receptor p75NTR. J Cell Biol 156, 233-239.

Lu, B., Yokoyama, M., Dreyfus, C. F., and Black, I. B. (1991). Depolarizing stimuli regulate nerve growth factor gene expression in cultured hippocampal neurons. Proc Natl Acad Sci USA 88, 6289-6292.

Maskos, U., Kissa, K., St Cloment, C., and Brulet, P. (2002). Retrograde trans-synaptic transfer of green fluorescent protein allows the genetic mapping of neuronal circuits in transgenic mice. Proc Natl Acad Sci USA 99, 10120-10125.

Matteoli, M., Verderio, C., Rossetto, O., Iezzi, N., Coco, S., Schiavo, G., and Montecucco, C. (1996). Synaptic vesicle endocytosis mediates the entry of tetanus neurotoxin into hippocampal neurons. Proc Natl Acad Sci USA 93, 13310-13315.

McAllister, A. K., Katz, L. C., and Lo, D. C. (1999). Neurotrophins and synaptic plasticity. Annu Rev. Neurosci 22, 295-318.

Mehta, P. P., Battenberg, E., and Wilson, M. C. (1996). SNAP-25 and synaptotagmin involvement in the final Ca(2+)-dependent triggering of neurotransmitter exocytosis. Proc Natl Acad Sci USA 93, 10471-10476.

Miana-Mena, F. J., Roux, S., Benichou, J. C., Osta, R., and Brulet, P. (2002). Neuronal activity-dependent membrane traffic at the neuromuscular junction. Proc Natl Acad Sci USA 99, 3234-3239.

Miller, F. D., and Kaplan, D. R. (2001). On Trk for retrograde signaling. Neuron 32, 767-770.

Ohki, E. C., Tilkins, M. L., Ciccarone, V. C., and Price, P. J. (2001). Improving the transfection efficiency of post-mitotic neurons. J Neurosci Methods 112, 95-99.

Okabe, S., Urushido, T., Konno, D., Okado, H., and Sobue, K. (2001). Rapid redistribution of the postsynaptic density protein PSD-Zip45 (Homer 1 c) and its differential regulation by NMDA receptors and calcium channels. J Neurosci 21, 9561-9571.

Poo, M. M. (2001). Neurotrophins as synaptic modulators. Nat Rev Neurosci 2, 24-32.

Sheng, M. (2001). Molecular organization of the postsynaptic specialization. Proc Natl Acad Sci USA 98, 7058-7061.

Tyler, W. J., Perrett, S. P., and Pozzo-Miller, L. D. (2002). The role of neurotrophins in neurotransmitter release. Neuroscientist 8, 524-531.

Tyler, W. J., and Pozzo-Miller, L. D. (2001). BDNF enhances quantal neurotransmitter release and increases the number of docked vesicles at the active zones of hippocampal excitatory synapses. J Neurosci 21, 4249-4258.

Vazquez-Martinez, R., Shorte, S. L., Boockfor, F. R., and Frawley, L. S. (2001a). Synchronized exocytotic bursts from gonadotropin-releasing hormone-expressing cells: dual control by intrinsic cellular pulsatility and gap junctional communication. Endocrinology 142, 2095-2101.

Vazquez-Martinez, R., Shorte, S. L., Faught, W. J., Leaumont, D. C., Frawley, L. S., and Boockfor, F. R. (2001b). Pulsatile exocytosis is functionally associated with GnRH gene expression in immortalized GnRH-expressing cells. Endocrinology 142, 5364-5370.

Xiao, B., Tu, J. C., Petralia, R. S., Yuan, J. P., Doan, A., Breder, C. D., Ruggiero, A., Lanahan, A. A., Wenthold, R. J., and Worley, P. F. (1998). Homer regulates the association of group 1 metabotropic glutamate receptors with multivalent complexes of homer-related, synaptic proteins. Neuron 21, 707-716.

Yano, H., Lee, F. S., Kong, H., Chuang, J., Arevalo, J., Perez, P., Sung, C., and Chao, M. V. (2001). Association of Trk neurotrophin receptors with components of the cytoplasmic dynein motor. J Neurosci 21, RC125.

Zafra, F., Castren, E., Thoenen, H., and Lindholm, D. (1991). Interplay between glutamate and gamma-aminobutyric acid transmitter systems in the physiological regulation of brain-derived neurotrophic factor and nerve growth factor synthesis in hippocampal neurons. Proc Natl Acad Sci USA 88, 10037-10041.

Pyle, J. L., Kavalali, E. T., Choi, S., and Tsien, R. W. (1999). Visualization of synaptic activity in hipocampal slices with FM1-43 enabled by fluorescence quenching. Neuron 24, 803-808.

Betz, W. J., Angleson, J. K., (1998). The synaptic vesicle cycle. Annu. Rev. Physiol, 60:347-363.

Soudais, C., Laplace-Builhe, C., Kissa, K., Kremer, E. J., (2001). Preferential transduction of neurons by canine adenovirus vectors and their efficient retrograde transport in vivo. FASEB J. 15:2283-2285.

Shimada, A., Mason C. A., Morrison, M. E., (1998). TrkB signaling modulates spine density and morphology independent of dendrite structure in cultured neonatal Purkinje cells. J. Neurosci. 18:8559-8570.

What is claimed is:

1. A method of evaluating the state of networking activity of a neuron, wherein the method comprises visualizing, ex vivo or in vitro, a biomarker in dendritic spines of the cells of a synapse of the neuron, wherein the biomarker comprises at least fragment C of tetanus toxin (TTC) tagged with a reporter protein chosen from beta-Galactosidase (β-gal), green fluorescent protein (GFP), red fluorescent protein (RFP), yellow fluorescent protein (YFP), cyan fluorescent protein (CFP), Discosoma sp, red fluorescent protein (DsRED), and *Heteractis crispa* far-red fluorescent variant (HcRED), and wherein an elevated amount of the biomarker in the dendritic spines relative to the amount of the biomarker in dendritic shaft regions indicates a neuron that is forming synaptic connections.

2. The method as claimed in claim 1, wherein the biomarker is a fusion protein comprised of at least a fragment C of tetanus toxin and a reporter protein chosen from β-gal, GFP, RFP, YFP, CFP, DsRED, and HcRED.

3. The method as claimed in claim 1, wherein the biomarker is visualized in vitro.

4. The method as claimed in claim 3, wherein the cells having dendritic spines are dissociated cortical cells of an active synapse.

5. The method as claimed in claim 3, which comprises visualizing postsynaptic dendritic spines that maintain functional interactions with active presynaptic terminals.

6. The method as claimed in claim 1, wherein the biomarker comprises:
   (A) a non-toxic fragment of tetanus toxin comprising a fragment C of tetanus toxin; or
   (B) a non-toxic fragment of tetanus toxin comprising a fragment C and a fragment B or a fraction thereof of at least 11 amino acid residues; or
   (C) a non-toxic fragment of tetanus toxin comprising a fragment C, and a fragment B or a fraction thereof of at least 11 amino acid residues, and a fraction of fragment A devoid of its toxic activity corresponding to the proteolytic domain having a zinc-binding motif located in the central part of the chain between amino acids 225 and 245.

7. A method of evaluating the state of networking activity of a neuron, wherein the method comprises
   (A) exposing cells of a synapse having dendritic spines to a biomarker in vitro; and
   (B) visualizing, ex vivo or in vitro, the biomarker in dendritic spines of the cells of the synapse of the neuron, wherein the biomarker comprises at least fragment C of tetanus toxin (TTC) tagged with a reporter protein chosen from beta-Galactosidase (β-gal), green fluorescent protein (GFP), red fluorescent protein (RFP), yellow fluorescent protein (YFP), cyan fluorescent protein (CFP), Discosoma sp, red fluorescent protein (DsRED), and *Heteractis crispa* far-red fluorescent variant (HcRED),
   wherein an elevated amount of the biomarker in the dendritic spines relative to the amount of the biomarker in dendritic shaft regions indicates a neuron that is forming synaptic connections.

8. A method of evaluating the state of networking activity of a neuron, wherein the method comprises
   (A) exposing cells of a synapse having dendritic spines to a biomarker in vivo; and
   (B) visualizing, ex vivo or in vitro, the biomarker in dendritic spines of the cells of the synapse of the neuron, wherein the biomarker comprises at least fragment C of tetanus toxin (TTC) tagged with a reporter protein chosen from beta-Galactosidase (β-gal), green fluorescent protein (GFP), red fluorescent protein (RFP), yellow fluorescent protein (YFP), cyan fluorescent protein (CFP), Discosoma sp, red fluorescent protein (DsRED), and *Heteractis crispa* far-red fluorescent variant (HcRED),
   wherein an elevated amount of the biomarker in the dendritic spines relative to the amount of the biomarker in dendritic shaft regions indicates a neuron that is forming synaptic connections.

9. The method as claimed in claim 8, wherein an animal contains the active synapse comprised of the cells having the dendritic spines, and the cells are exposed to the biomarker by intramuscular injection of the biomarker into the animal.

10. The method as claimed in claim 8, wherein an animal contains the active synapse comprised of the cells having the dendritic spines, and the cells are exposed to the biomarker by subcutaneous injection of the biomarker into the immediate vicinity of the Levator auris longus (LAL) muscle of the animal for transport to hypoglossal motoneurons.

11. The method as claimed in claim 7 or 8, wherein the cells are exposed to the biomarker by expressing a nucleic acid sequence, which encodes the biomarker, in the cells.

12. The method as claimed in claim 11, wherein the cells are cells of a non-human, transgenic animal.

13. A method of evaluating the state of networking activity of a neuron, wherein the method comprises:
   (A) providing an active synapse comprised of cells having dendritic spines;
   (B) transfecting in vitro the cells having dendritic spines with a vector that expresses a biomarker comprising at least fragment C of tetanus toxin (TTC) fused with a reporter protein chosen from β-gal, GFP, RFP, YFP, CFP, DsRED, and HcRED;
   (C) selecting, in vitro, transfected cells that are positive for expression of the biomarker;
   (D) providing a central nervous system (CNS) or a spinal cord of an animal;
   (E) implanting the transfected cells in the CNS or spinal cord; and
   (F) visualizing, ex vivo or in vitro, the biomarker in dendritic spines of an active synapse, wherein an elevated amount of the biomarker in the dendritic spines relative to the amount of the biomarker in dendritic shaft regions indicates a neuron that is forming synaptic connections.

14. A method of evaluating the state of networking activity of a neuron, wherein the method comprises:
   (A) providing cells of an active synapse, wherein the cells have dendritic spines, and the dendritic spines contain an accumulation of a biomarker that has been transported into the dendritic spines; and
   (B) visualizing the biomarker in the dendritic spines in vitro;
   wherein the biomarker is a fusion protein comprising at least fragment C of tetanus toxin (TTC) tagged with a reporter protein chosen from β-gal, GFP, RFP, YFP, CFP, DsRED, and HcRED, wherein an elevated amount of the biomarker in the dendritic spines relative to the amount of the biomarker in dendritic shaft regions indicates a neuron that is forming synaptic connections.

15. The method as claimed in claim 14, wherein the cells having dendritic spines are dissociated cortical cells of an active synapse.

16. The method as claimed in claim 14, which comprises visualizing postsynaptic dendritic spines that maintain functional interactions with active presynaptic terminals.

17. The method as claimed in claim 14, wherein the fusion protein comprises:
(A) a non-toxic fragment of tetanus toxin comprising a fragment C of tetanus toxin; or
(B) a non-toxic fragment of tetanus toxin comprising a fragment C and a fragment B or a fraction thereof of at least 11 amino acid residues; or
(C) a non-toxic fragment of tetanus toxin comprising a fragment C, and a fragment B or a fraction thereof of at least 11 amino acid residues, and a fraction of fragment A devoid of its toxic activity corresponding to the proteolytic domain having a zinc-binding motif located in the central part of the chain between amino acids 225 and 245.

18. The method as claimed in any one of claims 14-17, wherein the fusion protein is GFP-TTC.

19. The method as claimed in any one of claims 1, 7, 8, 13, and 14, wherein the biomarker is GFP-TTC.

20. The method as claimed in any one of claims 1, 7, 8, 13, and 14, which comprises providing a spinal cord containing the cells having the dendritic spines, and visualizing the biomarker in the spinal cord.

21. The method as claimed in any one of claims 1, 7, 8, 13, and 14, which comprises providing brain tissue containing the cells having the dendritic spines, and visualizing the biomarker in the brain tissue.

22. The method as claimed in any one of claims 1, 7, 8, and 13, wherein the cells having the dendritic spines are dissociated cortical cells of an active synapse.

23. An ex vivo or in vitro method of evaluating the state of networking activity of a neuron in an animal, the method comprising injecting a biomarker into a muscle of the animal wherein the biomarker comprises at least fragment C of tetanus toxin (TTC) fused to a reporter protein chosen from beta-Galactosidase (β-gal), green fluorescent protein (GFP), red fluorescent protein (RFP), yellow fluorescent protein (YFP), cyan fluorescent protein (CFP), Discosoma sp, red fluorescent protein (DsRED), and *Heteractis crispa* far-red fluorescent variant (HcRED), wherein an elevated amount of the biomarker in the dendritic spines relative to the amount of the biomarker in dendritic shaft regions indicates a neuron that is forming synaptic connections.

* * * * *

SEQUENCE LISTING

<160> NUMBER OF SEQ ID NOS: 18

<210> SEQ ID NO 1
<211> LENGTH: 1600
<212> TYPE: DNA
<213> ORGANISM: Clostridium tetani
<220> FEATURE:
<221> NAME/KEY: CDS
<222> LOCATION: (88)..(1476)

<400> SEQUENCE: 1

```
ggaaacagct atgaccatga ttacgccaag ctcgaaatta accctcacta aagggaacaa      60
aagctggagc tcggtacccg gccacc atg gtt ttt tca aca cca att cca ttt     114
                              Met Val Phe Ser Thr Pro Ile Pro Phe
                                1               5 tct tat tct aaa aat ctg gat tgt tgg gtt gat aat gaa gaa gat ata       162
Ser Tyr Ser Lys Asn Leu Asp Cys Trp Val Asp Asn Glu Glu Asp Ile
 10              15                  20                  25 gat gtt ata tta aaa aag agt aca att tta aat tta gat att aat aat       210
Asp Val Ile Leu Lys Lys Ser Thr Ile Leu Asn Leu Asp Ile Asn Asn
             30                  35                  40 gat att ata tca gat ata tct ggg ttt aat tca tct gta ata aca tat       258
Asp Ile Ile Ser Asp Ile Ser Gly Phe Asn Ser Ser Val Ile Thr Tyr
         45                  50                  55 cca gat gct caa ttg gtg ccc gga ata aat ggc aaa gca ata cat tta       306
Pro Asp Ala Gln Leu Val Pro Gly Ile Asn Gly Lys Ala Ile His Leu
     60                  65                  70 gta aac aat gaa tct tct gaa gtt ata gtg cat aaa gct atg gat att       354
Val Asn Asn Glu Ser Ser Glu Val Ile Val His Lys Ala Met Asp Ile
 75                  80                  85 gaa tat aat gat atg ttt aat aat ttt acc gtt agc ttt tgg ttg agg       402
Glu Tyr Asn Asp Met Phe Asn Asn Phe Thr Val Ser Phe Trp Leu Arg
             90                  95                 100                 105 gtt cct aaa gta tct gct agt cat tta gaa caa tat ggc aca aat gag       450
Val Pro Lys Val Ser Ala Ser His Leu Glu Gln Tyr Gly Thr Asn Glu
                110                 115                 120 tat tca ata att agc tct atg aaa aaa cat agt cta tca ata gga tct       498
Tyr Ser Ile Ile Ser Ser Met Lys Lys His Ser Leu Ser Ile Gly Ser
        125                 130                 135 ggt tgg agt gta tca ctt aaa ggt aat aac tta ata tgg act tta aaa       546
Gly Trp Ser Val Ser Leu Lys Gly Asn Asn Leu Ile Trp Thr Leu Lys
    140                 145                 150 gat tcc gcg gga gaa gtt aga caa ata act ttt agg gat tta cct gat       594
Asp Ser Ala Gly Glu Val Arg Gln Ile Thr Phe Arg Asp Leu Pro Asp
155                 160                 165 aaa ttt aat gct tat tta gca aat aaa tgg gtt ttt ata act att act       642
Lys Phe Asn Ala Tyr Leu Ala Asn Lys Trp Val Phe Ile Thr Ile Thr
170                 175                 180                 185 aat gat aga tta tct tct gct aat ttg tat ata aat gga gta ctt atg       690
Asn Asp Arg Leu Ser Ser Ala Asn Leu Tyr Ile Asn Gly Val Leu Met
                190                 195                 200 gga agt gca gaa att act ggt tta gga gct att aga gag gat aat aat       738
Gly Ser Ala Glu Ile Thr Gly Leu Gly Ala Ile Arg Glu Asp Asn Asn
        205                 210                 215 ata aca tta aaa cta gat aga tgt aat aat aat aat caa tac gtt tct       786
Ile Thr Leu Lys Leu Asp Arg Cys Asn Asn Asn Asn Gln Tyr Val Ser
    220                 225                 230 att gat aaa ttt agg ata ttt tgc aaa gca tta aat cca aaa gag att       834
Ile Asp Lys Phe Arg Ile Phe Cys Lys Ala Leu Asn Pro Lys Glu Ile
235                 240                 245
```

|  |  | 882 |
|---|---|---|
| gaa aaa tta tac aca agt tat tta tct ata acc ttt tta aga gac ttc | | |
| Glu Lys Leu Tyr Thr Ser Tyr Leu Ser Ile Thr Phe Leu Arg Asp Phe | | |
| 250 255 260 265 | | |
| tgg gga aac cct tta cga tat gat aca gaa tat tat tta ata cca gta | | 930 |
| Trp Gly Asn Pro Leu Arg Tyr Asp Thr Glu Tyr Tyr Leu Ile Pro Val | | |
| 270 275 280 | | |
| gct tct agt tct aaa gat gtt caa ttg aaa aat ata aca gat tat atg | | 978 |
| Ala Ser Ser Ser Lys Asp Val Gln Leu Lys Asn Ile Thr Asp Tyr Met | | |
| 285 290 295 | | |
| tat ttg aca aat gcg cca tcg tat act aac gga aaa ttg aat ata tat | | 1026 |
| Tyr Leu Thr Asn Ala Pro Ser Tyr Thr Asn Gly Lys Leu Asn Ile Tyr | | |
| 300 305 310 | | |
| tat aga agg tta tat aat gga cta aaa ttt att ata aaa aga tat aca | | 1074 |
| Tyr Arg Arg Leu Tyr Asn Gly Leu Lys Phe Ile Ile Lys Arg Tyr Thr | | |
| 315 320 325 | | |
| cct aat aat gaa ata gat tct ttt gtt aaa tca ggt gat ttt att aaa | | 1122 |
| Pro Asn Asn Glu Ile Asp Ser Phe Val Lys Ser Gly Asp Phe Ile Lys | | |
| 330 335 340 345 | | |
| tta tat gta tca tat aac aat aat gag cac att gta ggt tat ccg aaa | | 1170 |
| Leu Tyr Val Ser Tyr Asn Asn Asn Glu His Ile Val Gly Tyr Pro Lys | | |
| 350 355 360 | | |
| gat gga aat gcc ttt aat aat ctt gat aga att cta aga gta ggt tat | | 1218 |
| Asp Gly Asn Ala Phe Asn Asn Leu Asp Arg Ile Leu Arg Val Gly Tyr | | |
| 365 370 375 | | |
| aat gcc cca ggt atc cct ctt tat aaa aaa atg gaa gca gta aaa ttg | | 1266 |
| Asn Ala Pro Gly Ile Pro Leu Tyr Lys Lys Met Glu Ala Val Lys Leu | | |
| 380 385 390 | | |
| cgt gat tta aaa acc tat tct gta caa ctt aaa tta tat gat gat aaa | | 1314 |
| Arg Asp Leu Lys Thr Tyr Ser Val Gln Leu Lys Leu Tyr Asp Asp Lys | | |
| 395 400 405 | | |
| aat gca tct tta gga cta gta ggt acc cat aat ggt caa ata ggc aac | | 1362 |
| Asn Ala Ser Leu Gly Leu Val Gly Thr His Asn Gly Gln Ile Gly Asn | | |
| 410 415 420 425 | | |
| gat cca aat agg gat ata tta att gca agc aac tgg tac ttt aat cat | | 1410 |
| Asp Pro Asn Arg Asp Ile Leu Ile Ala Ser Asn Trp Tyr Phe Asn His | | |
| 430 435 440 | | |
| tta aaa gat aaa att tta gga tgt gat tgg tac ttt gta cct aca gat | | 1458 |
| Leu Lys Asp Lys Ile Leu Gly Cys Asp Trp Tyr Phe Val Pro Thr Asp | | |
| 445 450 455 | | |
| gag gga tgg aca aat gat taaacagatt gatatgttca tgacatatgc | | 1506 |
| Glu Gly Trp Thr Asn Asp | | |
| 460 | | |
| ccgggatcct ctagagtcga cctcgagggg gggcccggta cccaattcgc cctatagtga | | 1566 |
| gtcgtattac aattcactgg ccgtcgtttt acaa | | 1600 |

```
<210> SEQ ID NO 2
<211> LENGTH: 463
<212> TYPE: PRT
<213> ORGANISM: Clostridium tetani

<400> SEQUENCE: 2
```

Met Val Phe Ser Thr Pro Ile Pro Phe Ser Tyr Ser Lys Asn Leu Asp
1               5                   10                  15

Cys Trp Val Asp Asn Glu Glu Asp Ile Asp Val Ile Leu Lys Lys Ser
            20                  25                  30

Thr Ile Leu Asn Leu Asp Ile Asn Asn Asp Ile Ile Ser Asp Ile Ser
        35                  40                  45

Gly Phe Asn Ser Ser Val Ile Thr Tyr Pro Asp Ala Gln Leu Val Pro
    50                  55                  60

```
Gly Ile Asn Gly Lys Ala Ile His Leu Val Asn Asn Glu Ser Ser Glu
 65                  70                  75                  80

Val Ile Val His Lys Ala Met Asp Ile Glu Tyr Asn Asp Met Phe Asn
             85                  90                  95

Asn Phe Thr Val Ser Phe Trp Leu Arg Val Pro Lys Val Ser Ala Ser
            100                 105                 110

His Leu Glu Gln Tyr Gly Thr Asn Glu Tyr Ser Ile Ile Ser Ser Met
        115                 120                 125

Lys Lys His Ser Leu Ser Ile Gly Ser Gly Trp Ser Val Ser Leu Lys
    130                 135                 140

Gly Asn Asn Leu Ile Trp Thr Leu Lys Asp Ser Ala Gly Glu Val Arg
145                 150                 155                 160

Gln Ile Thr Phe Arg Asp Leu Pro Asp Lys Phe Asn Ala Tyr Leu Ala
                165                 170                 175

Asn Lys Trp Val Phe Ile Thr Ile Thr Asn Asp Arg Leu Ser Ser Ala
            180                 185                 190

Asn Leu Tyr Ile Asn Gly Val Leu Met Gly Ser Ala Glu Ile Thr Gly
        195                 200                 205

Leu Gly Ala Ile Arg Glu Asp Asn Asn Ile Thr Leu Lys Leu Asp Arg
210                 215                 220

Cys Asn Asn Asn Asn Gln Tyr Val Ser Ile Asp Lys Phe Arg Ile Phe
225                 230                 235                 240

Cys Lys Ala Leu Asn Pro Lys Glu Ile Glu Lys Leu Tyr Thr Ser Tyr
                245                 250                 255

Leu Ser Ile Thr Phe Leu Arg Asp Phe Trp Gly Asn Pro Leu Arg Tyr
            260                 265                 270

Asp Thr Glu Tyr Tyr Leu Ile Pro Val Ala Ser Ser Ser Lys Asp Val
        275                 280                 285

Gln Leu Lys Asn Ile Thr Asp Tyr Met Tyr Leu Thr Asn Ala Pro Ser
    290                 295                 300

Tyr Thr Asn Gly Lys Leu Asn Ile Tyr Tyr Arg Arg Leu Tyr Asn Gly
305                 310                 315                 320

Leu Lys Phe Ile Ile Lys Arg Tyr Thr Pro Asn Asn Glu Ile Asp Ser
                325                 330                 335

Phe Val Lys Ser Gly Asp Phe Ile Lys Leu Tyr Val Ser Tyr Asn Asn
            340                 345                 350

Asn Glu His Ile Val Gly Tyr Pro Lys Asp Gly Asn Ala Phe Asn Asn
        355                 360                 365

Leu Asp Arg Ile Leu Arg Val Gly Tyr Asn Ala Pro Gly Ile Pro Leu
    370                 375                 380

Tyr Lys Lys Met Glu Ala Val Lys Leu Arg Asp Leu Lys Thr Tyr Ser
385                 390                 395                 400

Val Gln Leu Lys Leu Tyr Asp Asp Lys Asn Ala Ser Leu Gly Leu Val
                405                 410                 415

Gly Thr His Asn Gly Gln Ile Gly Asn Asp Pro Asn Arg Asp Ile Leu
            420                 425                 430

Ile Ala Ser Asn Trp Tyr Phe Asn His Leu Lys Asp Lys Ile Leu Gly
        435                 440                 445

Cys Asp Trp Tyr Phe Val Pro Thr Asp Glu Gly Trp Thr Asn Asp
    450                 455                 460

<210> SEQ ID NO 3
<211> LENGTH: 1392
<212> TYPE: DNA
```

-continued

<213> ORGANISM: Clostridium tetani

<400> SEQUENCE: 3

| | |
|---|---|
| atggtttttt caacaccaat tccattttct tattctaaaa atctggattg ttgggttgat | 60 |
| aatgaagaag atatagatgt tatattaaaa aagagtacaa ttttaaattt agatattaat | 120 |
| aatgatatta tatcagatat atctgggttt aattcatctg taataacata tccagatgct | 180 |
| caattggtgc ccggaataaa tggcaaagca atacatttag taaacaatga atcttctgaa | 240 |
| gttatagtgc ataaagctat ggatattgaa tataatgata tgtttaataa ttttaccgtt | 300 |
| agcttttggt tgagggttcc taaagtatct gctagtcatt tagaacaata tggcacaaat | 360 |
| gagtattcaa taattagctc tatgaaaaaa catagtctat caataggatc tggttggagt | 420 |
| gtatcactta aagtaataa cttaatatgg actttaaaag attccgcggg agaagttaga | 480 |
| caaataactt ttagggattt acctgataaa tttaatgctt atttagcaaa taatgggtt | 540 |
| tttataacta ttactaatga tagattatct tctgctaatt tgtatataaa tggagtactt | 600 |
| atgggaagtg cagaaattac tggtttagga gctattagag aggataataa tataacatta | 660 |
| aaactagata gatgtaataa taataatcaa tacgtttcta ttgataaatt taggatattt | 720 |
| tgcaaagcat taaatccaaa agagattgaa aaattataca caagttattt atctataacc | 780 |
| tttttaagag acttctgggg aaacccttta cgatatgata cagaatatta tttaatacca | 840 |
| gtagcttcta gttctaaaga tgttcaattg aaaaatataa cagattatat gtatttgaca | 900 |
| aatgcgccat cgtatactaa cggaaaattg aatatatatt atagaaggtt atataatgga | 960 |
| ctaaaattta ttataaaaag atatacacct aataatgaaa tagattcttt tgttaaatca | 1020 |
| ggtgatttta ttaaattata tgtatcatat aacaataatg agcacattgt aggttatccg | 1080 |
| aaagatggaa atgcctttaa taatcttgat agaattctaa gagtaggtta taatgcccca | 1140 |
| ggtatccctc tttataaaaa aatggaagca gtaaaattgc gtgatttaaa aacctattct | 1200 |
| gtacaactta attatatga tgataaaaat gcatctttag gactagtagg tacccataat | 1260 |
| ggtcaaatag caacgatcc aaataggggat atattaattg caagcaactg gtactttaat | 1320 |
| catttaaaag ataaaatttt aggatgtgat tggtactttg tacctacaga tgagggatgg | 1380 |
| acaaatgatt aa | 1392 |

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 4

| | |
|---|---|
| ccccccgggc caccatggtt ttttcaacac caattccatt ttcttattc | 49 |

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5

| | |
|---|---|
| ctaaaccagt aatttctg | 18 |

<210> SEQ ID NO 6
<211> LENGTH: 25
<212> TYPE: DNA

```
<213> ORGANISM: Artificial Sequence
<220> FEATURE:
<223> OTHER INFORMATION: Description of Artificial Sequence: Primer

<400> SEQUENCE: 6
aattatggac tttaaaagat tccgc                                    25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
ggcattataa cctactctta gaat                                     24

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 8 aatgcccttta ataatcttga tagaaat                                 27

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 9
ccccccgggc atatgtcatg aacatatcaa tctgtttaat c                  41

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
ctgaatatcg acggtttcca tatg                                     24

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 11
ggcagtctcg agtctagacc atggcttttt gacaccagac                    40

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 12
catgactggg gatccccagt                                          20
```

-continued

```
<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
tatgataaaa atgcatcttt agga                                          24

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 14
tggagtcgac gctagcagga tcatttgtcc atccttc                            37

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 15 gctagcgc                                                             8

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 16
gatatcggcg cgccagc                                                  17

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 17
tggcgcgccg atatcgc                                                  17

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 18
tcgatggcgc gcca                                                     14
```